(12) United States Patent
Lin

(10) Patent No.: US 11,319,354 B2
(45) Date of Patent: May 3, 2022

(54) VGLL4 WITH UCP-1 CIS-REGULATORY ELEMENT AND METHOD OF USE THEREOF

(71) Applicant: MASONIC MEDICAL RESEARCH LABORATORY, Utica, NY (US)

(72) Inventor: Zhiqiang Lin, Utica, NY (US)

(73) Assignee: MASONIC MEDICAL RESEARCH LABORATORY, Utica, NY (US)

( * ) Notice: Subject to any disclaimer, the term of this patent is extended or adjusted under 35 U.S.C. 154(b) by 0 days.

(21) Appl. No.: 16/925,632

(22) Filed: Jul. 10, 2020

(65) Prior Publication Data
US 2021/0009646 A1    Jan. 14, 2021

Related U.S. Application Data

(60) Provisional application No. 62/872,624, filed on Jul. 10, 2019.

(51) Int. Cl.
*C12N 15/86* (2006.01)
*C07K 14/47* (2006.01)

(52) U.S. Cl.
CPC .......... *C07K 14/4705* (2013.01); *C12N 15/86* (2013.01); *C12N 2750/14143* (2013.01); *C12N 2830/001* (2013.01)

(58) Field of Classification Search
None
See application file for complete search history.

(56) References Cited

U.S. PATENT DOCUMENTS

| | | | |
|---|---|---|---|
| 8,455,204 B2 | 6/2013 | Boss et al. | |
| 8,852,939 B2 | 10/2014 | Hall et al. | |
| 9,034,839 B2 | 5/2015 | Thibonnier | |
| 2016/0319303 A1* | 11/2016 | Jimenez Cenzano | ........................ C12Y 207/01002 |
| 2017/0290926 A1 | 10/2017 | Smith et al. | |
| 2021/0017606 A1* | 1/2021 | Li | ........................ A61P 13/08 |

FOREIGN PATENT DOCUMENTS

| | | | | |
|---|---|---|---|---|
| WO | WO-2008021290 A2 * | 2/2008 | ............... | A61P 35/00 |
| WO | WO-2014023808 A2 * | 2/2014 | ....... | G01N 33/57415 |
| WO | WO-2017127750 A1 * | 7/2017 | ........... | C12N 15/113 |
| WO | 2018215613 A1 | 11/2018 | | |
| WO | WO-2018215613 A1 * | 11/2018 | ........... | A61K 35/761 |

OTHER PUBLICATIONS

Zhang (JBC, 293(44): 17119-17134, 2018 (Year: 2018).*
Ji et al CN104548131, 2015 (Year: 2015).*
Mehtali EP1995309, 2008 (Year: 2008).*

International Search Report and Written Opinion of the International Searching Authority for International Application No. PCT/US2020/041496 dated Sep. 17, 2020.
Zhang et al., "The TEA domain family transcription factor TEAD4 represses murine adipogenesis by recruiting the cofactors VGLL4 and CtBP2 into a transitional complex", Journal of Biological Chemistry, vol. 293, No. 44, pp. 17119-17134, Sep. 12, 2018.
Gao et al., "Computational insights into the interaction mechanism of transcription cofactor vestigial-like protein 4 binding to TEA domain transcription factor 4 by molecular dynamics simulation and molecular mechanics generalized Born/surface area) calculation", Journal of Biomolecular Structure & Dynamics, vol. 37, No. 10, pp. 2538-2545, Nov. 9, 2018.
Cassard, A., el al., "Human Uncoupling Protein Gene: Structure, Comparison With Rat Gene, and Assignment to the Long Arm of Chromosome 4", Journal of Cellular Biochemistry, vol. 43, pp. 255-264 (1990).
Jiao, S., et al., "A Peptide Mimicking VGLL4 Function Acts as a YAP Antagonist Therapy against Gastric Cancer", Cancer Cell, vol. 25, pp. 166-180 (2014).
Gonzalez-Barroso, M., et al., "Transcriptional Activation of the Human ucp1 Gene in a Rodent Cell Line", The Journal of Biological Chemistry, vol. 275, No. 41, pp. 31722-31732 (2000).
Deng, X., et al., "VGLL4 is a transcriptional cofactor acting as a novel tumor suppressor via interacting with TEADs", Am J Cancer Res, vol. 8, No. 6, pp. 932-943 (2018).
"Minutes of the 48th General Assembly of the European Association for the Study of Diabetes", Diabetologia, vol. 56, Suppl 1, S1 and S319 (2013).
Cassard-Doulcier, A., et al., "A 211-bp enhancer of the rat uncoupling protein-1 (UCP-1) gene controls specific and regulated expression in brown adipose tissue", Biochem. J., vol. 333, pp. 243-246 (1998).
Chen, H., et al., "Vgl-4, a Novel Member of the Vestigial like Family of Transcription Cofactors, Regulates α1-Adrenergic Activation of Gene Expression in Cardiac Myocytes", The Journal of Biological Chemistry, vol. 279, No. 29, pp. 30806-30806 (2004).
Kozak, U.C., et al., "An Upstream Enhancer Regulating Brown-Fat-Specific Expression of the Mitochondrial Uncoupling Protein Gene", Molecular and Cellular Biology, vol. 14, No. 1, pp. 59-67 (1994).
Larose, M., et al., "Essential cis-Acting Elements in Rat Uncoupling Protein Gene Are in an Enhancer Containing a Complex Retinoic Acid Response Domain", vol. 271, No. 49, pp. 31533-31542 (1996).

(Continued)

*Primary Examiner* — Anoop K Singh
*Assistant Examiner* — Magdalene K Sgagias
(74) *Attorney, Agent, or Firm* — Heslin Rothenberg Farley & Mesiti P.C.

(57) ABSTRACT

Provided is a polynucleotide, including a cis-regulatory element and a nucleotide sequence encoding a vestigial like 4 protein, wherein the cis-regulatory element includes an uncoupling protein 1 enhancer and an uncoupling protein 1 promoter. Also provided is a viral vector including said polynucleotide. Also provided is a method of transfecting a cell or a subject with said polynucleotide or said viral vector.

20 Claims, 24 Drawing Sheets

Specification includes a Sequence Listing.

(56) References Cited

OTHER PUBLICATIONS

Rim, J.S., et al., "Regulatory Motifs for CREB-binding Protein and Nfe212 Transcription Factors in the Upstream Enhancer of the Mitochondrial Uncoupling Protein 1 Gene", The Journal of Biological Chemistry, vol. 277, No. 37, pp. 34589-34600 (2002).
Shore, A., et al., "Role of Ucp1 enhancer methylation and chromatin remodelling in the control of Ucp1 expression in murine adipose tissue", Diabetologia, vol. 53, pp. 1164-1173 (2010).
Zhang, Y., et al., "A growing role for the Hippo signaling pathway in the heart: Hippo pathway function in the heart", J Mol Med (Berl), vol. 95, No. 5, pp. 465-472 (2017).
Skarnes, W.C., et al., "A conditional knockout resource for the genome-wide study of mouse gene function", Nature, vol. 474, pp. 337-344 (2011).

* cited by examiner

```
                    TDU_1                      TDU_2
         _____    _____
hVGLL4       DPVVEEHFRRSLGKNY...TGSVDDHFAKALGDTW
hVGLL4^HF4A  DPVVEEAARRSLGKNY...TGSVDDAAAKALGDTW
``` hVGLL4 TDU_1: SEQ ID NO: 41
hVGLL4 TDU_2: SEQ ID NO: 42
hVGLL4-HF4A TDU_1: SEQ ID NO: 43
hVGLL4-HF4A TDU_2: SEQ ID NO: 44

FIG. 33BFIG. 33C

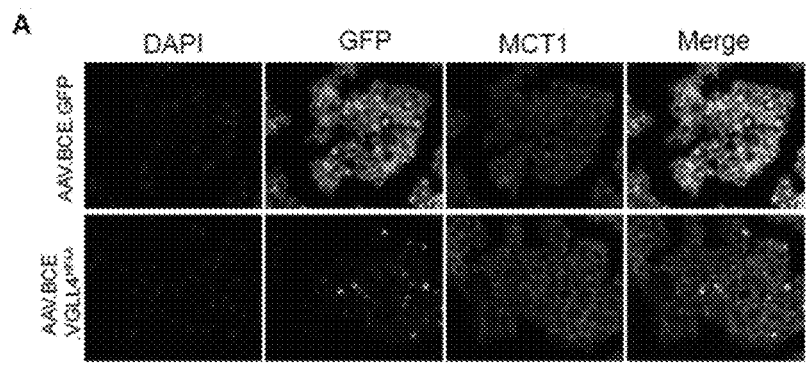 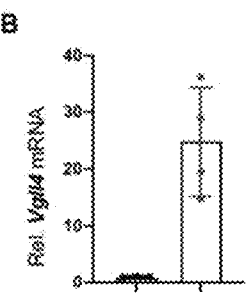
FIG. 34A          FIG. 34B
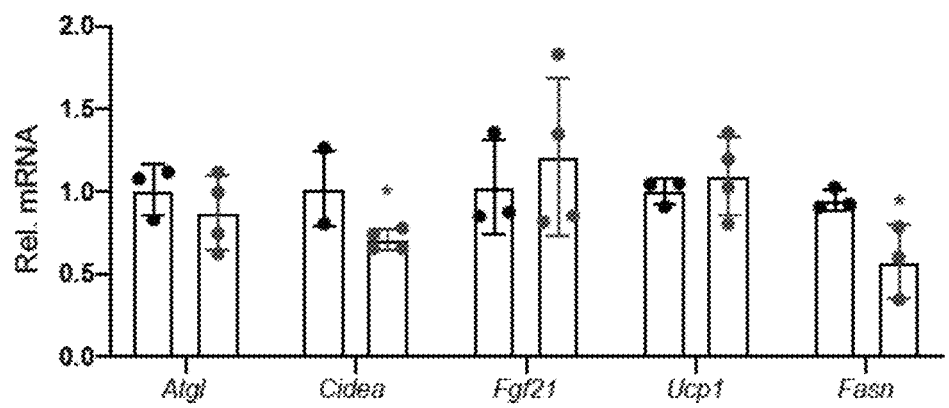
FIG. 34C
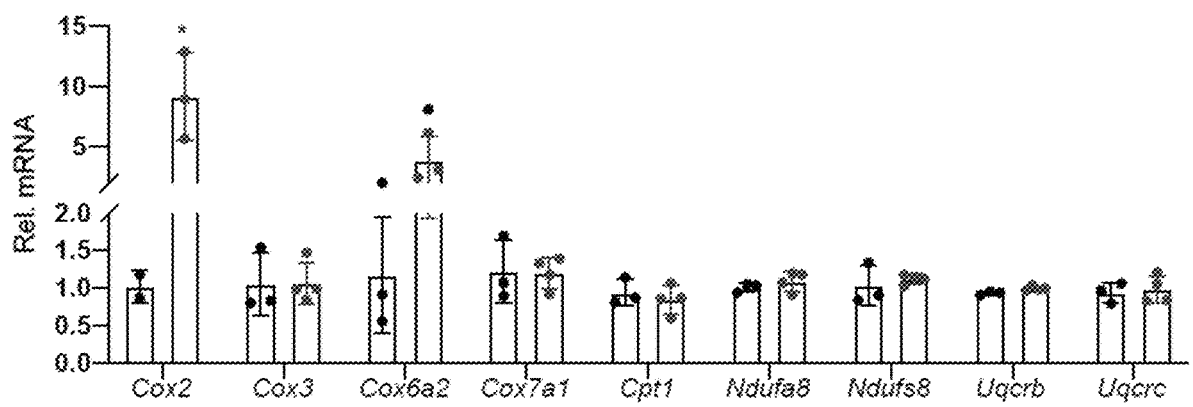
FIG. 34D

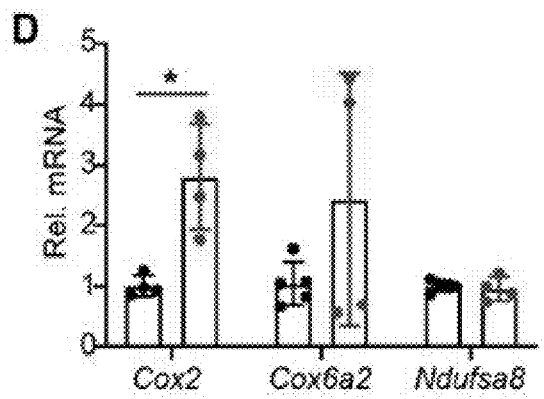
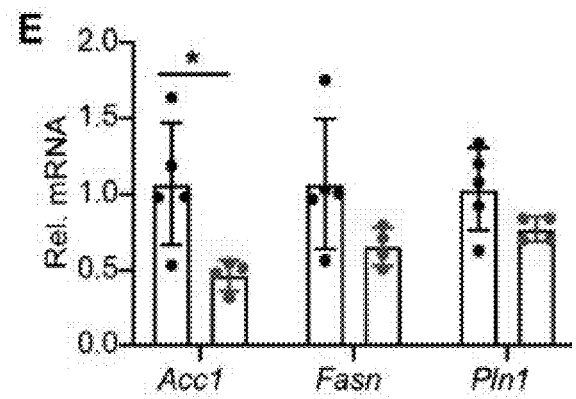
FIG. 36D
FIG. 36E
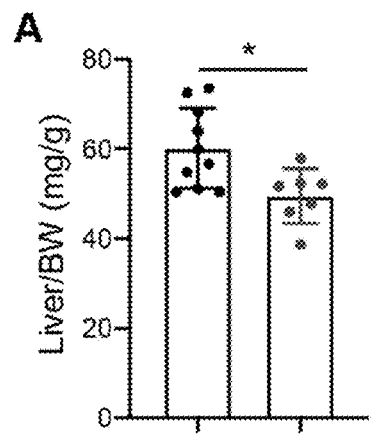
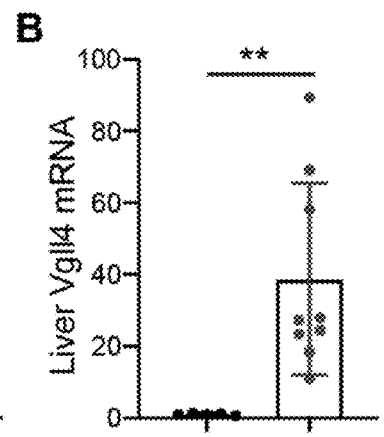
FIG. 37A
FIG. 37B
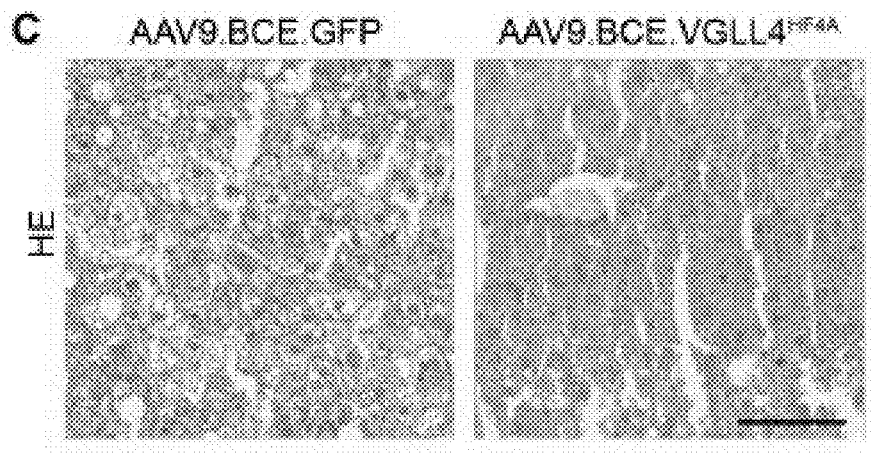
FIG. 37C

SEQUENCE LISTING

<160> NUMBER OF SEQ ID NOS: 44

<210> SEQ ID NO 1
<211> LENGTH: 638
<212> TYPE: DNA
<213> ORGANISM: Mus musculus

<400> SEQUENCE: 1

```
gcatgccaat ttatagtgcc gtcactaaca gtactgatac tttaacatgc taagtttaaa      60
gtgtgtgcta tattaattgt aagattggtg aagagaggtg ttatcagatg gaagctgcac     120
atttctggat taatgtggtt aaatgtatct tctcctgtga ttactgtctt tatttcttct     180
tttaaaatat tgtcatttgg acatctatct gtatagctac gccctgacac gtcctcctgg     240
agacagataa gaagttacga cgggaggagc agatggaggc aaagcgctgt gatgcttttg     300
tggtttgagt gcacacattt gttcagtgat tctgtgaaat gagtgagcaa atggtgaccg     360
ggtgccctgt aaatggtgtt ctacatctta agagaagaac acggacacta ggtaagtgaa     420
gcttgctgtc actcctctac agcgtcacag agggtcagtc acccttgacc acactgaact     480
agtcgtcacc tttccactct tcctgccaga agagcagaaa tcagactctc tggggatatc     540
agcctcaccc ctactgctct ctccattatg aggcaaactt tctttcactt cccagaggct     600
ctgggggcag caaggtcaac cctttcctca gactctag                             638
```

<210> SEQ ID NO 2
<211> LENGTH: 335
<212> TYPE: DNA
<213> ORGANISM: Mus musculus

<400> SEQUENCE: 2

```
tctcggagga gatcagatcg cgcttattca agggaaccag cccctgctct gcgccctggt      60
```

```
ccaaggctgt tgaagagtga caaaaggcac cacgctgcgg ggacgcgggt gaagcccctc     120
tgtgtgtcct ctgggcataa tcaggaactg gtgccaaatc agaggtgatg tggccagggc     180
tttgggagtg acgcgcggct gggaggcttg cgcacccaag gcacgcccct gccaagtccc     240
actagcagct ctttggagac ctgggccggc tcagccactt cccccagtcc ctcctccggc     300
aaggggctat atagatctcc caggtcaggg cgcag                                335
```

<210> SEQ ID NO 3
<211> LENGTH: 973
<212> TYPE: DNA
<213> ORGANISM: Artificial Sequence
<220> FEATURE:
<223> OTHER INFORMATION: Laboratory-synthesized seqeunce.

<400> SEQUENCE: 3

```
gcatgccaat ttatagtgcc gtcactaaca gtactgatac tttaacatgc taagtttaaa      60
gtgtgtgcta tattaattgt aagattggtg aagagaggtg ttatcagatg gaagctgcac     120
atttctggat taatgtggtt aaatgtatct tctcctgtga ttactgtctt tatttcttct     180
tttaaaatat tgtcatttgg acatctatct gtatagctac gccctgacac gtcctcctgg     240
agacagataa gaagttacga cgggaggagc agatggaggc aaagcgctgt gatgcttttg     300
tggtttgagt gcacacattt gttcagtgat tctgtgaaat gagtgagcaa atggtgaccg     360
ggtgccctgt aaatggtgtt ctacatctta agagaagaac acggacacta ggtaagtgaa     420
gcttgctgtc actcctctac agcgtcacag agggtcagtc cccttgacc acactgaact      480 agtcgtcacc tttccactct tcctgccaga agagcagaaa tcagactctc tggggatatc     540
agcctcaccc ctactgctct ctccattatg aggcaaactt tctttcactt cccagaggct     600
ctgggggcag caaggtcaac cctttcctca gactctagtc tcggaggaga tcagatcgcg     660
cttattcaag ggaaccagcc cctgctctgc gccctggtcc aaggctgttg aagagtgaca     720
aaaggcacca cgctgcgggg acgcgggtga agcccctctg tgtgtcctct gggcataatc     780
aggaactggt gccaaatcag aggtgatgtg gccagggctt tgggagtgac gcgcggctgg     840
gaggcttgcg cacccaaggc acgcccctgc caagtcccac tagcagctct ttggagacct     900
gggccggctc agccacttcc cccagtccct cctccggcaa ggggctatat agatctccca     960
ggtcagggcg cag                                                         973
```

<210> SEQ ID NO 4
<211> LENGTH: 295
<212> TYPE: DNA
<213> ORGANISM: Rattus norvegicus

<400> SEQUENCE: 4

```
gacgtcacag tgggtcagtc acccttgatc acactgcacc agtcttcacc tttccacgct      60
tcctgccaga gcatgaatca ggctctctgg ggataccggc tcacccctca ctgaggcaaa     120
ctttctccca cttctcagag gctctgaggg cagcaaggtc agccctttct tggaatctag     180 aaccactcc ctgtcttgag ctgacatcac agggcaggca gatgcagcag ggaagggcct     240
gggactggga cgttcatcct acaagaaagc tgtggaactt tcagcaaca tctca           295
```

<210> SEQ ID NO 5
<211> LENGTH: 427
<212> TYPE: DNA
<213> ORGANISM: Rattus norvegicus

<400> SEQUENCE: 5

```
gaaatcagat cgcacttatt caaaggagcc aggccctgct ctgcgccctg gtggaggctc    60
ctcatgtgaa gagtgacaaa aggcaccatg ttgtggatac ggggcgaagc ccctccggtg   120
tgtcctccag gcatcatcag gaactagtgc caaagcagag gtgctggcca gggctttggg   180
agtgacgcgc gtctgggagg cttgtgcgcc cagggcacgc ccctgccgat cccactagc    240
aggtcttggg ggacctgggc cggctctgcc cctcctccag caatcgggct ataaagctct   300
tccaagtcag ggcgcagaag tgccgggcga tccgggctta aagagcgaga ggaagggacg   360
ctcacctttg agctcctcca caaatagccc tggtggctgc cacagaagtt cgaagttgag   420
agttcgg                                                            427
```

<210> SEQ ID NO 6
<211> LENGTH: 722
<212> TYPE: DNA
<213> ORGANISM: Artificial Sequence
<220> FEATURE:
<223> OTHER INFORMATION: Laboratory-synthesized seqeunce

<400> SEQUENCE: 6

```
gacgtcacag tgggtcagtc acccttgatc acactgcacc agtcttcacc tttccacgct    60
tcctgccaga gcatgaatca ggctctctgg ggataccggc ctcaccccta ctgaggcaaa   120
cttttctccca cttctcagag gctctgaggg cagcaaggtc agccctttct ttggaatcta   180
gaaccactcc ctgtcttgag ctgacatcac agggcaggca gatgcagcag ggaagggcct   240
gggactggga cgttcatcct acaagaaagc tgtggaactt tcagcaaca tctcagaaat    300
cagatcgcac ttattcaaag gagccaggcc ctgctctgcg ccctggtgga ggctcctcat   360
gtgaagagtg acaaaaggca ccatgttgtg gatacggggc gaagcccctc cggtgtgtcc   420
tccaggcatc atcaggaact agtgccaaag cagaggtgct ggccagggct ttgggagtga   480
cgcgcgtctg ggaggcttgt gcgcccaggg cacgcccctg ccgattccca ctagcaggtc   540
ttgggggacc tgggccggct ctgcccctcc tccagcaatc gggctataaa gctcttccaa   600
gtcagggcgc agaagtgccg ggcgatccgg gcttaaagag cgagaggaag ggacgctcac   660
ctttgagctc ctccacaaat agccctggtg gctgccacag aagttcgaag ttgagagttc   720
gg                                                                 722
```

<210> SEQ ID NO 7
<211> LENGTH: 334
<212> TYPE: DNA
<213> ORGANISM: Homo sapiens

<400> SEQUENCE: 7

```
tgatcaagtg catttgttaa tgtgttctac attttcaaaa aggaaaggag aatttgttac    60
attcagaact tgctgccact cctttgctac gtcataaagg gtcagttgcc cttgctcata   120
ctgacctatt ctttacctct ctgcttcttc tttgtgccag aagagtagaa atctgaccct   180
ttggggatac caccctctcc cctactgctc tctccaacct gaggcaaact ttctcctact   240
tcccagagcc tgtcagaagt ggtgaagcca gcctgctcct tggaatccag aactactttc   300
agaatcttga acttctgtga cctctcaggg tccc                              334
```

<210> SEQ ID NO 8
<211> LENGTH: 289
<212> TYPE: DNA
<213> ORGANISM: Homo sapiens
```

<400> SEQUENCE: 8

```
accgccgcgg tgcgccctcc ctccgacgtg cggtgtgcgg ggcgcagaca accagcggcc      60
ggcccagggc tttcggggag cgaagcaggg ctcccgaggc accgagcgag aatgggaatg     120
ggagggaccc ggtgctcccg gacacgcccc cggcaggtcc cacgcccggg tcttctgaga     180
cctcgcgcgg cccagcccgg gagcggccca gctatataag tcccagcgga agaccggaac     240
gcagagggtc ctgctggcgc gagggtgggt aggagggac gcgggact                    289
```

<210> SEQ ID NO 9
<211> LENGTH: 623
<212> TYPE: DNA
<213> ORGANISM: Homo sapiens

<400> SEQUENCE: 9

```
tgatcaagtg catttgttaa tgtgttctac attttcaaaa aggaaaggag aatttgttac      60
attcagaact tgctgccact cctttgctac gtcataaagg gtcagttgcc cttgctcata     120
ctgacctatt ctttacctct ctgcttcttc tttgtgccag aagagtagaa atctgaccct     180
ttggggatac caccctctcc cctactgctc tctccaacct gaggcaaact ttctcctact     240
tcccagagcc tgtcagaagt ggtgaagcca gcctgctcct tggaatccag aactactttc     300
agaatcttga acttctgtga cctctcaggg tcccaccgcc gcggtgcgcc ctccctccga     360
cgtgcggtgt gcggggcgca gacaaccagc ggccggccca gggctttcgg ggagcgaagc     420
agggctcccg aggcaccgag cgagaatggg aatgggaggg accggtgct cccggacacg      480
cccccggcag gtcccacgcc cgggtcttct gagacctcgc gcggcccagc ccgggagcgg     540
cccagctata taagtcccag cggaagaccg gaacgcagag ggtcctgctg gcgcgagggt     600
gggtaggagg ggacgcgggg act                                              623
```

<210> SEQ ID NO 10
<211> LENGTH: 888
<212> TYPE: DNA
<213> ORGANISM: Homo sapiens

<400> SEQUENCE: 10

```
atgctatttta tgaagatgga cctgttgaac tatcagtact ggacaagat gaacaacaat      60
atcggcattc tgtgctacga aggcgaagct gctctcaggg gagaacccag aatacagacc     120
ctgccggtgg cctctgccct cagcagtcac cgcaccggcc ctcccccaat cagccccagc     180
aagaggaagt tcagcatgga gccaggtgac gaggacctag actgtgacaa cgaccacgtc     240
tccaaaatga gtcgcatctt caaccccat ctgaacaaga ctgccaatgg agactgccgc      300
agagaccccc gggagcggag ccgcagcccc atcgagcgcg ctgtggcccc caccatgagc     360
ctgcacggca gccacctgta cacctccctc cccagccttg gcctggagca gccctcgca      420
ctgaccaaga acagcctgga cgccagcagg ccagccggcc tctcgcccac actgaccccg     480
ggggagcggc agcagaaccg gcctccgtg atcacctgtg cctcggctgg cgcccgcaac     540
tgcaacctct cgcactgccc catcgcgcac agcggctgtg ccgcgccggg cctgccagc     600
taccggaggc caccgagcgc tgccaccacc tgtgaccccg tggtgaggga gcatttccgc     660
aggagcctgg gcaagaatta caaggagccc gagccggcac ccaactccgt gtccatcacg     720
ggctccgtgg acgaccactt tgccaaagct ctgggtgaca cgtggctcca gatcaaagcg     780
gccaaggacg gagcatccag cagccctgag tccgcctctc gcaggggcca gccgccagc      840
```

```
cctctgccc acatggtcag ccacagtcac tccccctctg tggtctcc            888
```

<210> SEQ ID NO 11
<211> LENGTH: 296
<212> TYPE: PRT
<213> ORGANISM: Homo sapiens

<400> SEQUENCE: 11

```
Met Leu Phe Met Lys Met Asp Leu Leu Asn Tyr Gln Tyr Leu Asp Lys
 1               5                  10                  15

Met Asn Asn Asn Ile Gly Ile Leu Cys Tyr Glu Gly Glu Ala Ala Leu
                20                  25                  30

Arg Gly Glu Pro Arg Ile Gln Thr Leu Pro Val Ala Ser Ala Leu Ser
            35                  40                  45

Ser His Arg Thr Gly Pro Pro Ile Ser Pro Ser Lys Arg Lys Phe
        50                  55                  60

Ser Met Glu Pro Gly Asp Glu Leu Asp Cys Asp Asn Asp His Val
 65                 70                  75                  80

Ser Lys Met Ser Arg Ile Phe Asn Pro His Leu Asn Lys Thr Ala Asn
                85                  90                  95

Gly Asp Cys Arg Arg Asp Pro Arg Glu Arg Ser Arg Ser Pro Ile Glu
            100                 105                 110

Arg Ala Val Ala Pro Thr Met Ser Leu His Gly Ser His Leu Tyr Thr
        115                 120                 125

Ser Leu Pro Ser Leu Gly Leu Glu Gln Pro Leu Ala Leu Thr Lys Asn
130                 135                 140

Ser Leu Asp Ala Ser Arg Pro Ala Gly Leu Ser Pro Thr Leu Thr Pro
145                 150                 155                 160

Gly Glu Arg Gln Gln Asn Arg Pro Ser Val Ile Thr Cys Ala Ser Ala
                165                 170                 175

Gly Ala Arg Asn Cys Asn Leu Ser His Cys Pro Ile Ala His Ser Gly
            180                 185                 190

Cys Ala Ala Pro Gly Pro Ala Ser Tyr Arg Arg Pro Pro Ser Ala Ala
        195                 200                 205

Thr Thr Cys Asp Pro Val Val Glu Glu His Phe Arg Arg Ser Leu Gly
    210                 215                 220

Lys Asn Tyr Lys Glu Pro Glu Pro Ala Pro Asn Ser Val Ser Ile Thr
225                 230                 235                 240

Gly Ser Val Asp Asp His Phe Ala Lys Ala Leu Gly Asp Thr Trp Leu
                245                 250                 255

Gln Ile Lys Ala Ala Lys Asp Gly Ala Ser Ser Ser Pro Glu Ser Ala
            260                 265                 270

Ser Arg Arg Gly Gln Pro Ala Ser Pro Ser Ala His Met Val Ser His
        275                 280                 285

Ser His Ser Pro Ser Val Val Ser
    290                 295
```

<210> SEQ ID NO 12
<211> LENGTH: 870
<212> TYPE: DNA
<213> ORGANISM: Homo sapiens

<400> SEQUENCE: 12

```
atggagacgc cattggatgt tttgtccagg gcagcatctc tgtgcatgc tgatgacgaa      60 aaacgcgaag ctgctctcag gggagaaccc agaatacaga ccctgccggt ggcctctgcc     120
```

```
ctcagcagtc accgcaccgg ccctccccca atcagcccca gcaagaggaa gttcagcatg    180
gagccaggtg acgaggacct agactgtgac aacgaccacg tctccaaaat gagtcgcatc    240
ttcaaccccc atctgaacaa gactgccaat ggagactgcc gcagagaccc ccgggagcgg    300
agccgcagcc ccatcgagcg cgctgtggcc cccaccatga gcctgcacgg cagccacctg    360
tacacctccc tccccagcct tggcctggag cagcccctcg cactgaccaa gaacagcctg    420
gacgccagca ggccagccgg cctctcgccc acactgaccc cggggagcgg gcagcagaac    480
cggccctccg tgatcacctg tgcctcggct ggcgcccgca actgcaacct ctcgcactgc    540
cccatcgcgc acagcggctg tgccgcgccc gggcctgcca gctaccggag gccaccgagc    600
gctgccacca cctgtgaccc cgtggtggag gagcatttcc gcaggagcct gggcaagaat    660
tacaaggagc ccgagccggc acccaactcc gtgtccatca cgggctccgt ggacgaccac    720
tttgccaaag ctctgggtga cacgtggctc cagatcaaag cggccaagga cggagcatcc    780
agcagccctg agtccgcctc tcgcaggggc cagcccgcca cccctctgc ccacatggtc     840 agccacagtc actccccctc tgtggtctcc                                      870
```

<210> SEQ ID NO 13
<211> LENGTH: 290
<212> TYPE: PRT
<213> ORGANISM: Homo sapiens

<400> SEQUENCE: 13

```
Met Glu Thr Pro Leu Asp Val Leu Ser Arg Ala Ala Ser Leu Val His
1               5                   10                  15

Ala Asp Asp Glu Lys Arg Glu Ala Ala Leu Arg Gly Glu Pro Arg Ile
            20                  25                  30

Gln Thr Leu Pro Val Ala Ser Ala Leu Ser Ser His Arg Thr Gly Pro
        35                  40                  45

Pro Pro Ile Ser Pro Ser Lys Arg Lys Phe Ser Met Glu Pro Gly Asp
    50                  55                  60

Glu Asp Leu Asp Cys Asp Asn Asp His Val Ser Lys Met Ser Arg Ile
65                  70                  75                  80

Phe Asn Pro His Leu Asn Lys Thr Ala Asn Gly Asp Cys Arg Arg Asp
                85                  90                  95

Pro Arg Glu Arg Ser Arg Ser Pro Ile Glu Arg Ala Val Ala Pro Thr
            100                 105                 110

Met Ser Leu His Gly Ser His Leu Tyr Thr Ser Leu Pro Ser Leu Gly
        115                 120                 125

Leu Glu Gln Pro Leu Ala Leu Thr Lys Asn Ser Leu Asp Ala Ser Arg
    130                 135                 140

Pro Ala Gly Leu Ser Pro Thr Leu Thr Pro Gly Glu Arg Gln Gln Asn
145                 150                 155                 160

Arg Pro Ser Val Ile Thr Cys Ala Ser Ala Gly Ala Arg Asn Cys Asn
                165                 170                 175

Leu Ser His Cys Pro Ile Ala His Ser Gly Cys Ala Ala Pro Gly Pro
            180                 185                 190

Ala Ser Tyr Arg Arg Pro Pro Ser Ala Ala Thr Thr Cys Asp Pro Val
        195                 200                 205

Val Glu Glu His Phe Arg Arg Ser Leu Gly Lys Asn Tyr Lys Glu Pro
    210                 215                 220

Glu Pro Ala Pro Asn Ser Val Ser Ile Thr Gly Ser Val Asp Asp His
225                 230                 235                 240
```

```
Phe Ala Lys Ala Leu Gly Asp Thr Trp Leu Gln Ile Lys Ala Ala Lys
                    245                 250                 255

Asp Gly Ala Ser Ser Ser Pro Glu Ser Ala Ser Arg Arg Gly Gln Pro
            260                 265                 270

Ala Ser Pro Ser Ala His Met Val Ser His Ser His Ser Pro Ser Val
        275                 280                 285

Val Ser
    290

<210> SEQ ID NO 14
<211> LENGTH: 630
<212> TYPE: DNA
<213> ORGANISM: Homo sapiens

<400> SEQUENCE: 14
atgattaaag tgaggaacaa gactgccaat ggagactgcc gcagagaccc ccgggagcgg     60
agccgcagcc ccatcgagcg cgctgtggcc cccaccatga gcctgcacgg cagccacctg    120
tacacctccc tccccagcct tggcctggag cagcccctcg cactgaccaa gaacagcctg    180
gacgccagca ggccagccgg cctctcgccc acactgaccc cggggagcg gcagcagaac     240 cggcccteeg tgatcacctg tgcctcggct ggcgccgca actgcaacct ctcgcactgc     300
cccatcgcgc acagcggctg tgccgcgccc gggcctgcca gctaccggag gccaccgagc    360
gctgccacca cctgtgaccc cgtggtggag agcatttcc gcaggagcct gggcaagaat     420
tacaaggagc ccgagccggc acccaactcc gtgtccatca cgggctccgt ggacgaccac    480
tttgccaaag ctctgggtga cacgtggctc cagatcaaag cggccaagga cggagcatcc    540
agcagccctg agtccgcctc tcgcaggggc cagcccgcca gcccctctgc ccacatggtc    600
agccacagtc actccccctc tgtggtctcc                                      630

<210> SEQ ID NO 15
<211> LENGTH: 210
<212> TYPE: PRT
<213> ORGANISM: Homo sapiens

<400> SEQUENCE: 15

Met Ile Lys Val Arg Asn Lys Thr Ala Asn Gly Asp Cys Arg Arg Asp
1               5                   10                  15

Pro Arg Glu Arg Ser Arg Ser Pro Ile Glu Arg Ala Val Ala Pro Thr
            20                  25                  30

Met Ser Leu His Gly Ser His Leu Tyr Thr Ser Leu Pro Ser Leu Gly
        35                  40                  45

Leu Glu Gln Pro Leu Ala Leu Thr Lys Asn Ser Leu Asp Ala Ser Arg
    50                  55                  60

Pro Ala Gly Leu Ser Pro Thr Leu Thr Pro Gly Glu Arg Gln Gln Asn
65                  70                  75                  80

Arg Pro Ser Val Ile Thr Cys Ala Ser Gly Ala Arg Asn Cys Asn
                85                  90                  95

Leu Ser His Cys Pro Ile Ala His Ser Gly Cys Ala Ala Pro Gly Pro
            100                 105                 110

Ala Ser Tyr Arg Arg Pro Pro Ser Ala Ala Thr Thr Cys Asp Pro Val
        115                 120                 125

Val Glu Glu His Phe Arg Arg Ser Leu Gly Lys Asn Tyr Lys Glu Pro
    130                 135                 140

Glu Pro Ala Pro Asn Ser Val Ser Ile Thr Gly Ser Val Asp Asp His
145                 150                 155                 160
```

```
Phe Ala Lys Ala Leu Gly Asp Thr Trp Leu Gln Ile Lys Ala Ala Lys
                165                 170                 175

Asp Gly Ala Ser Ser Pro Glu Ser Ala Ser Arg Arg Gly Gln Pro
            180                 185                 190

Ala Ser Pro Ser Ala His Met Val Ser His Ser His Ser Pro Ser Val
        195                 200                 205

Val Ser
    210

<210> SEQ ID NO 16
<211> LENGTH: 618
<212> TYPE: DNA
<213> ORGANISM: Homo sapiens

<400> SEQUENCE: 16
atgaacaaga ctgccaatgg agactgccgc agagaccccc gggagcggag ccgcagcccc      60
atcgagcgcg ctgtggcccc caccatgagc ctgcacggca gccacctgta cacctccctc     120
cccagccttg gcctggagca gcccctcgca ctgaccaaga acagcctgga cgccagcagg     180
ccagccggcc tctcgcccac actgaccccg ggggagcggc agcagaaccg gccctccgtg     240
atcacctgtg cctcggctgg cgcccgcaac tgcaacctct cgcactgccc catcgcgcac     300
agcggctgtg ccgcgcccgg gcctgccagc taccggaggc caccgagcgc tgccaccacc     360
tgtgaccccg tggtggagga gcatttccgc aggagcctgg gcaagaatta caaggagccc     420
gagccggcac ccaactccgt gtccatcacg ggctccgtgg acgaccactt tgccaaagct     480
ctgggtgaca cgtggctcca gatcaaagcg gccaaggacg gagcatccag cagccctgag     540
tccgcctctc gcaggggcca gcccgccagc ccctctgccc acatggtcag ccacagtcac     600
tccccctctg tggtctcc                                                   618

<210> SEQ ID NO 17
<211> LENGTH: 206
<212> TYPE: PRT
<213> ORGANISM: Homo sapiens

<400> SEQUENCE: 17

Met Asn Lys Thr Ala Asn Gly Asp Cys Arg Arg Asp Pro Arg Glu Arg
1               5                   10                  15

Ser Arg Ser Pro Ile Glu Arg Ala Val Ala Pro Thr Met Ser Leu His
            20                  25                  30

Gly Ser His Leu Tyr Thr Ser Leu Pro Ser Leu Gly Leu Glu Gln Pro
        35                  40                  45

Leu Ala Leu Thr Lys Asn Ser Leu Asp Ala Ser Arg Pro Ala Gly Leu
    50                  55                  60

Ser Pro Thr Leu Thr Pro Gly Glu Arg Gln Gln Asn Arg Pro Ser Val
65                  70                  75                  80

Ile Thr Cys Ala Ser Ala Gly Ala Arg Asn Cys Asn Leu Ser His Cys
                85                  90                  95

Pro Ile Ala His Ser Gly Cys Ala Ala Pro Gly Pro Ala Ser Tyr Arg
            100                 105                 110

Arg Pro Pro Ser Ala Ala Thr Thr Cys Asp Pro Val Val Glu Glu His
        115                 120                 125

Phe Arg Arg Ser Leu Gly Lys Asn Tyr Lys Glu Pro Glu Pro Ala Pro
    130                 135                 140

Asn Ser Val Ser Ile Thr Gly Ser Val Asp Asp His Phe Ala Lys Ala
```

```
                145                 150                 155                 160
Leu Gly Asp Thr Trp Leu Gln Ile Lys Ala Ala Lys Asp Gly Ala Ser
                    165                 170                 175

Ser Ser Pro Glu Ser Ala Ser Arg Arg Gly Gln Pro Ala Ser Pro Ser
                180                 185                 190

Ala His Met Val Ser His Ser His Ser Pro Ser Val Val Ser
                195                 200                 205

<210> SEQ ID NO 18
<211> LENGTH: 885
<212> TYPE: DNA
<213> ORGANISM: Homo sapiens

<400> SEQUENCE: 18
atgactgaga atacgcattt tgacaaaatc cctgagtcct gtgcactcaa aagttggaga       60
catccaggtc tgcaccatgg cgaagctgct ctcaggggag aacccagaat acagaccctg      120
ccggtggcct ctgccctcag cagtcaccgc accggccctc ccccaatcag ccccagcaag      180
aggaagttca gcatggagcc aggtgacgag gacctagact gtgacaacga ccacgtctcc      240
aaaatgagtc gcatcttcaa ccccatctg aacaagactg ccaatggaga ctgccgcaga       300 gaccccggg agcggagccg cagccccatc gagcgcgctg tggcccccac catgagcctg       360
cacggcagcc acctgtacac ctccctcccc agccttggcc tggagcagcc cctcgcactg      420
accaagaaca gcctggacgc cagcaggcca gccggcctct cgcccacact gaccccgggg      480
gagcggcagc agaaccggcc ctccgtgatc acctgtgcct cggctggcgc cgcaactgc       540 aacctctcgc actgccccat cgcgcacagc ggctgtgccg cgcccgggcc tgccagctac      600
cggaggccac cgagcgctgc caccacctgt gaccccgtgg tggaggagca tttccgcagg      660
agcctgggca agaattacaa ggagcccgag ccggcaccca actccgtgtc catcacgggc      720
tccgtggacg accactttgc caaagctctg ggtgacacgt ggctccagat caaagcggcc      780
aaggacggag catccagcag ccctgagtcc gcctctcgca ggggccagcc cgccagcccc      840
tctgcccaca tggtcagcca cagtcactcc ccctctgtgg tctcc                      885

<210> SEQ ID NO 19
<211> LENGTH: 295
<212> TYPE: PRT
<213> ORGANISM: Homo sapiens

<400> SEQUENCE: 19

Met Thr Glu Asn Thr His Phe Asp Lys Ile Pro Glu Ser Cys Ala Leu
1               5                   10                  15

Lys Ser Trp Arg His Pro Gly Leu His His Gly Glu Ala Ala Leu Arg
                20                  25                  30

Gly Glu Pro Arg Ile Gln Thr Leu Pro Val Ala Ser Ala Leu Ser Ser
            35                  40                  45

His Arg Thr Gly Pro Pro Ile Ser Pro Ser Lys Arg Lys Phe Ser
        50                  55                  60

Met Glu Pro Gly Asp Glu Asp Leu Asp Cys Asp Asn Asp His Val Ser
65                  70                  75                  80

Lys Met Ser Arg Ile Phe Asn Pro His Leu Asn Lys Thr Ala Asn Gly
                85                  90                  95

Asp Cys Arg Arg Asp Pro Arg Glu Arg Ser Arg Ser Pro Ile Glu Arg
            100                 105                 110

Ala Val Ala Pro Thr Met Ser Leu His Gly Ser His Leu Tyr Thr Ser
```

```
              115                 120                 125
Leu Pro Ser Leu Gly Leu Glu Gln Pro Leu Ala Leu Thr Lys Asn Ser
        130                 135                 140

Leu Asp Ala Ser Arg Pro Ala Gly Leu Ser Pro Thr Leu Thr Pro Gly
145                 150                 155                 160

Glu Arg Gln Gln Asn Arg Pro Ser Val Ile Thr Cys Ala Ser Ala Gly
                165                 170                 175

Ala Arg Asn Cys Asn Leu Ser His Cys Pro Ile Ala His Ser Gly Cys
            180                 185                 190

Ala Ala Pro Gly Pro Ala Ser Tyr Arg Arg Pro Pro Ser Ala Ala Thr
        195                 200                 205

Thr Cys Asp Pro Val Val Glu Glu His Phe Arg Arg Ser Leu Gly Lys
    210                 215                 220

Asn Tyr Lys Glu Pro Glu Pro Ala Pro Asn Ser Val Ser Ile Thr Gly
225                 230                 235                 240

Ser Val Asp Asp His Phe Ala Lys Ala Leu Gly Asp Thr Trp Leu Gln
                245                 250                 255

Ile Lys Ala Ala Lys Asp Gly Ala Ser Ser Ser Pro Glu Ser Ala Ser
            260                 265                 270

Arg Arg Gly Gln Pro Ala Ser Pro Ser Ala His Met Val Ser His Ser
        275                 280                 285

His Ser Pro Ser Val Val Ser
        290                 295

<210> SEQ ID NO 20
<211> LENGTH: 693
<212> TYPE: DNA
<213> ORGANISM: Homo sapiens

<400> SEQUENCE: 20
atggagccag gtgacgagga cctagactgt gacaacgacc acgtctccaa aatgagtcgc      60
atcttcaacc cccatctgaa caagactgcc aatggagact gccgcagaga cccccgggag     120
cggagccgca gccccatcga gcgcgctgtg gcccccacca tgagcctgca cggcagccac     180
ctgtacacct ccctccccag ccttggcctg agcagcccc tcgcactgac caagaacagc      240
ctggacgcca gcaggccagc cggcctctcg cccacactga ccccggggga gcggcagcag     300
aaccggccct ccgtgatcac ctgtgcctcg gctggcgccc gcaactgcaa cctctcgcac     360
tgccccatcg cgcacagcgg ctgtgccgcg cccgggcctg ccagctaccg gaggccaccg     420
agcgctgcca ccacctgtga ccccgtggtg gaggagcatt tccgcaggag cctgggcaag     480
aattacaagg agcccgagcc ggcacccaac tccgtgtcca tcacgggctc cgtggacgac     540
cactttgcca agctctgggt gacacgtgg ctccagatca aagcggccaa ggacggagca      600
tccagcagcc ctgagtccgc ctctcgcagg ggccagcccg ccagcccctc tgcccacatg     660
gtcagccaca gtcactcccc ctctgtggtc tcc                                  693

<210> SEQ ID NO 21
<211> LENGTH: 231
<212> TYPE: PRT
<213> ORGANISM: Homo sapiens

<400> SEQUENCE: 21

Met Glu Pro Gly Asp Glu Asp Leu Asp Cys Asp Asn Asp His Val Ser
1               5                   10                  15

Lys Met Ser Arg Ile Phe Asn Pro His Leu Asn Lys Thr Ala Asn Gly
```

|    |    |    |    |    | 20  |    |    |    |    | 25  |    |    |    |    | 30  |    |    |    |
|----|----|----|----|----|----|----|----|----|----|----|----|----|----|----|----|----|----|----|

Asp Cys Arg Arg Asp Pro Arg Glu Arg Ser Arg Ser Pro Ile Glu Arg
            35                  40                45

Ala Val Ala Pro Thr Met Ser Leu His Gly Ser His Leu Tyr Thr Ser
 50                    55               60

Leu Pro Ser Leu Gly Leu Glu Gln Pro Leu Ala Leu Thr Lys Asn Ser
65               70               75               80

Leu Asp Ala Ser Arg Pro Ala Gly Leu Ser Pro Thr Leu Thr Pro Gly
            85               90               95

Glu Arg Gln Gln Asn Arg Pro Ser Val Ile Thr Cys Ala Ser Ala Gly
        100               105              110

Ala Arg Asn Cys Asn Leu Ser His Cys Pro Ile Ala His Ser Gly Cys
        115               120              125

Ala Ala Pro Gly Pro Ala Ser Tyr Arg Arg Pro Ser Ala Ala Thr
      130              135              140

Thr Cys Asp Pro Val Val Glu Glu His Phe Arg Arg Ser Leu Gly Lys
145             150               155             160

Asn Tyr Lys Glu Pro Glu Pro Ala Pro Asn Ser Val Ser Ile Thr Gly
          165             170              175

Ser Val Asp Asp His Phe Ala Lys Ala Leu Gly Asp Thr Trp Leu Gln
        180               185              190

Ile Lys Ala Ala Lys Asp Gly Ala Ser Ser Ser Pro Glu Ser Ala Ser
        195             200              205

Arg Arg Gly Gln Pro Ala Ser Pro Ser Ala His Met Val Ser His Ser
      210              215              220

His Ser Pro Ser Val Val Ser
225             230

<210> SEQ ID NO 22
<211> LENGTH: 888
<212> TYPE: DNA
<213> ORGANISM: Artificial Sequence
<220> FEATURE:
<223> OTHER INFORMATION: Laboratory-synthesized seqeunce

<400> SEQUENCE: 22

```
atgctattta tgaagatgga cctgttgaac tatcagtact tggacaagat gaacaacaat      60
atcggcattc tgtgctacga aggcgaagct gctctcaggg gagaacccag aatacagacc     120
ctgccggtgg cctctgccct cagcagtcac cgcaccggcc ctccccaat cagccccagc      180
aagaggaagt tcagcatgga gccaggtgac gaggacctag actgtgacaa cgaccacgtc     240
tccaaaatga gtcgcatctt caaccccat ctgaacaaga ctgccaatgg agactgccgc      300
agagaccccc gggagcggag ccgcagcccc atcgagcgcg ctgtggcccc caccatgagc     360
ctgcacggca gccacctgta cacctccctc ccagccttg gcctggagca gcccctcgca      420
ctgaccaaga cagcctgga cgccagcagg ccagccggcc tctcgcccac actgaccccg      480
ggggagcggc agcagaaccg gccctccgtg atcacctgtg cctcggctgg cgcccgcaac     540
tgcaacctct cgcactgccc catcgcgcac agcggctgtg ccgcgcccgg gcctgccagc     600
taccggaggc caccgagcgc tgccaccacc tgtgaccccg tggtggagga ggcagcccgc     660
aggagcctgg gcaagaatta caaggagccc gagccggcac ccaactccgt gtccatcacg     720
ggctccgtgg acgacgcagc tgccaaagct ctgggtgaca cgtggctcca gatcaaagcg     780
gccaaggacg gagcatccag cagccctgag tccgcctctc gcaggggcca gcccgccagc     840
``` cctctgccc acatggtcag ccacagtcac tcccctctg tggtctcc         888

<210> SEQ ID NO 23
<211> LENGTH: 296
<212> TYPE: PRT
<213> ORGANISM: Artificial Sequence
<220> FEATURE:
<223> OTHER INFORMATION: Laboratory-synthesized seqeunce

<400> SEQUENCE: 23

```
Met Leu Phe Met Lys Met Asp Leu Leu Asn Tyr Gln Tyr Leu Asp Lys
1               5                   10                  15
Met Asn Asn Ile Gly Ile Leu Cys Tyr Glu Gly Glu Ala Ala Leu
            20                  25                  30
Arg Gly Glu Pro Arg Ile Gln Thr Leu Pro Val Ala Ser Ala Leu Ser
        35                  40                  45
Ser His Arg Thr Gly Pro Pro Ile Ser Pro Ser Lys Arg Lys Phe
    50                  55                  60
Ser Met Glu Pro Gly Asp Glu Leu Asp Cys Asp Asn Asp His Val
65                  70                  75                  80
Ser Lys Met Ser Arg Ile Phe Asn Pro His Leu Asn Lys Thr Ala Asn
                85                  90                  95
Gly Asp Cys Arg Arg Asp Pro Arg Glu Arg Ser Arg Ser Pro Ile Glu
            100                 105                 110
Arg Ala Val Ala Pro Thr Met Ser Leu His Gly Ser His Leu Tyr Thr
        115                 120                 125
Ser Leu Pro Ser Leu Gly Leu Glu Gln Pro Leu Ala Leu Thr Lys Asn
    130                 135                 140
Ser Leu Asp Ala Ser Arg Pro Ala Gly Leu Ser Pro Thr Leu Thr Pro
145                 150                 155                 160
Gly Glu Arg Gln Gln Asn Arg Pro Ser Val Ile Thr Cys Ala Ser Ala
                165                 170                 175
Gly Ala Arg Asn Cys Asn Leu Ser His Cys Pro Ile Ala His Ser Gly
            180                 185                 190
Cys Ala Ala Pro Gly Pro Ala Ser Tyr Arg Arg Pro Pro Ser Ala Ala
        195                 200                 205
Thr Thr Cys Asp Pro Val Val Glu Glu Ala Arg Arg Ser Leu Gly
    210                 215                 220
Lys Asn Tyr Lys Glu Pro Glu Pro Ala Pro Asn Ser Val Ser Ile Thr
225                 230                 235                 240
Gly Ser Val Asp Asp Ala Ala Lys Ala Leu Gly Asp Thr Trp Leu
                245                 250                 255
Gln Ile Lys Ala Ala Lys Asp Gly Ala Ser Ser Ser Pro Glu Ser Ala
            260                 265                 270
Ser Arg Arg Gly Gln Pro Ala Ser Pro Ser Ala His Met Val Ser His
        275                 280                 285
Ser His Ser Pro Ser Val Val Ser
    290                 295
```

<210> SEQ ID NO 24
<211> LENGTH: 870
<212> TYPE: DNA
<213> ORGANISM: Artificial Sequence
<220> FEATURE:
<223> OTHER INFORMATION: Laboratory-synthesized seqeunce

<400> SEQUENCE: 24

```
atggagacgc cattggatgt tttgtccagg gcagcatctc tggtgcatgc tgatgacgaa    60
aaacgcgaag ctgctctcag gggagaaccc agaatacaga ccctgccggt ggcctctgcc   120
ctcagcagtc accgcaccgg ccctccccca atcagcccca gcaagaggaa gttcagcatg   180
gagccaggtg acgaggacct agactgtgac aacgaccacg tctccaaaat gagtcgcatc   240
ttcaacccc atctgaacaa gactgccaat ggagactgcc gcagagaccc ccgggagcgg   300
agccgcagcc ccatcgagcg cgctgtggcc cccaccatga gcctgcacgg cagccacctg   360
tacacctccc tccccagcct tggcctggag cagcccctcg cactgaccaa gaacagcctg   420
gacgccagca ggccagccgg cctctcgccc acactgaccc cggggagcg gcagcagaac    480
cggccctccg tgatcacctg tgcctcggct ggcgcccgca actgcaacct ctcgcactgc   540
cccatcgcgc acagcggctg tgccgcgccc gggcctgcca gctaccggag gccaccgagc   600
gctgccacca cctgtgaccc cgtggtggag gaggcagccc gcaggagcct gggcaagaat   660
tacaaggagc ccgagccggc acccaactcc gtgtccatca cgggctccgt ggacgacgca   720
gctgccaaag ctctgggtga cacgtggctc cagatcaaag cggccaagga cggagcatcc   780
agcagccctg agtccgcctc tcgcaggggc cagcccgcca gcccctctgc ccacatggtc   840
agccacagtc actcccctc tgtggtctcc                                    870
```

<210> SEQ ID NO 25
<211> LENGTH: 290
<212> TYPE: PRT
<213> ORGANISM: Artificial Sequence
<220> FEATURE:
<223> OTHER INFORMATION: Laboratory-synthesized seqeunce

<400> SEQUENCE: 25

```
Met Glu Thr Pro Leu Asp Val Leu Ser Arg Ala Ala Ser Leu Val His
1               5                   10                  15

Ala Asp Asp Glu Lys Arg Glu Ala Ala Leu Arg Gly Glu Pro Arg Ile
            20                  25                  30

Gln Thr Leu Pro Val Ala Ser Ala Leu Ser Ser His Arg Thr Gly Pro
        35                  40                  45

Pro Pro Ile Ser Pro Ser Lys Arg Lys Phe Ser Met Glu Pro Gly Asp
    50                  55                  60

Glu Asp Leu Asp Cys Asp Asn Asp His Val Ser Lys Met Ser Arg Ile
65                  70                  75                  80

Phe Asn Pro His Leu Asn Lys Thr Ala Asn Gly Asp Cys Arg Arg Asp
                85                  90                  95

Pro Arg Glu Arg Ser Arg Ser Pro Ile Glu Arg Ala Val Ala Pro Thr
            100                 105                 110

Met Ser Leu His Gly Ser His Leu Tyr Thr Ser Leu Pro Ser Leu Gly
        115                 120                 125

Leu Glu Gln Pro Leu Ala Leu Thr Lys Asn Ser Leu Asp Ala Ser Arg
    130                 135                 140

Pro Ala Gly Leu Ser Pro Thr Leu Thr Pro Gly Glu Arg Gln Gln Asn
145                 150                 155                 160

Arg Pro Ser Val Ile Thr Cys Ala Ser Ala Gly Ala Arg Asn Cys Asn
                165                 170                 175

Leu Ser His Cys Pro Ile Ala His Ser Gly Cys Ala Ala Pro Gly Pro
            180                 185                 190

Ala Ser Tyr Arg Arg Pro Pro Ser Ala Ala Thr Thr Cys Asp Pro Val
        195                 200                 205
```

```
Val Glu Glu Ala Ala Arg Arg Ser Leu Gly Lys Asn Tyr Lys Glu Pro
    210                 215                 220
Glu Pro Ala Pro Asn Ser Val Ser Ile Thr Gly Ser Val Asp Asp Ala
225                 230                 235                 240
Ala Ala Lys Ala Leu Gly Asp Thr Trp Leu Gln Ile Lys Ala Ala Lys
                245                 250                 255
Asp Gly Ala Ser Ser Pro Glu Ser Ala Ser Arg Arg Gly Gln Pro
                260                 265                 270
Ala Ser Pro Ser Ala His Met Val Ser His Ser His Ser Pro Ser Val
            275                 280                 285
Val Ser
    290

<210> SEQ ID NO 26
<211> LENGTH: 630
<212> TYPE: DNA
<213> ORGANISM: Artificial Sequence
<220> FEATURE:
<223> OTHER INFORMATION: Laboratory-synthesized seqeunce

<400> SEQUENCE: 26
atgattaaag tgaggaacaa gactgccaat ggagactgcc gcagagaccc ccgggagcgg      60
agccgcagcc ccatcgagcg cgctgtggcc cccaccatga gcctgcacgg cagccacctg     120
tacacctccc tccccagcct tggcctggag cagcccctcg cactgaccaa gaacagcctg     180
gacgccagca ggccagccgg cctctcgccc acactgaccc cggggggagcg gcagcagaac     240 cggcccctccg tgatcacctg tgcctcggct ggcgcccgca actgcaacct ctcgcactgc     300
cccatcgcgc acagcggctg tgccgcgccc gggcctgcca gctaccggag gccaccgagc     360
gctgccacca cctgtgaccc cgtggtggag gaggcagccc gcaggagcct gggcaagaat     420
tacaaggagc ccgagccggc acccaactcc gtgtccatca cgggctccgt ggacgacgca     480
gctgccaaag ctctgggtga cacgtggctc cagatcaaag cggccaagga cggagcatcc     540
agcagccctg agtccgcctc tcgcaggggc cagcccgcca gcccctctgc ccacatggtc     600
agccacagtc actccccctc tgtggtctcc                                      630

<210> SEQ ID NO 27
<211> LENGTH: 210
<212> TYPE: PRT
<213> ORGANISM: Artificial Sequence
<220> FEATURE:
<223> OTHER INFORMATION: Laboratory-synthesized seqeunce

<400> SEQUENCE: 27

Met Ile Lys Val Arg Asn Lys Thr Ala Asn Gly Asp Cys Arg Arg Asp
1               5                   10                  15
Pro Arg Glu Arg Ser Arg Ser Pro Ile Glu Arg Ala Val Ala Pro Thr
            20                  25                  30
Met Ser Leu His Gly Ser His Leu Tyr Thr Ser Leu Pro Ser Leu Gly
        35                  40                  45
Leu Glu Gln Pro Leu Ala Leu Thr Lys Asn Ser Leu Asp Ala Ser Arg
    50                  55                  60
Pro Ala Gly Leu Ser Pro Thr Leu Thr Pro Gly Glu Arg Gln Gln Asn
65                  70                  75                  80
Arg Pro Ser Val Ile Thr Cys Ala Ser Ala Gly Ala Arg Asn Cys Asn
                85                  90                  95
Leu Ser His Cys Pro Ile Ala His Ser Gly Cys Ala Ala Pro Gly Pro
```

```
                    100                 105                 110
Ala Ser Tyr Arg Arg Pro Pro Ser Ala Ala Thr Thr Cys Asp Pro Val
            115                 120                 125

Val Glu Glu Ala Ala Arg Arg Ser Leu Gly Lys Asn Tyr Lys Glu Pro
        130                 135                 140

Glu Pro Ala Pro Asn Ser Val Ser Ile Thr Gly Ser Val Asp Asp Ala
145                 150                 155                 160

Ala Ala Lys Ala Leu Gly Asp Thr Trp Leu Gln Ile Lys Ala Ala Lys
                165                 170                 175

Asp Gly Ala Ser Ser Ser Pro Glu Ser Ala Ser Arg Arg Gly Gln Pro
            180                 185                 190

Ala Ser Pro Ser Ala His Met Val Ser His Ser His Ser Pro Ser Val
        195                 200                 205

Val Ser
    210

<210> SEQ ID NO 28
<211> LENGTH: 618
<212> TYPE: DNA
<213> ORGANISM: Artificial Sequence
<220> FEATURE:
<223> OTHER INFORMATION: Laboratory-synthesized seqeunce

<400> SEQUENCE: 28
atgaacaaga ctgccaatgg agactgccgc agagaccccc gggagcggag ccgcagcccc      60
atcgagcgcg ctgtggcccc caccatgagc ctgcacggca gccacctgta caccctccct     120
cccagccttg gcctggagca gccccgca ctgaccaaga acagcctgga cgccagcagg       180
ccagccggcc tctcgcccac actgaccccg ggggagcggc agcagaaccg gccctccgtg     240
atcacctgtg cctcggctgg cgcccgcaac tgcaacctct cgcactgccc catcgcgcac     300
agcggctgtg ccgcgcccgg cctgccagc taccggaggc caccgagcgc tgccaccacc      360
tgtgaccccg tggtggagga ggcagcccgc aggagcctgg gcaagaatta caaggagccc     420
gagccggcac ccaactccgt gtccatcacg ggctccgtgg acgacgcagc tgccaaagct     480
ctgggtgaca cgtggctcca gatcaaagcg gccaaggacg gagcatccag cagccctgag    540
tccgcctctc gcaggggcca gcccgccagc ccctctgccc acatggtcag ccacagtcac    600 tcccctctg tggtctcc                                                   618

<210> SEQ ID NO 29
<211> LENGTH: 206
<212> TYPE: PRT
<213> ORGANISM: Artificial Sequence
<220> FEATURE:
<223> OTHER INFORMATION: Laboratory-synthesized seqeunce

<400> SEQUENCE: 29

Met Asn Lys Thr Ala Asn Gly Asp Cys Arg Arg Asp Pro Arg Glu Arg
1               5                   10                  15

Ser Arg Ser Pro Ile Glu Arg Ala Val Ala Pro Thr Met Ser Leu His
            20                  25                  30

Gly Ser His Leu Tyr Thr Ser Leu Pro Ser Leu Gly Leu Glu Gln Pro
        35                  40                  45

Leu Ala Leu Thr Lys Asn Ser Leu Asp Ala Ser Arg Pro Ala Gly Leu
    50                  55                  60

Ser Pro Thr Leu Thr Pro Gly Glu Arg Gln Gln Asn Arg Pro Ser Val
65                  70                  75                  80
```

Ile Thr Cys Ala Ser Ala Gly Ala Arg Asn Cys Asn Leu Ser His Cys
            85                  90                  95

Pro Ile Ala His Ser Gly Cys Ala Ala Pro Gly Pro Ala Ser Tyr Arg
            100                 105                 110

Arg Pro Pro Ser Ala Ala Thr Thr Cys Asp Pro Val Val Glu Glu Ala
            115                 120                 125

Ala Arg Arg Ser Leu Gly Lys Asn Tyr Lys Glu Pro Glu Pro Ala Pro
            130                 135                 140
145

Leu Gly Asp Thr Trp Leu Gln Ile Lys Ala Ala Lys Asp Gly Ala Ser
            165                 170                 175

Ser Ser Pro Glu Ser Ala Ser Arg Arg Gly Gln Pro Ala Ser Pro Ser
            180                 185                 190

Ala His Met Val Ser His Ser His Ser Pro Ser Val Val Ser
            195                 200                 205

Asn Ser Val Ser Ile Thr Gly Ser Val Asp Ala Ala Ala Lys Ala
                150                 155                 160

<210> SEQ ID NO 30
<211> LENGTH: 885
<212> TYPE: DNA
<213> ORGANISM: Artificial Sequence
<220> FEATURE:
<223> OTHER INFORMATION: Laboratory-synthesized seqeunce

<400> SEQUENCE: 30
atgactgaga atacgcattt tgacaaaatc cctgagtcct gtgcactcaa aagttggaga    60
catccaggtc tgcaccatgg cgaagctgct ctcaggggag aacccagaat acagaccctg   120
ccggtggcct ctgccctcag cagtcaccgc accggccctc ccccaatcag ccccagcaag   180
aggaagttca gcatggagcc aggtgacgag gacctagact gtgacaacga ccacgtctcc   240
aaaatgagtc gcatcttcaa ccccccatctg aacaagactg ccaatggaga ctgccgcaga   300
gaccccgggg agcggagccg cagccccatc gagcgcgctg tggcccccac catgagcctg   360
cacggcagcc acctgtacac ctccctcccc agccttggcc tggagcagcc cctcgcactg   420
accaagaaca gcctggacgc cagcaggcca gccggcctct cgcccacact gaccccgggg   480
gagcggcagc agaaccggcc ctccgtgatc acctgtgcct cggctggcgc ccgcaactgc   540
aacctctcgc actgccccat cgcgcacagc ggctgtgccg cgcccgggcc tgccagctac   600
cggaggccac cgagcgctgc caccacctgt gaccccgtgg tggaggaggc agcccgcagg   660
agcctgggca gaattacaa ggagcccgag ccggcaccca ctccgtgtc catcacgggc   720
tccgtggacg acgcagctgc caaagctctg ggtgacacgt ggctccagat caaagcggcc   780
aaggacggag catccagcag ccctgagtcc gcctctcgca ggggccagcc cgccagcccc   840
tctgcccaca tggtcagcca cagtcactcc ccctctgtgg tctcc                   885

<210> SEQ ID NO 31
<211> LENGTH: 295
<212> TYPE: PRT
<213> ORGANISM: Artificial Sequence
<220> FEATURE:
<223> OTHER INFORMATION: Laboratory-synthesized seqeunce

<400> SEQUENCE: 31

Met Thr Glu Asn Thr His Phe Asp Lys Ile Pro Glu Ser Cys Ala Leu
1               5                   10                  15

Lys Ser Trp Arg His Pro Gly Leu His His Gly Glu Ala Ala Leu Arg

```
                20                  25                  30
Gly Glu Pro Arg Ile Gln Thr Leu Pro Val Ala Ser Ala Leu Ser Ser
             35                  40                  45

His Arg Thr Gly Pro Pro Ile Ser Pro Ser Lys Arg Lys Phe Ser
 50                  55                  60

Met Glu Pro Gly Asp Glu Asp Leu Asp Cys Asp Asn Asp His Val Ser
 65                  70                  75                  80

Lys Met Ser Arg Ile Phe Asn Pro His Leu Asn Lys Thr Ala Asn Gly
                 85                  90                  95

Asp Cys Arg Arg Asp Pro Arg Glu Arg Ser Arg Ser Pro Ile Glu Arg
            100                 105                 110

Ala Val Ala Pro Thr Met Ser Leu His Gly Ser His Leu Tyr Thr Ser
            115                 120                 125

Leu Pro Ser Leu Gly Leu Glu Gln Pro Leu Ala Leu Thr Lys Asn Ser
        130                 135                 140

Leu Asp Ala Ser Arg Pro Ala Gly Leu Ser Pro Thr Leu Thr Pro Gly
145                 150                 155                 160

Glu Arg Gln Gln Asn Arg Pro Ser Val Ile Thr Cys Ala Ser Ala Gly
                165                 170                 175

Ala Arg Asn Cys Asn Leu Ser His Cys Pro Ile Ala His Ser Gly Cys
            180                 185                 190

Ala Ala Pro Gly Pro Ala Ser Tyr Arg Arg Pro Pro Ser Ala Ala Thr
        195                 200                 205

Thr Cys Asp Pro Val Val Glu Glu Ala Ala Arg Arg Ser Leu Gly Lys
210                 215                 220

Asn Tyr Lys Glu Pro Glu Pro Ala Pro Asn Ser Val Ser Ile Thr Gly
225                 230                 235                 240

Ser Val Asp Asp Ala Ala Lys Ala Leu Gly Asp Thr Trp Leu Gln
                245                 250                 255

Ile Lys Ala Ala Lys Asp Gly Ala Ser Ser Ser Pro Glu Ser Ala Ser
            260                 265                 270

Arg Arg Gly Gln Pro Ala Ser Pro Ser Ala His Met Val Ser His Ser
        275                 280                 285

His Ser Pro Ser Val Val Ser
        290                 295

<210> SEQ ID NO 32
<211> LENGTH: 693
<212> TYPE: DNA
<213> ORGANISM: Artificial Sequence
<220> FEATURE:
<223> OTHER INFORMATION: Laboratory-synthesized seqeunce

<400> SEQUENCE: 32
atggagccag gtgacgagga cctagactgt gacaacgacc acgtctccaa atgagtcgc      60 atcttcaacc ccatctgaa caagactgcc aatggagact gccgcagaga cccccgggag     120
cggagccgca gccccatcga gcgcgctgtg gccccacca tgagcctgca cggcagccac     180
ctgtacacct ccctcccag ccttggcctg gagcagcccc tcgcactgac caagaacagc     240
ctggacgcca gcaggccagc cggcctctcg cccacactga ccccggggga gcggcagcag     300
aaccggccct ccgtgatcac ctgtgcctcg gctggcgccc gcaactgcaa cctctcgcac     360
tgccccatcg cgcacagcgg ctgtgccgcg cccgggcctg ccagctaccg gaggccaccg     420
agcgctgcca ccacctgtga cccgtggtg gaggaggcag cccgcaggag cctgggcaag     480
```

```
aattacaagg agcccgagcc ggcacccaac tccgtgtcca tcacgggctc cgtggacgac    540
gcagctgcca aagctctggg tgacacgtgg ctccagatca aagcggccaa ggacggagca    600
tccagcagcc ctgagtccgc ctctcgcagg ggccagcccg ccagcccctc tgcccacatg    660
gtcagccaca gtcactcccc ctctgtggtc tcc                                693
```

<210> SEQ ID NO 33
<211> LENGTH: 231
<212> TYPE: PRT
<213> ORGANISM: Artificial Sequence
<220> FEATURE:
<223> OTHER INFORMATION: Laboratory-synthesized seqeunce

<400> SEQUENCE: 33

```
Met Glu Pro Gly Asp Glu Asp Leu Asp Cys Asp Asn Asp His Val Ser
1               5                   10                  15

Lys Met Ser Arg Ile Phe Asn Pro His Leu Asn Lys Thr Ala Asn Gly
            20                  25                  30

Asp Cys Arg Arg Asp Pro Arg Glu Arg Ser Arg Ser Pro Ile Glu Arg
        35                  40                  45

Ala Val Ala Pro Thr Met Ser Leu His Gly Ser His Leu Tyr Thr Ser
50                  55                  60

Leu Pro Ser Leu Gly Leu Glu Gln Pro Leu Ala Leu Thr Lys Asn Ser
65                  70                  75                  80

Leu Asp Ala Ser Arg Pro Ala Gly Leu Ser Pro Thr Leu Thr Pro Gly
                85                  90                  95

Glu Arg Gln Gln Asn Arg Pro Ser Val Ile Thr Cys Ala Ser Ala Gly
            100                 105                 110

Ala Arg Asn Cys Asn Leu Ser His Cys Pro Ile Ala His Ser Gly Cys
        115                 120                 125

Ala Ala Pro Gly Pro Ala Ser Tyr Arg Arg Pro Pro Ser Ala Ala Thr
130                 135                 140

Thr Cys Asp Pro Val Val Glu Glu Ala Ala Arg Arg Ser Leu Gly Lys
145                 150                 155                 160

Asn Tyr Lys Glu Pro Glu Pro Ala Pro Asn Ser Val Ser Ile Thr Gly
                165                 170                 175

Ser Val Asp Asp Ala Ala Ala Lys Ala Leu Gly Asp Thr Trp Leu Gln
            180                 185                 190

Ile Lys Ala Ala Lys Asp Gly Ala Ser Ser Pro Glu Ser Ala Ser
        195                 200                 205

Arg Arg Gly Gln Pro Ala Ser Pro Ser Ala His Met Val Ser His Ser
    210                 215                 220

His Ser Pro Ser Val Val Ser
225                 230
```

<210> SEQ ID NO 34
<211> LENGTH: 133
<212> TYPE: DNA
<213> ORGANISM: Artificial Sequence
<220> FEATURE:
<223> OTHER INFORMATION: Laboratory-synthesized seqeunce

<400> SEQUENCE: 34

```
gtaagtatca aggttacaag acaggtttaa ggagaccaat agaaactggg cttgtcgaga    60
cagagaagac tcttgcgttt ctgataggca cctattggtc ttactgacat ccactttgcc    120
tttctctcca cag                                                      133
```

<210> SEQ ID NO 35
<211> LENGTH: 2096
<212> TYPE: DNA
<213> ORGANISM: Artificial Sequence
<220> FEATURE:
<223> OTHER INFORMATION: Laboratory-synthesized seqeunce

<400> SEQUENCE: 35

| | | | | | |
|---|---|---|---|---|---|
| gcatgccaat | ttatagtgcc | gtcactaaca | gtactgatac | tttaacatgc | taagtttaaa | 60 |
| gtgtgtgcta | tattaattgt | aagattggtg | aagagaggtg | ttatcagatg | gaagctgcac | 120 |
| atttctggat | taatgtggtt | aaatgtatct | tctcctgtga | ttactgtctt | tatttcttct | 180 |
| tttaaaatat | tgtcatttgg | acatctatct | gtatagctac | gccctgacac | gtcctcctgg | 240 |
| agacagataa | gaagttacga | cgggaggagc | agatggaggc | aaagcgctgt | gatgcttttg | 300 |
| tggtttgagt | gcacacattt | gttcagtgat | tctgtgaaat | gagtgagcaa | atggtgaccg | 360 |
| ggtgccctgt | aaatggtgtt | ctacatctta | agagaagaac | acggacacta | ggtaagtgaa | 420 |
| gcttgctgtc | actcctctac | agcgtcacag | agggtcagtc | acccttgacc | acactgaact | 480 |
| agtcgtcacc | tttccactct | tcctgccaga | agagcagaaa | tcagactctc | tggggatatc | 540 |
| agcctcaccc | ctactgctct | ctccattatg | aggcaaactt | tctttcactt | cccagaggct | 600 |
| ctggggcag | caaggtcaac | cctttcctca | gactctagtc | tcggaggaga | tcagatcgcg | 660 |
| cttattcaag | gaaccagcc | cctgctctgc | gccctggtcc | aaggctgttg | aagagtgaca | 720 |
| aaaggcacca | cgctgcgggg | acgcgggtga | agcccctctg | tgtgtcctct | gggcataatc | 780 |
| aggaactggt | gccaaatcag | aggtgatgtg | gccaggggctt | tgggagtgac | gcgcggctgg | 840 |
| gaggcttgcg | cacccaaggc | acgcccctgc | caagtcccac | tagcagctct | ttggagacct | 900 |
| gggccggctc | agccacttcc | cccagtccct | cctccggcaa | ggggctatat | agatctccca | 960 |
| ggtcagggcg | cagctgcaga | agttggtcgt | gaggcactgg | gcaggtaagt | atcaaggtta | 1020 |
| caagacaggt | ttaaggagac | caatagaaac | tgggcttgtc | gagacagaga | agactcttgc | 1080 |
| gtttctgata | ggcacctatt | ggtcttactg | acatccactt | tgcctttctc | tccacaggtg | 1140 |
| tccactccca | gttcaattac | agctcttaag | gctagagtac | ttaatacgac | tcactatagg | 1200 |
| ctagcatgct | atttatgaag | atggacctgt | tgaactatca | gtacttggac | aagatgaaca | 1260 |
| acaatatcgg | cattctgtgc | tacgaaggcg | aagctgctct | cagggagaa | cccagaatgc | 1320 |
| agaccctgcc | ggtggcctct | gccctcagca | gtcaccgcac | cggccctccc | ccaatcagcc | 1380 |
| ccagcaagag | gaagttcagc | atggagccag | gtgacgagga | cctagactgt | gacaacgacc | 1440 |
| acgtctccaa | aatgagtcgc | atcttcaacc | cccatctgaa | caagactgcc | aatggagact | 1500 |
| gccgcagaga | cccccgggag | cggagccgca | gccccatcga | gcgcgctgtg | gcccccacca | 1560 |
| tgagcctgca | cggcagccac | ctgtacacct | ccctcccag | ccttggcctg | gagcagcccc | 1620 |
| tcgcactgac | caagaacagc | ctggacgcca | gcaggccagc | cggcctctcg | cccacactga | 1680 |
| cccccgggga | gcggcagcag | aaccggccct | ccgtgatcac | ctgtgcctcg | gctgcgccc | 1740 |
| gcaactgcaa | cctctcgcac | tgccccatcg | cgcacagcgg | ctgtgccgcg | cccgggcctg | 1800 |
| ccagctaccg | gaggccaccg | agcgctgcca | ccacctgtga | ccccgtggtg | gaggagcatt | 1860 |
| tccgcaggag | cctgggcaag | aattacaagg | agcccgagcc | ggcacccaac | tccgtgtcca | 1920 |
| tcacgggctc | cgtggacgac | cactttgcca | aagctctggg | tgacacgtgg | ctccagatca | 1980 |
| aagcggccaa | ggacggagca | tccagcagcc | ctgagtccgc | ctctcgcagg | ggccagcccg | 2040 |
| ccagcccctc | tgcccacatg | gtcagccaca | gtcactcccc | ctctgtggtc | tccgcc | 2096 |

<210> SEQ ID NO 36
<211> LENGTH: 2096
<212> TYPE: DNA
<213> ORGANISM: Artificial Sequence
<220> FEATURE:
<223> OTHER INFORMATION: Laboratory-synthesized seqeunce

<400> SEQUENCE: 36

| | | | | | |
|---|---|---|---|---|---|
| gcatgccaat | ttatagtgcc | gtcactaaca | gtactgatac | tttaacatgc | taagtttaaa | 60 |
| gtgtgtgcta | tattaattgt | aagattggtg | aagagaggtg | ttatcagatg | gaagctgcag | 120 |
| cagcctggat | taatgtggtt | aaatgtatct | tctcctgtga | ttactgtctt | tatttcttct | 180 |
| tttaaaatat | tgtcatttgg | acatctatct | gtatagctac | gccctgacac | gtcctcctgg | 240 |
| agacagataa | gaagttacga | cgggaggagc | agatggaggc | aaagcgctgt | gatgcttttg | 300 |
| tggtttgagt | gcacacattt | gttcagtgat | tctgtgaaat | gagtgagcaa | atggtgaccg | 360 |
| ggtgccctgt | aaatggtgtt | ctacatctta | agagaagaac | acggacacta | ggtaagtgaa | 420 |
| gcttgctgtc | actcctctac | agcgtcacag | agggtcagtc | acccttgacc | acactgaact | 480 |
| agtcgtcacc | tttccactct | tcctgccaga | agagcagaaa | tcagactctc | tggggatatc | 540 |
| agcctcaccc | ctactgctct | ctccattatg | aggcaaactt | tctttcactt | cccagaggct | 600 |
| ctggggcag | caaggtcaac | cctttcctca | gactctagtc | tcggaggaga | tcagatcgcg | 660 |
| cttattcaag | ggaaccagcc | cctgctctgc | gccctggtcc | aaggctgttg | aagagtgaca | 720 |
| aaaggcacca | cgctgcgggg | acgcgggtga | agcccctctg | tgtgtcctct | gggcataatc | 780 |
| aggaactggt | gccaaatcag | aggtgatgtg | gccagggctt | tgggagtgac | gcgcggctgg | 840 |
| gaggcttgcg | cacccaaggc | acgccctgc | caagtccac | tagcagctct | ttggagacct | 900 |
| gggccggctc | agccacttcc | cccagtccct | cctccggcaa | ggggctatat | agatctccca | 960 |
| ggtcagggcg | cagctgcaga | agttggtcgt | gaggcactgg | gcaggtaagt | atcaaggtta | 1020 |
| caagacaggt | ttaaggagac | caatagaaac | tgggcttgtc | gagacagaga | agactcttgc | 1080 |
| gtttctgata | ggcacctatt | ggtcttactg | acatcgcagc | tgcctttctc | tccacaggtg | 1140 |
| tccactccca | gttcaattac | agctcttaag | gctagagtac | ttaatacgac | tcactatagg | 1200 |
| ctagcatgct | atttatgaag | atggacctgt | tgaactatca | gtacttggac | aagatgaaca | 1260 |
| acaatatcgg | cattctgtgc | tacgaaggcg | aagctgctct | caggggagaa | cccagaatgc | 1320 |
| agaccctgcc | ggtggcctct | gccctcagca | gtcaccgcac | cggccctccc | ccaatcagcc | 1380 |
| ccagcaagag | gaagttcagc | atggagccag | gtgacgagga | cctagactgt | gacaacgacc | 1440 |
| acgtctccaa | aatgagtcgc | atcttcaacc | cccatctgaa | caagactgcc | aatggagact | 1500 |
| gccgcagaga | ccccgggag | cggagccgca | gccccatcga | gcgcgctgtg | gcccccacca | 1560 |
| tgagcctgca | cggcagccac | ctgtacacct | ccctccccag | ccttggcctg | gagcagcccc | 1620 |
| tcgcactgac | caagaacagc | ctggacgcca | gcaggccagc | cggcctctcg | cccacactga | 1680 |
| ccccgggga | gcggcagcag | aaccggccct | ccgtgatcac | ctgtgcctcg | gctggcgccc | 1740 |
| gcaactgcaa | cctctcgcac | tgccccatcg | cgcacagcgg | ctgtgccgcg | cccgggcctg | 1800 |
| ccagctaccg | gaggccaccg | agcgctgcca | ccacctgtga | ccccgtggtg | gaggaggcag | 1860 |
| cccgcaggag | cctgggcaag | aattacaagg | agcccgagcc | ggcacccaac | tccgtgtcca | 1920 |
| tcacgggctc | cgtggacgac | gcagctgcca | aagctctggg | tgacacgtgg | ctccagatca | 1980 |
| aagcggccaa | ggacggagca | tccagcagcc | ctgagtccgc | ctctcgcagg | ggccagcccg | 2040 | ccagccccct tgcccacatg gtcagccaca gtcactcccc ctctgtggtc tccgcc          2096

<210> SEQ ID NO 37
<211> LENGTH: 239
<212> TYPE: PRT
<213> ORGANISM: Artificial Sequence
<220> FEATURE:
<223> OTHER INFORMATION: Laboratory-synthesized seqeunce

<400> SEQUENCE: 37

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 38
<211> LENGTH: 720
<212> TYPE: DNA
<213> ORGANISM: Artificial Sequence
<220> FEATURE:
<223> OTHER INFORMATION: Laboratory-synthesized seqeunce

<400> SEQUENCE: 38
atggtgagca agggcgagga gctgttcacc ggggtggtgc ccatcctggt cgagctggac          60
ggcgacgtaa acggccacaa gttcagcgtg tccggcgagg gcgagggcga tgccacctac         120
ggcaagctga ccctgaagtt catctgcacc accggcaagc tgcccgtgcc ctggcccacc         180
ctcgtgacca ccctgaccta cggcgtgcag tgcttcagcc gctaccccga ccacatgaag         240
cagcacgact tcttcaagtc cgccatgccc gaaggctacg tccaggagcg caccatcttc         300
ttcaaggacg acggcaacta caagacccgc gccgaggtga agttcgaggg cgacaccctg         360

| | |
|---|---|
| gtgaaccgca tcgagctgaa gggcatcgac ttcaaggagg acggcaacat cctgggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaagtaa | 720 |

<210> SEQ ID NO 39
<211> LENGTH: 2816
<212> TYPE: DNA
<213> ORGANISM: Artificial Sequence
<220> FEATURE:
<223> OTHER INFORMATION: Laboratory-synthesized seqeunce

<400> SEQUENCE: 39

| | |
|---|---|
| gcatgccaat ttatagtgcc gtcactaaca gtactgatac tttaacatgc taagtttaaa | 60 |
| gtgtgtgcta tattaattgt aagattggtg aagagaggtg ttatcagatg gaagctgcac | 120 |
| atttctggat taatgtggtt aaatgtatct tctcctgtga ttactgtctt tatttcttct | 180 |
| tttaaaatat tgtcatttgg acatctatct gtatagctac gccctgacac gtcctcctgg | 240 |
| agacagataa gaagttacga cgggaggagc agatggaggc aaagcgctgt gatgcttttg | 300 |
| tggtttgagt gcacacattt gttcagtgat tctgtgaaat gagtgagcaa atggtgaccg | 360 |
| ggtgccctgt aaatggtgtt ctacatctta agagaagaac acggacacta ggtaagtgaa | 420 |
| gcttgctgtc actcctctac agcgtcacag agggtcagtc acccttgacc acactgaact | 480 |
| agtcgtcacc tttccactct tcctgccaga agagcagaaa tcagactctc tggggatatc | 540 |
| agcctcaccc ctactgctct ctccattatg aggcaaactt tctttcactt cccagaggct | 600 |
| ctgggggcag caaggtcaac cctttcctca gactctagtc tcggaggaga tcagatcgcg | 660 |
| cttattcaag ggaaccagcc cctgctctgc gccctggtcc aaggctgttg aagagtgaca | 720 |
| aaaggcacca cgctgcgggg acgcgggtga agcccctctg tgtgtcctct gggcataatc | 780 |
| aggaactggt gccaaatcag aggtgatgtg ccaggggctt tgggagtgac gcgcggctgg | 840 |
| gaggcttgcg cacccaaggc acgcccctgc caagtcccac tagcagctct ttggagacct | 900 |
| gggccggctc agccacttcc cccagtccct cctccggcaa ggggctatat agatctccca | 960 |
| ggtcagggcg cagctgcaga agttggtcgt gaggcactgg gcaggtaagt atcaaggtta | 1020 |
| caagacaggt ttaaggagac caatagaaac tgggcttgtc gagacagaga agactcttgc | 1080 |
| gtttctgata ggcacctatt ggtcttactg acatccactt tgcctttctc tccacaggtg | 1140 |
| tccactccca gttcaattac agctcttaag gctagagtac ttaatacgac tcactatagg | 1200 |
| ctagcatgct atttatgaag atggacctgt tgaactatca gtacttggac aagatgaaca | 1260 |
| acaatatcgg cattcgtgc tacgaaggcg aagctgctct caggggagaa cccagaatgc | 1320 |
| agaccctgcc ggtggcctct gccctcagca gtcaccgcac cggccctccc ccaatcagcc | 1380 |
| ccagcaagag gaagttcagc atggagccag gtgacgagga cctagactgt gacaacgacc | 1440 |
| acgtctccaa aatgagtcgc atcttcaacc cccatctgaa caagactgcc aatgagact | 1500 |
| gccgcagaga ccccgggag cggagccgca gcccatcga gcgcgctgtg gcccccacca | 1560 |
| tgagcctgca cggcagccac ctgtacacct ccctccccag ccttggcctg gagcagcccc | 1620 |
| tcgcactgac caagaacagc ctggacgcca gcaggccagc cggcctctcg cccacactga | 1680 |
| ccccggggga gcggcagcag aaccggccct ccgtgatcac ctgtgcctcg ctggcgccc | 1740 |

```
gcaactgcaa cctctcgcac tgccccatcg cgcacagcgg ctgtgccgcg cccgggcctg    1800
ccagctaccg gaggccaccg agcgctgcca ccacctgtga ccccgtggtg gaggagcatt    1860
tccgcaggag cctgggcaag aattacaagg agcccgagcc ggcacccaac tccgtgtcca    1920
tcacgggctc cgtggacgac cactttgcca aagctctggg tgacacgtgg ctccagatca    1980
aagcggccaa ggacggagca tccagcagcc ctgagtccgc ctctcgcagg ggccagcccg    2040
ccagcccctc tgcccacatg gtcagccaca gtcactcccc ctctgtggtc tccgccatgg    2100
tgagcaaggg cgaggagctg ttcaccgggg tggtgcccat cctggtcgag ctggacggcg    2160
acgtaaacgg ccacaagttc agcgtgtccg gcgagggcga gggcgatgcc acctacggca    2220
agctgaccct gaagttcatc tgcaccaccg gcaagctgcc cgtgccctgg cccacccctcg   2280 tgaccaccct gacctacggc gtgcagtgct tcagccgcta ccccgaccac atgaagcagc    2340
acgacttctt caagtccgcc atgcccgaag ctacgtcca ggagcgcacc atcttcttca     2400
aggacgacgg caactacaag acccgcgccg aggtgaagtt cgaggcgac accctggtga     2460 accgcatcga gctgaagggc atcgacttca aggaggacgg caacatcctg ggcacaagc     2520 tggagtacaa ctacaacagc cacaacgtct atatcatggc cgacaagcag aagaacggca    2580
tcaaggtgaa cttcaagatc cgccacaaca tcgaggacgg cagcgtgcag ctcgccgacc    2640
actaccagca gaacaccccc atcggcgacg gccccgtgct gctgcccgac aaccactacc    2700
tgagcaccca gtccgccctg agcaaagacc ccaacgagaa gcgcgatcac atggtcctgc    2760
tggagttcgt gaccgccgcc gggatcactc tcggcatgga cgagctgtac aagtaa        2816
```

<210> SEQ ID NO 40
<211> LENGTH: 2816
<212> TYPE: DNA
<213> ORGANISM: Artificial Sequence
<220> FEATURE:
<223> OTHER INFORMATION: Laboratory-synthesized seqeunce

<400> SEQUENCE: 40

```
gcatgccaat ttatagtgcc gtcactaaca gtactgatac tttaacatgc taagtttaaa     60
gtgtgtgcta tattaattgt aagattggtg aagagaggtg ttatcagatg gaagctgcag    120
cagcctggat taatgtggtt aaatgtatct tctcctgtga ttactgtctt tatttcttct    180
tttaaaatat tgtcatttgg acatctatct gtatagctac gccctgacac gtcctcctgg    240
agacagataa gaagttacga cgggaggagc agatggaggc aaagcgctgt gatgcttttg    300
tggtttgagt gcacacattt gttcagtgat tctgtgaaat gagtgagcaa atggtgaccg    360
ggtgccctgt aaatggtgtt ctacatctta agagaagaac acggacacta ggtaagtgaa    420
gcttgctgtc actcctctac agcgtcacag agggtcagtc acccttgacc acactgaact    480
agtcgtcacc tttccactct tcctgccaga agagcagaaa tcagactctc tggggatatc    540
agcctcaccc ctactgctct ctccattatg aggcaaactt tctttcactt cccagaggct    600 ctggggggcag caaggtcaac ccttttcctca gactctagtc tcggaggaga tcagatcgcg    660
cttattcaag ggaaccagcc cctgctctgc gccctggtcc aaggctgttg aagagtgaca    720
aaaggcacca cgctgcgggg acgcgggtga agcccctctg tgtgtcctct gggcataatc    780
aggaactggt gccaaatcag aggtgatgtg gccagggctt tggagtgac gcgcggctgg    840 gaggcttgcg cacccaaggc acgccctgc caagtcccac tagcagctct ttggagacct     900
gggccggctc agccacttcc cccagtccct cctccggcaa ggggctatat agatctccca    960
```

-continued

```
ggtcagggcg cagctgcaga agttggtcgt gaggcactgg gcaggtaagt atcaaggtta    1020
caagacaggt ttaaggagac aatagaaac tgggcttgtc gagacagaga agactcttgc     1080
gtttctgata ggcacctatt ggtcttactg acatcgcagc tgcctttctc tccacaggtg    1140
tccactccca gttcaattac agctcttaag gctagagtac ttaatacgac tcactatagg    1200
ctagcatgct atttatgaag atggacctgt tgaactatca gtacttggac aagatgaaca    1260
acaatatcgg cattctgtgc tacgaaggcg aagctgctct caggggagaa cccagaatgc    1320
agaccctgcc ggtggcctct gccctcagca gtcaccgcac cggccctccc ccaatcagcc    1380
ccagcaagag gaagttcagc atggagccag gtgacgagga cctagactgt gacaacgacc    1440
acgtctccaa aatgagtcgc atcttcaacc cccatctgaa caagactgcc aatggagact    1500
gccgcagaga ccccgggag cggagccgca gccccatcga gcgcgctgtg ccccccacca     1560
tgagcctgca cggcagccac ctgtacacct ccctccccag ccttggcctg gagcagcccc    1620
tcgcactgac caagaacagc ctggacgcca gcaggccagc cggcctctcg cccacactga    1680
ccccggggga gcggcagcag aaccggccct ccgtgatcac ctgtgcctcg gctggcgccc    1740
gcaactgcaa cctctcgcac tgccccatcg cgcacagcgg ctgtgccgcg cccgggcctg    1800
ccagctaccg gaggccaccg agcgctgcca ccacctgtga ccccgtggtg gaggaggcag    1860
cccgcaggag cctgggcaag aattacaagg agcccgagcc ggcacccaac tccgtgtcca    1920
tcacgggctc cgtggacgac gcagctgcca aagctctggg tgacacgtgg ctccagatca    1980
aagcggccaa ggacggagca tccagcagcc ctgagtccgc ctctcgcagg ggccagcccg    2040
ccagcccctc tgcccacatg gtcagccaca gtcactcccc ctctgtggtc tccgccatgg    2100
tgagcaaggg cgaggagctg ttcaccgggg tggtgcccat cctggtcgag ctggacggcg    2160
acgtaaacgg ccacaagttc agcgtgtccg gcgagggcga gggcgatgcc acctacggca    2220
agctgaccct gaagttcatc tgcaccaccg gcaagctgcc cgtgccctgg cccaccctcg    2280
tgaccaccct gacctacggc gtgcagtgct tcagccgcta ccccgaccac atgaagcagc    2340
acgacttctt caagtccgcc atgcccgaag gctacgtcca ggagcgcacc atcttcttca    2400
aggacgacgg caactacaag acccgcgccg aggtgaagtt cgaggcgac accctggtga    2460 accgcatcga gctgaagggc atcgacttca aggaggacgg caacatcctg ggcacaagc    2520 tggagtacaa ctacaacagc cacaacgtct atatcatggc cgacaagcag aagaacggca    2580
tcaaggtgaa cttcaagatc cgccacaaca tcgaggacgg cagcgtgcag ctcgccgacc    2640
actaccagca gaacaccccc atcggcgacg gccccgtgct gctgcccgac aaccactacc    2700
tgagcaccca gtccgccctg agcaaagacc ccaacgagaa gcgcgatcac atggtcctgc    2760
tggagttcgt gaccgccgcc gggatcactc tcggcatgga cgagctgtac aagtaa        2816
```

<210> SEQ ID NO 41
<211> LENGTH: 16
<212> TYPE: PRT
<213> ORGANISM: Homo sapiens

<400> SEQUENCE: 41

Asp Pro Val Val Glu Glu His Phe Arg Arg Ser Leu Gly Lys Asn Tyr
1               5                   10                  15

<210> SEQ ID NO 42
<211> LENGTH: 16
<212> TYPE: PRT
<213> ORGANISM: Homo sapiens

```
<400> SEQUENCE: 42

Thr Gly Ser Val Asp Asp His Phe Ala Lys Ala Leu Gly Asp Thr Trp
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Homo sapiens

<400> SEQUENCE: 43

Asp Pro Val Val Glu Glu Ala Ala Arg Arg Ser Leu Gly Lys Asn Tyr
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Homo sapiens

<400> SEQUENCE: 44

Thr Gly Ser Val Asp Asp Ala Ala Ala Lys Ala Leu Gly Asp Thr Trp
1               5                   10                  15
```

VGLL4 WITH UCP-1 CIS-REGULATORY ELEMENT AND METHOD OF USE THEREOF

CROSS-REFERENCE TO RELATED APPLICATIONS

This application is a Non-Provisional U.S. Patent Application and claims priority to U.S. Provisional Application continuation of U.S. Patent Application No. 62/872,624, filed Jul. 10, 2019, the entire contents of which is incorporated herewith in its entirety.

GOVERNMENT RIGHTS STATEMENT

This invention was made with Government support under grant number HL138454 awarded by the National Institutes of Health. The Government has certain rights in the invention.

SEQUENCE LISTING

The instant application contains a Sequence Listing, created on Jul. 9, 2020; the file, in ASCII format, is designated H1789760.txt and is 65.9 KB in size. The file is hereby incorporated by reference in its entirety into the instant application.

BACKGROUND

Obesity is a global epidemic that plagues the human society, threatening the health of both adult and children. Effective pharmacological therapies for obesity are urgently needed. Obesity-related pathologies include, among others, diabetes and liver disease. Adipose tissue overgrowth is the root of obesity, with deleterious health effects. Adipose tissue is composed of white and brown adipose tissue (BAT). White adipose tissue (WAT) stores triglycerides in adipocytes, and BAT burns triglycerides and glucose for generating heat. The development of obesity depends not only on the balance between food intake and caloric utilization but also on the balance between BAT and WAT. Higher BAT is correlated with leanness in the adult and greater muscle volume in children, indicating that functional BAT benefits both energy homeostasis and muscle growth. In humans, BAT is abundant in infants, and decreases with age. Recently, the discovery of functional BAT in adult individuals raised the possibility of treating obesity by activating BAT. However, compositions and methods for increasing BAT are lacking. The present disclosure is directed to overcoming these and other deficiencies in the art.

SUMMARY

The following disclosure includes improvements over such shortcomings.

In an aspect, provided is a polynucleotide, including a cis-regulatory element and a nucleotide sequence encoding a vestigial like 4 protein, wherein the cis-regulatory element includes an uncoupling protein 1 enhancer and an uncoupling protein 1 promoter. In an example, the uncoupling protein 1 enhancer has at least 90% identity with a sequence selected from SEQ ID NO: 1, SEQ ID NO 4, and SEQ ID NO: 7. In another example, the uncoupling protein 1 enhancer is selected from SEQ ID NO: 1, SEQ ID NO 4, and SEQ ID NO: 7. In another example, the uncoupling protein 1 promotor has at least 90% identity with a sequence selected from SEQ ID NO: 2, SEQ ID NO 5, and SEQ ID NO: 8. In still another example, the uncoupling protein 1 promotor is selected from SEQ ID NO: 2, SEQ ID NO 5, and SEQ ID NO: 8. In yet another example, the cis-regulatory element has at least 90% homology with a sequence selected from SEQ ID NO: 3, SEQ ID NO: 6, and SEQ ID NO: 9. In a further example, the cis-regulatory element is selected from SEQ ID NO: 3, SEQ ID NO: 6, and SEQ ID NO: 9.

In another example, the vestigial like 4 protein has at least 90% homology with a sequence selected from SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, and SEQ ID NO: 33. In still another example, the vestigial like 4 protein is selected from SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, and SEQ ID NO: 33. In yet another example, the sequence encoding a vestigial like 4 protein has at least 90% identity with a sequence selected from SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, and SEQ ID NO: 32. In a further example, the sequence encoding a vestigial like 4 protein is selected from SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, and SEQ ID NO: 32.

In another example, the vestigial like 4 protein has from 0 to 3 substitutions to a sequence selected from SEQ ID NO: 11, SEQ ID NO: 13, SEQ ID NO: 15, SEQ ID NO: 17, SEQ ID NO: 19, and SEQ ID NO: 21, wherein the substitutions are not in a TDU domain. In still another example, the vestigial like 4 protein has from 0 to 3 substitutions to a sequence selected from SEQ ID NO: 23, SEQ ID NO: 25, SEQ ID NO: 27, SEQ ID NO: 29, SEQ ID NO: 31, and SEQ ID NO: 33, wherein the substitutions are not in a TDU domain.

Another example further includes an intron between the cis-regulatory element and the nucleotide sequence encoding a vestigial like 4 protein. In another example, the intron has at least 90% homology with SEQ ID NO: 34. In still another example, the intron is SEQ ID NO: 34.

Another example includes a nucleotide sequence having at least 90% homology with SEQ ID NO: 35. An example includes a nucleotide sequence of SEQ ID NO: 35. Another example includes a nucleotide sequence having at least 90% homology with SEQ ID NO: 36. An example includes a nucleotide sequence of SEQ ID NO: 36.

Another example further includes a nucleotide sequence encoding a reporter protein. In another example, the reporter protein is selected from a green fluorescent protein, a yellow fluorescent protein, a red fluorescent protein, a blue fluorescent protein, a luciferase protein, a beta-galactosidase protein, a glutathione S-transferase protein, a chloramphenicol acetyltransferase protein, and any combination of two or more of the foregoing. In still another example, the reporter protein includes a green fluorescent protein. In yet another example, the reporter protein includes SEQ ID NO: 37. In a further example, the nucleotide sequence encoding a reporter protein includes SEQ ID NO: 38.

Another example includes a nucleotide sequence having at least 90% homology with SEQ ID NO: 39. An example includes SEQ ID NO: 39. Another example includes a nucleotide sequence having at least 90% homology with SEQ ID NO: 40. An example includes SEQ ID NO: 40.

In another aspect, provided is a viral vector including any of the foregoing examples of a polynucleotide that include a cis-regulatory element and a nucleotide sequence encoding a vestigial like 4 protein. In an example, the viral vector includes an adenoviral associated vector.

In another aspect, provided is a cell transfected with any of the foregoing examples of a polynucleotide that include a cis-regulatory element and a nucleotide sequence encoding a vestigial like 4 protein. In an example, the cell was contacted with any of the foregoing examples of a viral vector that include any of the foregoing examples of a polynucleotide that include a cis-regulatory element and a nucleotide sequence encoding a vestigial like 4 protein.

In still another aspect, provided is an organism transfected with any of the foregoing examples of a polynucleotide that include a cis-regulatory element and a nucleotide sequence encoding a vestigial like 4 protein. In an example, the organism was contacted with any of the foregoing examples of a viral vector.

In another aspect, provided is a method. In an example, the method includes transfecting a cell with any of the foregoing examples of a polynucleotide that include a cis-regulatory element and a nucleotide sequence encoding a vestigial like 4 protein. In another example, transfecting includes contacting the cell with any of the foregoing examples of a viral vector that include any of the foregoing examples of a polynucleotide that include a cis-regulatory element and a nucleotide sequence encoding a vestigial like 4 protein. In still another example includes transfecting an organism with any of the foregoing examples of a polynucleotide that include a cis-regulatory element and a nucleotide sequence encoding a vestigial like 4 protein. In yet another example, transfecting includes contacting the organism with any of the foregoing examples of a viral vector that include any of the foregoing examples of a polynucleotide that include a cis-regulatory element and a nucleotide sequence encoding a vestigial like 4 protein.

In another example, the organism is a mammal. In still another example, the organism is a human.

In an example of the method, the vestigial like protein 4 does not include an HF to AA substitution in a TDU domain of the vestigial like protein 4 and the transfecting includes increasing a ratio of a volume of brown adipose tissue to a volume of white adipose tissue in the organism. In still another example, the vestigial like protein 4 does not include an HF to AA substitution in a TDU domain of the vestigial like protein 4 and the transfecting includes increasing a volume of brown adipose tissue in the organism, decreasing the volume of white adipose tissue in the organism, or both. In yet another example, the vestigial like protein 4 does not comprise an HF to AA substitution in a TDU domain and the transfecting includes reducing a ratio of a volume of adipose tissue to a volume of non-adipose tissue in the organism.

In a further example, the vestigial like protein 4 does not include an HF to AA substitution in a TDU domain, and the organism is obese or is at risk of developing obesity. In still a further example, the vestigial like protein 4 does not include an HF to AA substitution in a TDU domain, and the transfecting includes preventing obesity in the organism. In yet another example, the vestigial like protein 4 does not include an HF to AA substitution in a TDU domain, and the transfecting includes treating obesity in the organism. In another example, the vestigial like protein 4 does not include an HF to AA substitution in a TDU domain, and the transfecting includes reducing obesity in the organism.

In an example of the method, the vestigial like protein 4 includes an HF to AA substitution in each of two TDU domains, wherein the transfecting includes reducing a volume of adipose tissue of the organism. In another example, the vestigial like protein 4 includes an HF to AA substitution in each of two TDU domains, and the transfecting includes reducing a volume of brown adipose tissue of the organism. In still another example, the vestigial like protein 4 includes an HF to AA substitution in a TDU domain, and the organism is obese or is at risk of developing obesity. In yet another example, the vestigial like protein 4 includes an HF to AA substitution in a TDU domain, and the transfecting includes preventing obesity in the organism. In a further example, the transfecting includes treating obesity in the organism. In still a further example, the vestigial like protein 4 includes an HF to AA substitution in a TDU domain, and the transfecting includes reducing obesity in the organism.

In an example of the method, the vestigial like protein 4 includes an HF to AA substitution in each of two TDU domains, and the transfecting includes reducing fatty acid synthesis in the organism. In another example, the vestigial like protein 4 includes an HF to AA substitution in a TDU domain, and the organism has hepatic steatosis or is at risk for developing hepatic steatosis. In still another example, the vestigial like protein 4 includes an HF to AA substitution in each of two TDU domains, and the transfecting includes preventing hepatic steatosis in the organism. In yet another example, the vestigial like protein 4 includes an HF to AA substitution in each of two TDU domains, and the transfecting includes treating hepatic steatosis in the organism. In a further example, the vestigial like protein 4 includes an HF to AA substitution in each of two TDU domains, and the transfecting includes reducing hepatic steatosis in the organism.

In an example of the method, the vestigial like protein 4 includes an HF to AA substitution in each of two TDU domains, and the organism has diabetes or is at risk of developing diabetes. In another example, the vestigial like protein 4 includes an HF to AA substitution in each of two TDU domains, wherein the transfecting includes preventing diabetes in the organism. In still another example, the vestigial like protein 4 includes an HF to AA substitution in each of two TDU domains, wherein the transfecting includes treating diabetes in the organism.

BRIEF DESCRIPTION OF THE DRAWINGS

These and other features, aspects, and advantages of the present disclosure will become better understood when the following detailed description is read with reference to the accompanying drawings, wherein:

FIGS. 33B and 33C show total body weight and accumulated body weight gain, respectively. AAV.GFP is the upper tracing and AAV.Vgll4.GFP is the lower.

FIGS. 34A and 34B show immunofluorescence images of interscapular brown adiposites (MCT1 was used to label the cell borders) and Vgll4 expression, respectively, of 8-week-old C57/BL6 mice 10 days after AAV.BCE.Vgll4 or AAV.BCE.GFP was subcutaneously injected into the interscapular region.

FIGS. 34C AND 34D show real-time PCR measurements of various mRNA transcripts in brown adipose tissue. Control (AAV.BCE.GFP) is on the right and AAV.BCE.Vgll4-HF4A is on the right.

FIGS. 35B and 3FC show total body weight and accumulated body weight gain, respectively.

FIGS. 36A, 36B, 36C, 36D, AND 36E are graphs showing a ratio of brown adipose tissue weight to body weight, Vgll4 mRNA expression in BAT, Ucp1 mRNA expression in BAT, mitochondrial gene mRNA levels in BAT, and fatty acid synthesis gene mRNA expression in BAT. Student t test, *, P<0.05; **, P<0.01. Control (AAV.BCE.GFP) is on the right and AAV.BCE.Vgll4-HF4A is on the left.

FIG. 37A shows that pre-treatment with AAV.BCE.Vgll4-HF4A reduces ratio of liver weight to body weight. FIG. 37B shows liver Vgll4 mRNA expression level. FIGS. 37C and 37D are photomicrographs showing HE staining and oil red staining, respectively, of liver sections (bar=100 µm).

DETAILED DESCRIPTION

Figure 1:
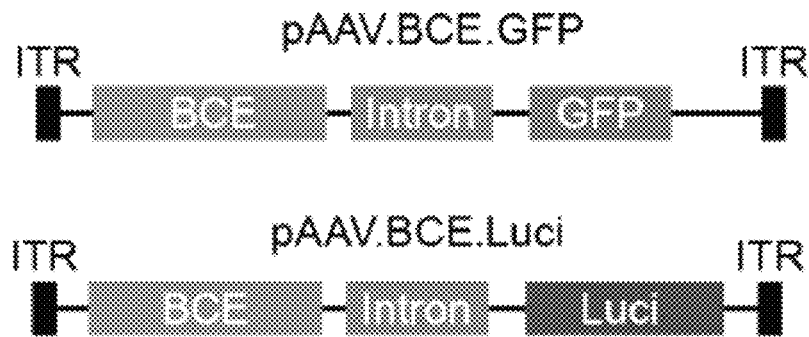
FIG. 1 shows a schematic view of constructs in accordance with aspects of the present disclosure.

This disclosure relates to a construct including a cis-regulatory element upstream of a coding sequence for a vestigial like 4 peptide (Vgll4). In an example, a cis-regulatory element may promote expression of a Vgll4 peptide in BAT cells. In an example, a cis-regulatory element may also promote expression of a Vgll4 peptide in liver cells. It may further specifically or enrichingly drive expression in BAT cells relative to expression driven in many or most other cells, when cells are transfected with the construct. In an example, it may further specifically or enrichingly drive expression in BAT and liver cells relative to expression driven in many or most other cells, when cells are transfected with the construct. Also disclosed is a viral vector including the construct, wherein the viral vector enables, permits, or promotes transfection of cells with the construct. In some examples, the Vgll4 peptide may include amino acid substitutions. For example, Vgll4 peptides include two TONDU (or TDU) domains, referred to herein as TDU_1 and TDU_2. Each TDU domain includes an HF dipeptide sequence. In an example, one or both HF TDU dipeptides may include amino acid substitutions, replacing HF with a dipeptide of aliphatic amino acids, such as AA.

In an example, also disclosed is causing an increase in BAT, a decrease in WAT, an increase in a ratio of BAT volume to WAT volume, or any two of the foregoing, by contacting an organism with the construct, such as by transfecting cells of an organism with the construct. In an example, also disclosed is reducing a volume of adipose tissue of the organism by contacting an organism with the construct, such as by transfecting cells of an organism with the construct. In an example, also disclosed is reducing a mass ratio BAT to body weight of an organism by contacting an organism with the construct, such as by transfecting cells of an organism with the construct. In an example, also disclosed is reducing a liver volume, liver weight, intrahepatic fat content, or any combination of two or more of the foregoing, of an organism by contacting an organism with the construct, such as by transfecting cells of an organism with the construct.

In an example, also disclosed is reducing or minimizing blood glucose levels or a rise in glucose levels in an organism by contacting an organism with the construct, such as by transfecting cells of an organism with the construct. In an example, also disclosed is increasing expression of mitochondrial genes, such as mitochondrial genes involved in mitochondrial respiration, in an organism by contacting an organism with the construct, such as by transfecting cells of an organism with the construct. In an example, also disclosed is decreasing expression of genes that promote lipogenesis, in an organism by contacting an organism with the construct, such as by transfecting cells of an organism with the construct.

In an example, a viral vector including the construct is used to transfect cells of an organism with the construct. A viral vector may be an adeno-associated viral vector or another viral vector known to be able to transfect cells. The organism may be a mammal, such as a rodent or human or any other mammal.

Vgll4 is a transcription co-factor known to interact with cellular signaling molecules and transcription factors to influence cell survival and cell function. Vgll4 is particularly known for promoting cellular death by inhibiting YAP-TEAD1 complex. Several isoforms of Vgll4 have been identified, arising from splice variants to the Vgll4 gene. These include Vgll4A, Vgll4B, Vgll4C Vgll4D, Vgll4E, and Vgll4F. Amino acid sequences of these Vgll4 proteins (referred to collectively here as Vgll4), and examples of polynucleotides encoding them encoding them, are given in Table II. Vgll4 has been linked with an anticancer effect in several types of cancer, where lower levels of Vgll4 correlate or correspond with or cause increased tumor cell survival and higher levels of Vgll4 correlate or correspond with or cause an anti-tumor effect including decreased metastatic processes and decreased tumor cell survival or proliferation. See Deng, Vgll4 is a transcriptional cofactor acting as a novel tumor suppressor via interacting with TEADs, Am J Cancer Res (2018), 8(6):932-943. In this respect, Vgll4 differs from other member of the vestigial like (Vgll) family (Vgll1, Vgll2, and Vgll3) of transcription co-factors, which are not known to have tumor-suppressive functions. Vgll family members other than Vgll4 are not generally understood to share functional commonalities with Vgll4.

In view of the well-established role of increased Vgll4 expression in promoting cellular death processes or inhibiting cell survival, an increase in BAT volume as disclosed herein surprisingly results from Vgll4 expression influenced by a BAT-cell specific cis-regulatory element. In another example, and without being limited to any particular mechanism of action, where a Vgll4 protein includes HF to AA substitutions in both TDU domains, a reduced BAT volume, reduced intrahepatic fat accumulation, or both, may result from Vgll4 activity that does not include Vgll4 integration with a TEAD protein. In another example, and without being limited to any particular mechanism of action, where a Vgll4 protein includes HF to AA substitutions in both TDU domains, a reduced BAT volume, reduced intrahepatic fat accumulation, or both, may result from increased expression of mitochondrial genes involved in mitochondrial respiration, decreased expression of genes involved in lipogenesis, or both.

For driving expression under control of a cis-regulatory element, cis-regulatory elements of uncoupling protein 1 (Ucp1) may be placed adjacent to a coding sequence for a Vgll4. By cis-regulatory element, what is meant is a nucleotide sequence that regulates the transcription of neighboring gene or coding sequences. Conventionally, Ucp1 is considered to be expressed specifically in BAT cells. Thus, such a cis-regulatory element may drive expression mostly, or predominantly, or in some cases exclusively, in BAT cells. Surprisingly, however, as disclosed herein, such a cis-regulatory element may drive expression in liver cells in addition to expression in BAT cells. In an example, such a cis-regulatory element may drive expression only in BAT and liver cells.

A cis-regulatory element may include a promotor, an enhancer, or both. In some cases, a sequence for a cis-regulatory element may be located within fewer than 10 nucleotides from a transcription start site, fewer than 20 nucleotides from a transcription start site, fewer than 30 nucleotides from a transcription start site, fewer than 40 nucleotides from a transcription start site, fewer than 50 nucleotides from a transcription start site, fewer than 60 nucleotides from a transcription start site, fewer than 70 nucleotides from a transcription start site, fewer than 80 nucleotides from a transcription start site, fewer than 90 nucleotides from a transcription start site, fewer than 100 nucleotides from a transcription start site, fewer than 125 nucleotides from a transcription start site, fewer than 150 nucleotides from a transcription start site, fewer than 175 nucleotides from a transcription start site, fewer than 200 nucleotides from a transcription start site, fewer than 225 nucleotides from a transcription start site, fewer than 250 nucleotides from a transcription start site, fewer than 275 nucleotides from a transcription start site, fewer than 300 nucleotides from a transcription start site, fewer than 325 nucleotides from a transcription start site, fewer than 35 nucleotides from a transcription start site, fewer than 375 nucleotides from a transcription start site, fewer than 400 nucleotides from a transcription start site, fewer than 425 nucleotides from a transcription start site, fewer than 450 nucleotides from a transcription start site, fewer than 475 nucleotides from a transcription start site, fewer than 500 nucleotides from a transcription start site, or between 500 and 1,000 nucleotides from a transcription start site A promoter is a nucleotide sequence to which RNA polymerizing enzymes bind for initiation of transcription of a downstream gene sequence. Many genes that show tissue- or cell-type specific expression including a promotor upstream of the DNA sequence that codes for the RNA that is particularly active in cells where the gene is expressed. A promoter may be more active in some cells than other, such as being active only in specific ell- or tissue-types, or highly active in certain cell- or tissue-types relative to others. Promoters include a sequence where transcription is initiated. Eukaryotic promoters may and typically do include features such as a TATA box, a transcription factor IIB recognition site, and a core promotor sequence (or an initiator). Transcription factors bind and RNA polymerase bind to a promoter for transcription initiation.

Also included in a cis-regulatory element may be one or more enhancer sequence. An enhancer is part of a cis-regulatory element that enhances transcription initiated in or by the promotor. An enhancer may serve to promote an initiation of transcription at a promoter, for example, such as through binding of additional transcription factors to the enhancer that facilitate or enhance recruitment of other factors and transcriptional machinery to the promotor. As with promotors, many genes have enhances that are involved in cell- or tissue-specific or cell- or tissue-enhanced expression.

Ucp1 is a mitochondrial protein expressed specifically in BAT cells. The Ucp1 gene includes a cis regulatory element in which enhancer and promotor elements have been identified and characterized. Such cis-regulatory elements are responsible for promoting expression of neighboring gene sequences in BAT cells and not other tissue or cell types. Sequences that may be included in a cis regulatory element in accordance with the present disclosure as based on cis regulatory elements of Ucp1 genes are shown in Table I.

TABLE I

Cis Regulatory Element Sequences

| SEQ ID NO | Identity | Sequence |
|---|---|---|
| 1 | Mouse Ucp1 enhancer | GCATGCCAATTTATAGTGCCGTCACTAACAGTACTGATACTTTAA CATGCTAAGTTTAAAGTGTGTGCTATATTAATTGTAAGATTGGTG AAGAGAGGTGTTATCAGATGGAAGCTGCACATTTCTGGATTAATG TGGTTAAATGTATCTTCTCCTGTGATTACTGTCTTTATTTCTTCTTT TAAAATATTGTCATTTGGACATCTATCTGTATAGCTACGCCCTGAC ACGTCCTCCTGGAGACAGATAAGAAGTTACGACGGGAGGAGCAG ATGGAGGCAAAGCGCTGTGATGCTTTTGTGGTTTGAGTGCACACA TTTGTTCAGTGATTCTGTGAAATGAGTGAGCAAATGGTGACCGGG TGCCCTGTAAATGGTGTTCTACATCTTAAGAGAAGAACACGGACA CTAGGTAAGTGAAGCTTGCTGTCACTCCTCTACAGCGTCACAGAG GGTCAGTCACCCTTGACCACACTGAACTAGTCGTCACCTTTCCACT CTTCCTGCCAGAAGAGCAGAAATCAGACTCTCTGGGGATATCAGC CTCACCCCTACTGCTCTCTCCATTATGAGGCAAACTTTCTTTCACT TCCCAGAGGCTCTGGGGGCAGCAAGGTCAACCCTTTCCTCAGACT CTAG |
| 2 | Mouse Ucp1 promoter | TCTCGGAGGAGATCAGATCGCGCTTATTCAAGGGAACCAGCCCCT GCTCTGCGCCCTGGTCCAAGGCTGTTGAAGAGTGACAAAAGGCAC CACGCTGCGGGGACGCGGGTGAAGCCCCTCTGTGTGTCCTCTGGG CATAATCAGGAACTGGTGCCAAATCAGAGGTGATGTGGCCAGGG CTTTGGGAGTGACGCGCGGCTGGGAGGCTTGCGCACCCAAGGCA CGCCCCTGCCAAGTCCCACTAGCAGCTCTTTGGAGACCTGGGCCG GCTCAGCCACTTCCCCCAGTCCCTCCTCCGGCAAGGGGCTATATA GATCTCCCAGGTCAGGGCGCAG |
| 3 | Mouse Ucp1 enhancer-promoter | GCATGCCAATTTATAGTGCCGTCACTAACAGTACTGATACTTTAA CATGCTAAGTTTAAAGTGTGTGCTATATTAATTGTAAGATTGGTG AAGAGAGGTGTTATCAGATGGAAGCTGCACATTTCTGGATTAATG TGGTTAAATGTATCTTCTCCTGTGATTACTGTCTTTATTTCTTCTTT TAAAATATTGTCATTTGGACATCTATCTGTATAGCTACGCCCTGAC ACGTCCTCCTGGAGACAGATAAGAAGTTACGACGGGAGGAGCAG ATGGAGGCAAAGCGCTGTGATGCTTTTGTGGTTTGAGTGCACACA TTTGTTCAGTGATTCTGTGAAATGAGTGAGCAAATGGTGACCGGG TGCCCTGTAAATGGTGTTCTACATCTTAAGAGAAGAACACGGACA CTAGGTAAGTGAAGCTTGCTGTCACTCCTCTACAGCGTCACAGAG GGTCAGTCACCCTTGACCACACTGAACTAGTCGTCACCTTTCCACT CTTCCTGCCAGAAGAGCAGAAATCAGACTCTCTGGGGATATCAGC |

TABLE I-continued

Cis Regulatory Element Sequences

| SEQ ID NO | Identity | Sequence |
|---|---|---|
| | | CTCACCCCTACTGCTCTCTCCATTATGAGGCAAACTTTCTTTCACT<br>TCCCAGAGGCTCTGGGGGCAGCAAGGTCAACCCTTTCCTCAGACT<br>CTAGTCTCGGAGGAGATCAGATCGCGCTTATTCAAGGGAACCAGC<br>CCCTGCTCTGCGCCCTGGTCCAAGGCTGTTGAAGAGTGACAAAAG<br>GCACCACGCTGCGGGGACGCGGGTGAAGCCCCTCTGTGTGTCCTC<br>TGGGCATAATCAGGAACTGGTGCCAAATCAGAGGTGATGTGGCC<br>AGGGCTTTGGGAGTGACGCGCGGCTGGGAGGCTTGCGCACCCAA<br>GGCACGCCCCTGCCAAGTCCCACTAGCAGCTCTTTGGAGACCTGG<br>GCCGGCTCAGCCACTTCCCCCAGTCCCTCCTCCGGCAAGGGGCTA<br>TATAGATCTCCCAGGTCAGGGCGCAG |
| 4 | Rat adipose-specific UCP1 enhancer | GACGTCACAGTGGGTCAGTCACCCTTGATCACACTGCACCAGTCT<br>TCACCTTTCCACGCTTCCTGCCAGAGCATGAATCAGGCTCTCTGG<br>GGATACCGGCCTCACCCCTACTGAGGCAAACTTTCTCCCACTTCTC<br>AGAGGCTCTGAGGGCAGCAAGGTCAGCCCTTTCTTTGGAATCTAG<br>AACCACTCCCTGTCTTGAGCTGACATCACAGGGCAGGCAGATGCA<br>GCAGGGAAGGGCCTGGGACTGGGACGTTCATCCTACAAGAAAGC<br>TGTGGAACTTTTCAGCAACATCTCA |
| 5 | Rat basal UCP1 promoter | GAAATCAGATCGCACTTATTCAAAGGAGCCAGGCCCTGCTCTGCG<br>CCCTGGTGGAGGCTCCTCATGTGAAGAGTGACAAAAGGCACCAT<br>GTTGTGGATACGGGGCGAAGCCCCTCCGGTGTGTCCTCCAGGCAT<br>CATCAGGAACTAGTGCCAAAGCAGAGGTGCTGGCCAGGGCTTTG<br>GGAGTGACGCGCGTCTGGGAGGCTTGTGCGCCCAGGGCACGCCC<br>CTGCCGATTCCCACTAGCAGGTCTTGGGGGACCTGGGCCGGCTCT<br>GCCCCTCCTCCAGCAATCGGGCTATAAAGCTCTTCCAAGTCAGGG<br>CGCAGAAGTGCCGGGCGATCCGGGCTTAAAGAGCGAGAGGAAGG<br>GACGCTCACCTTTGAGCTCCTCCACAAATAGCCCTGGTGGCTGCC<br>ACAGAAGTTCGAAGTTGAGAGTTCGG |
| 6 | Rat UCP1 enhancer with rat basal UCP1 promoter | GACGTCACAGTGGGTCAGTCACCCTTGATCACACTGCACCAGTCT<br>TCACCTTTCCACGCTTCCTGCCAGAGCATGAATCAGGCTCTCTGG<br>GGATACCGGCCTCACCCCTACTGAGGCAAACTTTCTCCCACTTCTC<br>AGAGGCTCTGAGGGCAGCAAGGTCAGCCCTTTCTTTGGAATCTAG<br>AACCACTCCCTGTCTTGAGCTGACATCACAGGGCAGGCAGATGCA<br>GCAGGGAAGGGCCTGGGACTGGGACGTTCATCCTACAAGAAAGC<br>TGTGGAACTTTTCAGCAACATCTCAGAAATCAGATCGCACTTATT<br>CAAAGGAGCCAGGCCCTGCTCTGCGCCCTGGTGGAGGCTCCTCAT<br>GTGAAGAGTGACAAAAGGCACCATGTTGTGGATACGGGGCGAAG<br>CCCCTCCGGTGTGTCCTCCAGGCATCATCAGGAACTAGTGCCAAA<br>GCAGAGGTGCTGGCCAGGGCTTTGGGAGTGACGCGCGTCTGGGA<br>GGCTTGTGCGCCCAGGGCACGCCCCTGCCGATTCCCACTAGCAGG<br>TCTTGGGGGACCTGGGCCGGCTCTGCCCCTCCTCCAGCAATCGGG<br>CTATAAAGCTCTTCCAAGTCAGGGCGCAGAAGTGCCGGGCGATCC<br>GGGCTTAAAGAGCGAGAGGAAGGGACGCTCACCTTTGAGCTCCT<br>CCACAAATAGCCCTGGTGGCTGCCACAGAAGTTCGAAGTTGAGA<br>GTTCGG |
| 7 | Human Ucp1 enhancer | TGATCAAGTGCATTTGTTAATGTGTTCTACATTTTCAAAAGGAA<br>AGGAGAATTTGTTACATTCAGAACTTGCTGCCACTCCTTTGCTACG<br>TCATAAAGGGTCAGTTGCCCTTGCTCATACTGACCTATTCTTTACC<br>TCTCTGCTTCTTCTTTGTGCCAGAAGAGTAGAAATCTGACCCTTTG<br>GGGATACCACCCTCTCCCTACTGCTCTCTCCAACCTGAGGCAAA<br>CTTTCTCCTACTTCCCAGAGCCTGTCAGAAGTGGTGAAGCCAGCC<br>TGCTCCTTGGAATCCAGAACTACTTTCAGAATCTTGAACTTCTGTG<br>ACCTCTCAGGGTCCC |
| 8 | Human Ucp1 promoter | ACCGCCGCGGTGCGCCCTCCCTCCGACGTGCGGTGTGCGGGGCGC<br>AGACAACCAGCGGCCGGCCCAGGGCTTTCGGGGAGCGAAGCAGG<br>GCTCCCGAGGCACCGAGCGAGAATGGGAATGGGAGGGACCCGGT<br>GCTCCCGGACACGCCCCCGGCAGGTCCCACGCCCGGGTCTTCTGA<br>GACCTCGCGCGGCCCAGCCCGGGAGCGGCCCAGCTATATAAGTCC<br>CAGCGGAAGACCGGAACGCAGAGGGTCCTGCTGGCGCGAGGGTG<br>GGTAGGAGGGGACGCGGGGACT |
| 9 | Human Ucp1 enhancer-promoter | TGATCAAGTGCATTTGTTAATGTGTTCTACATTTTCAAAAGGAA<br>AGGAGAATTTGTTACATTCAGAACTTGCTGCCACTCCTTTGCTACG<br>TCATAAAGGGTCAGTTGCCCTTGCTCATACTGACCTATTCTTTACC<br>TCTCTGCTTCTTCTTTGTGCCAGAAGAGTAGAAATCTGACCCTTTG<br>GGGATACCACCCTCTCCCTACTGCTCTCTCCAACCTGAGGCAAA<br>CTTTCTCCTACTTCCCAGAGCCTGTCAGAAGTGGTGAAGCCAGCC<br>TGCTCCTTGGAATCCAGAACTACTTTCAGAATCTTGAACTTCTGTG<br>ACCTCTCAGGGTCCCACCGCCGCGGTGCGCCCTCCCTCCGACGTG<br>CGGTGTGCGGGGCGCAGACAACCAGCGGCCGGCCCAGGGCTTTC |

TABLE I-continued

Cis Regulatory Element Sequences

| SEQ ID NO | Identity | Sequence |
|---|---|---|
| | | GGGGAGCGAAGCAGGGCTCCCGAGGCACCGAGCGAGAATGGGA ATGGGAGGGACCCGGTGCTCCCGGACACGCCCCCGGCAGGTCCC ACGCCCGGGTCTTCTGAGACCTCGCGCGGCCCAGCCCGGGAGCGG CCCAGCTATATAAGTCCCAGCGGAAGACCGGAACGCAGAGGGTC CTGCTGGCGCGAGGGTGGGTAGGAGGGGACGCGGGGACT |

Examples of Ucp1 promotors include those of SEQ ID NO: 2, SEQ ID NO: 5, and SEQ ID NO: 8 (from mouse, rat, and human Ucp1 genes, respectively). Examples of Ucp1 enhancers include those of SEQ ID NO: 1, SEQ ID NO: 4, and SEQ ID NO: 7 (from mouse, rat, and human Ucp1 genes, respectively). In an example, presence of such a Ucp1 enhancer or Ucp1 promotor, or both, or of other Ucp1 enhancer or promotor elements, or both, in the cis-regulatory element of a gene may drive transcription and expression of such gene only in BAT, or only at high levels in BAT, or only at detectable levels in BAT, or at substantially higher levels in BAT compared to other cell types. In another example, presence of such a Ucp1 enhancer or Ucp1 promotor, or both, or of other Ucp1 enhancer or promotor elements, or both, in the cis-regulatory element of a gene may also drive transcription and expression of such gene in liver cells. In some examples, a cis-regulatory element may include multiple Ucp1 enhancer elements, such as more than one of SEQ ID NO: 2, SEQ ID NO: 5, and SEQ ID NO: 8, or combination or combinations thereof.

A Ucp1 cis-regulatory element may include a sequence of SEQ ID NO: 3, SEQ ID NO: 6, or SEQ ID NO: 9. Or, it may include a Ucp1 promotor without a Ucp1 enhancer. A Ucp1 cis-regulatory element may also include combinations of a Ucp1 enhancer and a Ucp1 promotor other than the aforementioned examples, such as any one or more of enhancer SEQ ID NO: 1, SEQ ID NO: 4, and SEQ ID NO: 7, together with any one of promotor SEQ ID NO: 2, SEQ ID NO: 5, and SEQ ID NO: 8. All possible combinations and permutations of the foregoing are explicitly contemplated herein and explicitly included as examples of the present disclosure.

A cis-regulatory element including a rat Ucp1 enhancer of SEQ ID NO: 4 and a rat Ucp1 promotor of SEQ ID NO: 5 has previously been shown to drive expression of a neighboring gene in a BAT-specific manner. US Patent Application Publication No. 2016/0319303A1. As disclosed herein, a cis-regulatory element including a mouse Ucp1 enhancer of SEQ ID NO: 1, a mouse Ucp1 promotor of SEQ ID NO: 2, or both (as in SEQ ID NO: 3) may also drive expression of a neighboring gene in a BAT-specific manner. Surprisingly, as further disclosed herein, a cis-regulatory element including a Ucp1 enhancer and a Ucp1 promotor may also induce expression in liver cells. Some examples may have a Ucp1 enhancer sequence, Ucp1 promoter sequence, or Ucp1 cis-regulatory element, with 90% or more, or 95% or more, or 97.5% or more sequence homology with any of the corresponding, foregoing examples.

Amino acid sequences, and non-limiting examples of nucleotide sequences encoding such Vgll4 peptide sequences, are shown in Table II.

TABLE II

Vgll4 sequences

| SEQ ID NO | Identity | Sequence |
|---|---|---|
| 10 | Vgll4A nucleotide | ATGCTATTTATGAAGATGGACCTGTTGAACTATCAGTACTTGGAC AAGATGAACAACAATATCGGCATTCTGTGCTACGAAGGCGAAGC TGCTCTCAGGGGAGAACCCAGAATACAGACCCTGCCGGTGGCCTC TGCCCTCAGCAGTCACCGCACCGGCCCTCCCCCAATCAGCCCCAG CAAGAGGAAGTTCAGCATGGAGCCAGGTGACGAGGACCTAGACT GTGACAACGACCACGTCTCCAAAATGAGTCGCATCTTCAACCCCC ATCTGAACAAGACTGCCAATGGAGACTGCCGCAGAGACCCCCGG GAGCGGAGCCGCAGCCCCATCGAGCGCGCTGTGGCCCCCACCAT GAGCCTGCACGGCAGCCACCTGTACACCTCCCTCCCCAGCCTTGG CCTGGAGCAGCCCCTCGCACTGACCAAGAACAGCCTGGACGCCA GCAGGCCAGCCGGCCTCTCGCCCACACTGACCCCGGGGGAGCGG CAGCAGAACCGGCCCTCCGTGATCACCTGTGCCTCGGCTGGCGCC CGCAACTGCAACCTCTCGCACTGCCCCATCGCGCACAGCGGCTGT GCCGCGCCCGGGCCTGCCAGCTACCGGAGGCCACCGAGCGCTGC CACCACCTGTGACCCCGTGGTGGAGGAGCATTTCCGCAGGAGCCT GGGCAAGAATTACAAGGAGCCCGAGCCGGCACCCAACTCCGTGT CCATCACGGGCTCCGTGGACGACCACTTTGCCAAAGCTCTGGGTG ACACGTGGCTCCAGATCAAAGCGGCCAAGGACGGAGCATCCAGC AGCCCTGAGTCCGCCTCTCGCAGGGGCCAGCCCGCCAGCCCCTCT GCCCACATGGTCAGCCACAGTCACTCCCCCTCTGTGGTCTCC |
| 11 | Vgll4A amino acid | MLFMKMDLLNYQYLDKMNNNIGILCYEGEAALRGEPRIQTLPVASA LSSHRTGPPPISPSKRKFSMEPGDEDLDCDNDHVSKMSRIFNPHLNKT ANGDCRRDPRERSRSPIERAVAPTMSLHGSHLYTSLPSLGLEQPLALT KNSLDASRPAGLSPTLTPGERQQNRPSVITCASAGARNCNLSHCPIAH SGCAAPGPASYRRPPSAATTCDPVVEEHFRRSLGKNYKEPEPAPNSV |

TABLE II-continued

Vgl14 sequences

| SEQ ID NO | Identity | Sequence |
|---|---|---|
| | | SITGSVDDHFAKALGDTWLQIKAAKDGASSSPESASRRGQPASPSAH MVSHSHSPSVVS |
| 12 | Vgl14B nucleotide | ATGGAGACGCCATTGGATGTTTTGTCCAGGGCAGCATCTCTGGTG CATGCTGATGACGAAAAACGCGAAGCTGCTCTCAGGGGAGAACC CAGAATACAGACCCTGCCGGTGGCCTCTGCCCTCAGCAGTCACCG CACCGGCCCTCCCCCAATCAGCCCCAGCAAGAGGAAGTTCAGCAT GGAGCCAGGTGACGAGGACCTAGACTGTGACAACGACCACGTCT CCAAAATGAGTCGCATCTTCAACCCCCATCTGAACAAGACTGCCA ATGGAGACTGCCGCAGAGACCCCCGGGAGCGGAGCCGCAGCCCC ATCGAGCGCGCTGTGGCCCCCACCATGAGCCTGCACGGCAGCCAC CTGTACACCTCCCTCCCCAGCCTTGGCCTGGAGCAGCCCCTCGCA CTGACCAAGAACAGCCTGGACGCCAGCAGGCCAGCCGGCCTCTC GCCCACACTGACCCCGGGGGAGCGGCAGCAGAACCGGCCCTCCG TGATCACCTGTGCCTCGGCTGGCGCCCGAACTGCAACCTCTCGC ACTGCCCCATCGCGCACAGCGGCTGTGCCGCGCCCGGGCCTGCCA GCTACCGGAGGCCACCGAGCGCTGCCACCACCTGTGACCCCGTGG TGGAGGAGCATTTCCGCAGGAGCCTGGGCAAGAATTACAAGGAG CCCGAGCCGGCACCCAACTCCGTGTCCATCACGGGCTCCGTGGAC GACCACTTTGCCAAAGCTCTGGGTGACACGTGGCTCCAGATCAAA GCGGCCAAGGACGGAGCATCCAGCAGCCCTGAGTCCGCCTCTCGC AGGGGCCAGCCCGCCAGCCCTCTGCCCACATGGTCAGCCACAGT CACTCCCCCTCTGTGGTCTCC |
| 13 | Vgl14B peptide | METPLDVLSRAASLVHADDEKREAALRGEPRIQTLPVASALSSHRTG PPPISPSKRKFSMEPGDEDLDCDNDHVSKMSRIFNPHLNKTANGDCR RDPRERSRSPIERAVAPTMSLHGSHLYTSLPSLGLEQPLALTKNSLDA SRPAGLSPTLTPGERQQNRPSVITCASAGARNCNLSHCPIAHSGCAAP GPASYRRPPSAATTCDPVVEEHFRRSLGKNYKEPEPAPNSVSITGSVD DHFAKALGDTWLQIKAAKDGASSSPESASRRGQPASPSAHMVSHSH SPSVVS |
| 14 | Vgl14C nucleotide | ATGATTAAAGTGAGGAACAAGACTGCCAATGGAGACTGCCGCAG AGACCCCCGGGAGCGGAGCCGCAGCCCCATCGAGCGCGCTGTGG CCCCCACCATGAGCCTGCACGGCAGCCACCTGTACACCTCCCTCC CCAGCCTTGGCCTGGAGCAGCCCCTCGCACTGACCAAGAACAGC CTGGACGCCAGCAGGCCAGCCGGCCTCTCGCCCACACTGACCCCGG GGGAGCGGCAGCAGAACCGGCCCTCCGTGATCACCTGTGCCTCGG CTGGCGCCCGCAACTGCAACCTCTCGCACTGCCCCATCGCGCACA GCGGCTGTGCCGCGCCCGGGCCTGCCAGCTACCGGAGGCCACCG AGCGCTGCCACCACCTGTGACCCCGTGGTGGAGGAGCATTTCCGC AGGAGCCTGGGCAAGAATTACAAGGAGCCCGAGCCGGCACCCAA CTCCGTGTCCATCACGGGCTCCGTGGACGACCACTTTGCCAAAGC TCTGGGTGACACGTGGCTCCAGATCAAAGCGGCCAAGGACGGAG CATCCAGCAGCCCTGAGTCCGCCTCTCGCAGGGGCCAGCCCGCCA GCCCCTCTGCCCACATGGTCAGCCACAGTCACTCCCCCTCTGTGGT CTCC |
| 15 | Vgl14C amino acid | MIKVRNKTANGDCRRDPRERSRSPIERAVAPTMSLHGSHLYTSLPSL GLEQPLALTKNSLDASRPAGLSPTLTPGERQQNRPSVITCASAGARNC NLSHCPIAHSGCAAPGPASYRRPPSAATTCDPVVEEHFRRSLGKNYK EPEPAPNSVSITGSVDDHFAKALGDTWLQIKAAKDGASSSPESASRR GQPASPSAHMVSHSHSPSVVS |
| 16 | Vgl14D nucleotide | ATGAACAAGACTGCCAATGGAGACTGCCGCAGAGACCCCCGGGA GCGGAGCCGCAGCCCCATCGAGCGCGCTGTGGCCCCCACCATGA GCCTGCACGGCAGCCACCTGTACACCTCCCTCCCCAGCCTTGGCC TGGAGCAGCCCCTCGCACTGACCAAGAACAGCCTGGACGCCAGC AGGCCAGCCGGCCTCTCGCCCACACTGACCCCGGGGGAGCGGCA GCAGAACCGGCCCTCCGTGATCACCTGTGCCTCGGCTGGCGCCCG CAACTGCAACCTCTCGCACTGCCCCATCGCGCACAGCGGCTGTGC CGCGCCCGGGCCTGCCAGCTACCGGAGGCCACCGAGCGCTGCCA CCACCTGTGACCCCGTGGTGGAGGAGCATTTCCGCAGGAGCCTGG GCAAGAATTACAAGGAGCCCGAGCCGGCACCCAACTCCGTGTCC ATCACGGGCTCCGTGGACGACCACTTTGCCAAAGCTCTGGGTGAC ACGTGGCTCCAGATCAAAGCGGCCAAGGACGGAGCATCCAGCAG CCCTGAGTCCGCCTCTCGCAGGGGCCAGCCCGCCAGCCCCTCTGC CCACATGGTCAGCCACAGTCACTCCCCCTCTGTGGTCTCC |
| 17 | Vgl14D amino acid | MNKTANGDCRRDPRERSRSPIERAVAPTMSLHGSHLYTSLPSLGLEQ PLALTKNSLDASRPAGLSPTLTPGERQQNRPSVITCASAGARNCNLSH CPIAHSGCAAPGPASYRRPPSAATTCDPVVEEHFRRSLGKNYKEPEPA PNSVSITGSVDDHFAKALGDTWLQIKAAKDGASSSPESASRRGQPAS PSAHMVSHSHSPSVVS |

TABLE II-continued

Vgll4 sequences

| SEQ ID NO | Identity | Sequence |
|---|---|---|
| 18 | Vgll4E nucleotide | ATGACTGAGAATACGCATTTTGACAAAATCCCTGAGTCCTGTGCACTCAAAAGTTGGAGACATCCAGGTCTGCACCATGGCGAAGCTGCTCTCAGGGGAGAACCCAGAATACAGACCCTGCCGGTGGCCTCTGCCCTCAGCAGTCACCGCACCGGCCCTCCCCCAATCAGCCCCAGCAAGAGGAAGTTCAGCATGGAGCCAGGTGACGAGGACCTAGACTGTGACAACGACCACGTCTCCAAAATGAGTCGCATCTTCAACCCCCATCTGAACAAGACTGCCAATGGAGACTGCCGCAGAGACCCCCGGGAGCGGAGCCGCAGCCCCATCGAGCGCGCTGTGGCCCCCACCATGAGCCTGCACGGCAGCCACCTGTACACCTCCCTCCCCAGCCTTGGCCTGGAGCAGCCCCTCGCACTGACCAAGAACAGCCTGGACGCCAGCAGGCCAGCCGGCCTCTCGCCCACACTGACCCCGGGGGAGCGGCAGCAGAACCGGCCCTCCGTGATCACCTGTGCCTCGGCTGGCGCCCGCAACTGCAACCTCTCGCACTGCCCCATCGCGCACAGCGGCTGTGCCGCGCCCGGGCCTGCCAGCTACCGGAGGCCACCGAGCGCTGCCACCACCTGTGACCCCGTGGTGGAGGAGCATTTCCGCAGGAGCCTGGGCAAGAATTACAAGGAGCCCGAGCCGGCACCCAACTCCGTGTCCATCACGGGCTCCGTGGACGACCACTTTGCCAAAGCTCTGGGTGACACGTGGCTCCAGATCAAAGCGGCCAAGGACGGAGCATCCAGCAGCCCTGAGTCCGCCTCTCGCAGGGGCCAGCCCGCCAGCCCCTCTGCCCACATGGTCAGCCACAGTCACTCCCCCTCTGTGGTCTCC |
| 19 | Vgll4E amino acid | MTENTHFDKIPESCALKSWRHPGLHHGEAALRGEPRIQTLPVASALSSHRTGPPPISPSKRKFSMEPGDEDLDCDNDHVSKMSRIFNPHLNKTANGDCRRDPRERSRSPIERAVAPTMSLHGSHLYTSLPSLGLEQPLALTKNSLDASRPAGLSPTLTPGERQQNRPSVITCASAGARNCNLSHCPIAHSGCAAPGPASYRRPPSAATTCDPVVEEHFRRSLGKNYKEPEPAPNSVSITGSVDDHFAKALGDTWLQIKAAKDGASSSPESASRRGQPASPSAHMVSHSHSPSVVS |
| 20 | Vgll4F nucleotide | ATGGAGCCAGGTGACGAGGACCTAGACTGTGACAACGACCACGTCTCCAAAATGAGTCGCATCTTCAACCCCCATCTGAACAAGACTGCCAATGGAGACTGCCGCAGAGACCCCCGGGAGCGGAGCCGCAGCCCCATCGAGCGCGCTGTGGCCCCCACCATGAGCCTGCACGGCAGCCACCTGTACACCTCCCTCCCCAGCCTTGGCCTGGAGCAGCCCCTCGCACTGACCAAGAACAGCCTGGACGCCAGCAGGCCAGCCGGCCTCTCGCCCACACTGACCCCGGGGGAGCGGCAGCAGAACCGGCCCTCCGTGATCACCTGTGCCTCGGCTGGCGCCCGCAACTGCAACCTCTCGCACTGCCCCATCGCGCACAGCGGCTGTGCCGCGCCCGGGCCTGCCAGCTACCGGAGGCCACCGAGCGCTGCCACCACCTGTGACCCCGTGGTGGAGGAGCATTTCCGCAGGAGCCTGGGCAAGAATTACAAGGAGCCCGAGCCGGCACCCAACTCCGTGTCCATCACGGGCTCCGTGGACGACCACTTTGCCAAAGCTCTGGGTGACACGTGGCTCCAGATCAAAGCGGCCAAGGACGGAGCATCCAGCAGCCCTGAGTCCGCCTCTCGCAGGGGCCAGCCCGCCAGCCCCTCTGCCCACATGGTCAGCCACAGTCACTCCCCCTCTGTGGTCTCC |
| 21 | Vgll4F amino acid | MEPGDEDLDCDNDHVSKMSRIFNPHLNKTANGDCRRDPRERSRSPIERAVAPTMSLHGSHLYTSLPSLGLEQPLALTKNSLDASRPAGLSPTLTPGERQQNRPSVITCASAGARNCNLSHCPIAHSGCAAPGPASYRRPPSAATTCDPVVEEHFRRSLGKNYKEPEPAPNSVSITGSVDDHFAKALGDTWLQIKAAKDGASSSPESASRRGQPASPSAHMVSHSHSPSVVS |

At least six isoforms (A-F) of Vgll4 have been identified, referred to herein as Vgll4A, Vgll4B, Vgll4C, Vgll4D, Vgll4E, and Vgll4F, having amino acid sequences SEQ ID NO 11, SEQ ID NO 13, SEQ ID NO 15, SEQ ID NO 17, SEQ ID NO 19, and SEQ ID NO 21, respectively. These six isoforms are collectively included in the term Vgll4 as used herein. Also included herein is any nucleotide sequence that encodes any of the foregoing Vgll4 isoforms, including, without limitation, SEQ ID NO 10, SEQ ID NO: 12, SEQ ID NO 14, SEQ ID NO 16, SEQ ID NO 18, and SEQ ID NO: 20, including one or more codon substitution to any of the foregoing nucleotide sequences that nevertheless still encodes a Vg14 (e.g., A-F), owing to codon degeneracy. A construct as disclosed herein may include a nucleotide sequence encoding a Vgll4 peptide as disclosed herein with any cis-regulatory element as disclosed herein, including without limitation one or more Ucp1 enhancer and a Ucp1 promotor, including any variation thereof described above.

A Vgll4 protein may be of human Vgll4 (SEQ ID NO 11, SEQ ID NO 13, SEQ ID NO 15, SEQ ID NO 17, SEQ ID NO 19, or SEQ ID NO 21), or mouse or rat Vgll4, or a Vgll4 sequence having at least 90%, at least 95%, or at least 97.5% homology with any of the foregoing examples in Table II. In an example, A Vgll4 peptide may include one or more amino acid substitution (relative to the examples disclosed in Table II). In an example, a Vgll4 peptide may include 1, 2, 3, 4, 5, 6, 7, 8, 9, 10, 11, 12, 13, 14, 15, 16, 17, 18, 19, or 20 amino acid substitutions (relative to the examples disclosed in Table II). In an example, a Vgll4 peptide may have from 1 to 3 amino acid substitutions, or 2 amino acid substitutions, or 1 amino acid substitutions (relative to the examples disclosed in Table II). In an example, any of the foregoing amino acid substitutions may be outside of a TDU_1 and TDU_2 domain of the Vgll4 peptide.

In another example, a Vgll4 peptide may include two amino acid substitutions an a TDU domain, or two amino acid substitutions in each of two TDU domains. A TDU_1 domain has the amino acid sequence SEQ ID NO: 41. A TDU_2 domain has the amino acid sequence SEQ ID NO: 42. Each of SEQ ID NO 11, SEQ ID NO 13, SEQ ID NO 15, SEQ ID NO 17, SEQ ID NO 19, and SEQ ID NO 21 includes a TDU 1 domain with amino acid sequence SEQ ID NO: 41 and a TDU_2 domain with amino acid sequence SEQ ID NO: 42. In some examples, a TDU_1 domain may have an HF dipeptide amino acid sequence substituted with an AA dipeptide amino acid sequence, to yield the TDU_1 amino acid sequence SEQ ID NO: 43. In some examples, a TDU_2 domain may have an HF dipeptide amino acid sequence substituted with an AA dipeptide amino acid sequence, to yield the TDU_2 amino acid sequence SEQ ID NO: 44. A Vgll4 peptide may include a TDU_1 domain having an amino acid sequence of SEQ ID NO: 43 instead of an amino acid sequence of SEQ ID NO: 41. A Vgll4 peptide may include a TDU_2 domain having an amino acid sequence of SEQ ID NO: 44 instead of an amino acid sequence of SEQ ID NO: 42. A Vgll peptide may include a TDU_1 domain having an amino acid sequence of SEQ ID NO: 43 instead of an amino acid sequence of SEQ ID NO: 41 and include a TDU_2 domain having an amino acid sequence of SEQ ID NO: 44 instead of an amino acid sequence of SEQ ID NO: 42. A Vgll4 peptide (e.g., Vgll4A, Vgll4B, Vgll4C, Vgll4D, Vgll4E, or Vgll4F) having TDU domains with amino acid sequences SEQ ID NO: 43 and SEQ ID NO: 44 instead of SEQ ID NO: 41 and SEQ ID NO: 42 is referred to herein as a Vgll4-HF4A peptide.

At least six isoforms (A-F) of Vgll4-HF4A are disclosed herein, referred to herein as Vgll4A-HF4A, Vgll4B-HF4A, Vgll4C-HF4A, Vgll4D-HF4A, Vgll4E-HF4A, and Vgll4F-HF4A. Amino acid sequences, and non-limiting examples of nucleotide sequences encoding such Vgll4-HF4A peptide sequences, are shown in Table III.

TABLE III

Vgll4-HF4A sequences

| SEQ ID NO | Identity | Sequence |
|---|---|---|
| 22 | Vgll4A-HF4A nucleotide | ATGCTATTTATGAAGATGGACCTGTTGAACTATCAGTACTTGGAC AAGATGAACAACAATATCGGCATTCTGTGCTACGAAGGCGAAGC TGCTCTCAGGGGAGAACCCAGAATACAGACCCTGCCGGTGGCCTC TGCCCTCAGCAGTCACCGCACCGGCCCTCCCCCAATCAGCCCCAG CAAGAGGAAGTTCAGCATGGAGCCAGGTGACGAGGACCTAGACT GTGACAACGACCACGTCTCCAAAATGAGTCGCATCTTCAACCCCC ATCTGAACAAGACTGCCAATGGAGACTGCCGCAGAGACCCCCGG GAGCGGAGCCGCAGCCCCATCGAGCGCGCTGTGGCCCCCACCAT GAGCCTGCACGGCAGCCACCTGTACACCTCCCTCCCCAGCCTTGG CCTGGAGCAGCCCCTCGCACTGACCAAGAACAGCCTGGACGCCA GCAGGCCAGCCGGCCTCTCGCCCACACTGACCCCGGGGGAGCGG CAGCAGAACCGGCCCTCCGTGATCACCTGTGCCTCGGCTGGCGCC CGCAACTGCAACCTCTCGCACTGCCCCATCGCGCACAGCGGCTGT GCCGCGCCCGGGCCTGCCAGCTACCGGAGGCCACCGAGCGCTGC CACCACCTGTGACCCCGTGGTGGAGGAGGCAGCCCGCAGGAGCC TGGGCAAGAATTACAAGGAGCCCGAGCCGGCACCCAACTCCGTG TCCATCACGGGCTCCGTGGACGACGCAGCTGCCAAAGCTCTGGGT GACACGTGGCTCCAGATCAAAGCGGCCAAGGACGGAGCATCCAG CAGCCCTGAGTCCGCCTCTCGCAGGGGCCAGCCCGCCAGCCCCTC TGCCCACATGGTCAGCCACAGTCACTCCCCCTCTGTGGTCTCC |
| 23 | Vgll4A-HF4A amino acid | MLFMKMDLLNYQYLDKMNNNIGILCYEGEAALRGEPRIQTLPVASA LSSHRTGPPPISPSKRKFSMEPGDEDLDCDNDHVSKMSRIFNPHLNKT ANGDCRRDPRERSRSPIERAVAPTMSLHGSHLYTSLPSLGLEQPLALT KNSLDASRPAGLSPTLTPGERQQNRPSVITCASAGARNCNLSHCPIAH SGCAAPGPASYRRPPSAATTCDPVVEEAARRSLGKNYKEPEPAPNSV SITGSVDDAAAKALGDTWLQIKAAKDGASSSPESASRRGQPASPSAH MVSHSHSPSVVS |
| 24 | Vgll4B-HF4A nucleotide | ATGGAGACGCCATTGGATGTTTTGTCCAGGGCAGCATCTCTGGTG CATGCTGATGACGAAAAACGCGAAGCTGCTCTCAGGGGAGAACC CAGAATACAGACCCTGCCGGTGGCCTCTGCCCTCAGCAGTCACCG CACCGGCCCTCCCCCAATCAGCCCCAGCAAGAGGAAGTTCAGCAT GGAGCCAGGTGACGAGGACCTAGACTGTGACAACGACCACGTCT CCAAAATGAGTCGCATCTTCAACCCCCATCTGAACAAGACTGCCA ATGGAGACTGCCGCAGAGACCCCCGGGAGCGGAGCCGCAGCCCC ATCGAGCGCGCTGTGGCCCCCACCATGAGCCTGCACGGCAGCCAC CTGTACACCTCCCTCCCCAGCCTTGGCCTGGAGCAGCCCCTCGCA CTGACCAAGAACAGCCTGGACGCCAGCAGGCCAGCCGGCCTCTC GCCCACACTGACCCCGGGGGAGCGGCAGCAGAACCGGCCCTCCG TGATCACCTGTGCCTCGGCTGGCGCCCGCAACTGCAACCTCTCGC ACTGCCCCATCGCGCACAGCGGCTGTGCCGCGCCCGGGCCTGCCA GCTACCGGAGGCCACCGAGCGCTGCCACCACCTGTGACCCCGTGG TGGAGGAGGCAGCCCGCAGGAGCCTGGGCAAGAATTACAAGGAG CCCGAGCCGGCACCCAACTCCGTGTCCATCACGGGCTCCGTGGAC GACGCAGCTGCCAAAGCTCTGGGTGACACGTGGCTCCAGATCAA AGCGGCCAAGGACGGAGCATCCAGCAGCCCTGAGTCCGCCTCTC GCAGGGGCCAGCCCGCCAGCCCCTCTGCCCACATGGTCAGCCACA GTCACTCCCCCTCTGTGGTCTCC |

TABLE III-continued

Vgl14-HF4A sequences

| SEQ ID NO | Identity | Sequence |
|---|---|---|
| 25 | Vgl14B-HF4A peptide | METPLDVLSRAASLVHADDEKREAALRGEPRIQTLPVASALSSHRTG PPPISPSKRKFSMEPGDEDLDCDNDHVSKMSRIFNPHLNKTANGDCR RDPRERSRSPIERAVAPTMSLHGSHLYTSLPSLGLEQPLALTKNSLDA SRPAGLSPTLTPGERQQNRPSVITCASAGARNCNLSHCPIAHSGCAAP GPASYRRPPSAATTCDPVVEEAARRSLGKNYKEPEPAPNSVSITGSVD DAAAKALGDTWLQIKAAKDGASSSPESASRRGQPASPSAHMVSHSH SPSVVS |
| 26 | Vgl14C-HF4A nucleotide | ATGATTAAAGTGAGGAACAAGACTGCCAATGGAGACTGCCGCAG AGACCCCCGGGAGCGGAGCCGCAGCCCCATCGAGCGCGCTGTGG CCCCCACCATGAGCCTGCACGGCAGCCACCTGTACACCTCCCTCC CCAGCCTTGGCCTGGAGCAGCCCCTCGCACTGACCAAGAACAGCC TGGACGCCAGCAGGCCAGCCGGCCTCTCGCCCACACTGACCCCGG GGGAGCGGCAGCAGAACCGGCCCTCCGTGATCACCTGTGCCTCGG CTGGCGCCCGCAACTGCAACCTCTCGCACTGCCCCATCGCGCACA GCGGCTGTGCCGCGCCCGGGCCTGCCAGCTACCGGAGGCCACCG AGCGCTGCCACCACCTGTGACCCCGTGGTGGAGGAGGCAGCCCG CAGGAGCCTGGGCAAGAATTACAAGGAGCCCGAGCCGGCACCCA ACTCCGTGTCCATCACGGGCTCCGTGGACGACGCAGCTGCCAAAG CTCTGGGTGACACGTGGCTCCAGATCAAAGCGGCCAAGGACGGA GCATCCAGCAGCCCTGAGTCCGCCTCTCGCAGGGGCCAGCCCGCC AGCCCTCTGCCCACATGGTCAGCCACAGTCACTCCCCCTCTGTG GTCTCC |
| 27 | Vgl14C-HF4A amino acid | MIKVRNKTANGDCRRDPRERSRSPIERAVAPTMSLHGSHLYTSLPSL GLEQPLALTKNSLDASRPAGLSPTLTPGERQQNRPSVITCASAGARNC NLSHCPIAHSGCAAPGPASYRRPPSAATTCDPVVEEAARRSLGKNYK EPEPAPNSVSITGSVDDAAAKALGDTWLQIKAAKDGASSSPESASRR GQPASPSAHMVSHSHSPSVVS |
| 28 | Vgl14D-HF4A nucleotide | ATGAACAAGACTGCCAATGGAGACTGCCGCAGAGACCCCCGGGA GCGGAGCCGCAGCCCCATCGAGCGCGCTGTGGCCCCCACCATGA GCCTGCACGGCAGCCACCTGTACACCTCCCTCCCCAGCCTTGGCC TGGAGCAGCCCCTCGCACTGACCAAGAACAGCCTGGACGCCAGC AGGCCAGCCGGCCTCTCGCCCACACTGACCCCGGGGGAGCGGCA GCAGAACCGGCCCTCCGTGATCACCTGTGCCTCGGCTGGCGCCCG CAACTGCAACCTCTCGCACTGCCCCATCGCGCACAGCGGCTGTGC CGCGCCCGGGCCTGCCAGCTACCGGAGGCCACCGAGCGCTGCCA CCACCTGTGACCCCGTGGTGGAGGAGGCAGCCCGCAGGAGCCTG GGCAAGAATTACAAGGAGCCCGAGCCGGCACCCAACTCCGTGTC CATCACGGGCTCCGTGGACGACGCAGCTGCCAAAGCTCTGGGTGA CACGTGGCTCCAGATCAAAGCGGCCAAGGACGGAGCATCCAGCA GCCCTGAGTCCGCCTCTCGCAGGGGCCAGCCCGCCAGCCCCTCTG CCCACATGGTCAGCCACAGTCACTCCCCCTCTGTGGTCTCC |
| 29 | Vgl14D-HF4A amino acid | MNKTANGDCRRDPRERSRSPIERAVAPTMSLHGSHLYTSLPSLGLEQ PLALTKNSLDASRPAGLSPTLTPGERQQNRPSVITCASAGARNCNLSH CPIAHSGCAAPGPASYRRPPSAATTCDPVVEEAARRSLGKNYKEPEP APNSVSITGSVDDAAAKALGDTWLQIKAAKDGASSSPESASRRGQPA SPSAHMVSHSHSPSVVS |
| 30 | Vgl14E-HF4A nucleotide | ATGACTGAGAATACGCATTTTGACAAAATCCCTGAGTCCTGTGCA CTCAAAAGTTGGAGACATCCAGGTCTGCACCATGGCGAAGCTGCT CTCAGGGGAGAACCCAGAATACAGACCCTGCCGGTGGCCTCTGCC CTCAGCAGTCACCGCACCGGCCCTCCCCCAATCAGCCCCAGCAAG AGGAAGTTCAGCATGGAGCCAGGTGACGAGGACCTAGACTGTGA CAACGACCACGTCTCCAAAATGAGTCGCATCTTCAACCCCCATCT GAACAAGACTGCCAATGGAGACTGCCGCAGAGACCCCCGGGAGC GGAGCCGCAGCCCCATCGAGCGCGCTGTGGCCCCCACCATGAGCC TGCACGGCAGCCACCTGTACACCTCCCTCCCCAGCCTTGGCCTGG AGCAGCCCCTCGCACTGACCAAGAACAGCCTGGACGCCAGCAGG CCAGCCGGCCTCTCGCCCACACTGACCCCGGGGGAGCGGCAGCA GAACCGGCCCTCCGTGATCACCTGTGCCTCGGCTGGCGCCCGCAA CTGCAACCTCTCGCACTGCCCCATCGCGCACAGCGGCTGTGCCGC GCCCGGGCCTGCCAGCTACCGGAGGCCACCGAGCGCTGCCACCA CCTGTGACCCCGTGGTGGAGGAGGCAGCCCGCAGGAGCCTGGGC AAGAATTACAAGGAGCCCGAGCCGGCACCCAACTCCGTGTCCATC ACGGGCTCCGTGGACGACGCAGCTGCCAAAGCTCTGGGTGACAC GTGGCTCCAGATCAAAGCGGCCAAGGACGGAGCATCCAGCAGCC CTGAGTCCGCCTCTCGCAGGGGCCAGCCCGCCAGCCCCTCTGCCC ACATGGTCAGCCACAGTCACTCCCCCTCTGTGGTCTCC |

TABLE III-continued

Vgll4-HF4A sequences

| SEQ ID NO | Identity | Sequence |
|---|---|---|
| 31 | Vgll4E-HF4A amino acid | MTENTHFDKIPESCALKSWRHPGLHHGEAALRGEPRIQTLPVASALS SHRTGPPPISPSKRKFSMEPGDEDLDCDNDHVSKMSRIFNPHLNKTA NGDCRRDPRERSRSPIERAVAPTMSLHGSHLYTSLPSLGLEQPLALTK NSLDASRPAGLSPTLTPGERQQNRPSVITCASAGARNCNLSHCPIAHS GCAAPGPASYRRPPSAATTCDPVVEEAARRSLGKNYKEPEPAPNSVS ITGSVDDAAAKALGDTWLQIKAAKDGASSSPESASRRGQPASPSAH MVSHSHSPSVVS |
| 32 | Vgll4F-HF4A nucleotide | ATGGAGCCAGGTGACGAGGACCTAGACTGTGACAACGACCACGT CTCCAAAATGAGTCGCATCTTCAACCCCCATCTGAACAAGACTGC CAATGGAGACTGCCGCAGAGACCCCCGGGAGCGGAGCCGCAGCC CCATCGAGCGCGCTGTGGCCCCCACCATGAGCCTGCACGGCAGCC ACCTGTACACCTCCCTCCCCAGCCTTGGCCTGGAGCAGCCCCTCG CACTGACCAAGAACAGCCTGGACGCCAGCAGGCCAGCCGGCCTC TCGCCCACACTGACCCCGGGGGAGCGGCAGCAGAACCGGCCCTC CGTGATCACCTGTGCCTCGGCTGGCGCCCGCAACTGCAACCTCTC GCACTGCCCCATCGCGCACAGCGGCTGTGCCGCGCCCGGGCCTGC CAGCTACCGGAGGCCACCGAGCGCTGCCACCACCTGTGACCCCGT GGTGGAGGAGGCAGCCCGCAGGAGCCTGGGCAAGAATTACAAGG AGCCCGAGCCGGCACCCAACTCCGTGTCCATCACGGGCTCCGTGG ACGACGCAGCTGCCAAAGCTCTGGGTGACACGTGGCTCCAGATCA AAGCGGCCAAGGACGGAGCATCCAGCAGCCCTGAGTCCGCCTCT CGCAGGGGCCAGCCCGCCAGCCCCTCTGCCCACATGGTCAGCCAC AGTCACTCCCCCTCTGTGGTCTCC |
| 33 | Vgll4F-HF4A amino acid | MEPGDEDLDCDNDHVSKMSRIFNPHLNKTANGDCRRDPRERSRSPIE RAVAPTMSLHGSHLYTSLPSLGLEQPLALTKNSLDASRPAGLSPTLTP GERQQNRPSVITCASAGARNCNLSHCPIAHSGCAAPGPASYRRPPSA ATTCDPVVEEAARRSLGKNYKEPEPAPNSVSITGSVDDAAAKALGDT WLQIKAAKDGASSSPESASRRGQPASPSAHMVSHSHSPSVVS |

As disclosed herein, a Vgll4-HF4A peptide may have an amino acid sequence of s SEQ ID NO 23, SEQ ID NO 25, SEQ ID NO 27, SEQ ID NO 29, SEQ ID NO 31, or SEQ ID NO 33. These six isoforms are collectively included in the term Vgll4-HF4A as used herein. Also included herein is any nucleotide sequence that encodes any of the foregoing Vgll4 isoforms, including, without limitation, SEQ ID NO 22, SEQ ID NO: 24, SEQ ID NO 26, SEQ ID NO 28, SEQ ID NO 30, and SEQ ID NO: 32, including one or more codon substitution to any of the foregoing nucleotide sequences that nevertheless still encodes a Vg14-HF4A (e.g., A-F), owing to codon degeneracy. A construct as disclosed herein may include a nucleotide sequence encoding a Vgll4-HF4A peptide as disclosed herein with any cis-regulatory element as disclosed herein, including without limitation one or more Ucp1 enhancer and a Ucp1 promotor, including any variation thereof described above.

A Vgll4-HF4A protein may be a human Vgll4, or mouse or rat Vgll4, bearing an HF to AA substitution in its TDU domains, or a Vgll4-HF4A sequence having at least 90%, at least 95%, or at least 97.5% homology with any of the foregoing examples in Table III. In an example, a Vgll4-HF4A peptide may include one or more amino acid substitution (relative to the examples disclosed in Table III) outside a TDU_1 and TDU_2 domain. In an example, a Vgll4-HF4A peptide may include 1, 2, 3, 4, 5, 6, 7, 8, 9, 10, 11, 12, 13, 14, 15, 16, 17, 18, 19, or 20 amino acid substitutions (relative to sequences disclosed in Table III) outside a TDU_1 and TDU_2 domain. In an example, a Vgll4-HF4A peptide may have from 1 to 3 amino acid substitutions, or 2 amino acid substitutions, or 1 amino acid substitution (relative to sequences disclosed in Table III) outside a TDU_1 and TDU_2 domain.

In some examples, an intron may be included between a cis-regulatory element and a gene encoding Vgll4. In some examples, an intron may enhance or promote transcription or promote stability of an RNA transcript. Other examples do not include an intron. Various intronic sequences are known by skilled artisans to be able to be included in recombinant constructs for promoting gene expression, any of which could be included in a construct as disclosed herein. In an example, an intron of SEQ ID NO: 34 (a chimeric intron of human b-globin and immunoglobulin heavy chain genes) may be included, or a sequence having at least 90%, at least 95%, or at least 97.5% sequence homology therewith.

A summary of aspects of a construct including a cis regulatory element and a Vgll4-encoding nucleotide sequence, and a cis regulatory element and a Vgll4-HF4A-encoding nucleotide sequence, as disclosed herein are shown in Tables IV and V, respectively.

TABLE IV

Vgll4 constructs

| cis-Regulatory Elements | | Optional intron | Vgll4 |
|---|---|---|---|
| Enhancer sequences | Promoter sequences | SEQ ID NO: 34 | Amino acid sequences: |
| SEQ ID NO: 1 | SEQ ID NO: 2 | GTAAGTATCAAGG | SEQ ID NO: 11 |
| SEQ ID NO: 4 | SEQ ID NO: 5 | TTACAAGACAGGT | SEQ ID NO: 13 |

TABLE IV-continued

Vgll4 constructs

| cis-Regulatory Elements | | Optional intron | Vgll4 |
|---|---|---|---|
| SEQ ID NO: 7 | SEQ ID NO: 8 | TTAAGGAGACCAA | SEQ ID NO: 15 |
| | | TAGAAACTGGGCT | SEQ ID NO: 17 |
| | | TGTCGAGACAGAG | SEQ ID NO: 19 |
| | | AAGACTCTTGCGTT | SEQ ID NO: 21 |
| Enhancer-promoter sequences: | | TCTGATAGGCACCT | Nucleotide sequences: |
| SEQ ID NO: 3 | | ATTGGTCTTACTGA | SEQ ID NO: 10 |
| SEQ ID NO: 6 | | CATCCACTTTGCCT | SEQ ID NO: 12 |
| SEQ ID NO: 9 | | TTCTCTCCACAG | SEQ ID NO: 14 |
| SEQ ID NO: 16 | | | |
| SEQ ID NO: 18 | | | |
| SEQ ID NO: 20 | | | |

TABLE V

Vgll4-HF4A constructs

| cis-Regulatory Elements | | Optional intron | Vgll4-HF4A |
|---|---|---|---|
| Enhancer sequences | Promoter sequences | SEQ ID NO: 34 | Amino acid sequences: |
| SEQ ID NO: 1 | SEQ ID NO: 2 | GTAAGTATCAAGG | SEQ ID NO: 23 |
| SEQ ID NO: 4 | SEQ ID NO: 5 | TTACAAGACAGGT | SEQ ID NO: 25 |
| SEQ ID NO: 7 | SEQ ID NO: 8 | TTAAGGAGACCAA | SEQ ID NO: 27 |
| | | TAGAAACTGGGCT | SEQ ID NO: 29 |
| | | TGTCGAGACAGAG | SEQ ID NO: 31 |
| | | AAGACTCTTGCGTT | SEQ ID NO: 33 |
| Enhancer-promoter sequences: | | TCTGATAGGCACCT | Nucleotide sequences: |
| SEQ ID NO: 3 | | ATTGGTCTTACTGA | SEQ ID NO: 22 |
| SEQ ID NO: 6 | | CATCCACTTTGCCT | SEQ ID NO: 24 |
| SEQ ID NO: 9 | | TTCTCTCCACAG | SEQ ID NO: 26 |
| SEQ ID NO: 28 | | | |
| SEQ ID NO: 30 | | | |
| SEQ ID NO: 32 | | | |

A construct as disclosed herein may include a cis regulatory element and a nucleotide sequence encoding a Vgll4 or Vgll4-HF4A peptide. A cis regulatory element may include, for example, any one or more of enhancer sequence SEQ ID NO: 1, SEQ ID NO: 4, and SEQ ID NO: 7, and any one of promoter sequence SEQ ID NO: 2, SEQ ID NO: 5, and SEQ ID NO: 8. All permutations of the foregoing are expressly contemplated and included in the present disclosure. In an example, a cis-regulatory element may include 2, 3, or 4 enhancer sequences each independently selected from SEQ ID NO: 1, SEQ ID NO: 4, and SEQ ID NO: 7. Examples of cis regulatory elements include SEQ ID NO: 3, SEQ ID NO: 6, and SEQ ID NO: 9.

A Vgll4 peptide encoded by a Vgll4 peptide-encoding nucleotide sequence of a construct may include, for example, any of SEQ ID NO: 11, SEQ ID NO: 13, SEQ ID NO: 15, SEQ ID NO: 17, SEQ ID NO: 19, and SEQ ID NO: 21, or any variation thereof as further explained above. Examples include SEQ ID NO: 10, SEQ ID NO: 12, SEQ ID NO: 14, SEQ ID NO: 16, SEQ ID NO: 18, and SEQ ID NO: 20. Vgll4-HF4A peptide encoded by a Vgll4-HF4A peptide-encoding nucleotide sequence of a construct may include, for example, any of SEQ ID NO: 23, SEQ ID NO: 25, SEQ ID NO: 27, SEQ ID NO: 29, SEQ ID NO: 31, and SEQ ID NO: 31, or any variation thereof as further explained above. Examples include SEQ ID NO: 22, SEQ ID NO: 24, SEQ ID NO: 26, SEQ ID NO: 28, SEQ ID NO: 30, and SEQ ID NO: 32. A construct may include any cis regulatory element as disclosed herein and any Vgll4- or Vgll-4HF4A-encoding nucleotide sequence as disclosed herein. Optionally, a construct may also include an intron between a cis regulatory element and a Vgll4- or Vgll4-HF4A-encoding nucleotide sequence. A non-limiting example of an optional intron is SEQ ID NO: 34. In other examples, nucleotides other than an intron or having an intronic nucleotide sequence other than SEQ ID NO: 34 may be included in a construct between a cis regulatory element and a Vgll4- or Vgll4-HF4A-encoding nucleotide sequence. An example of a Vgll4A construct is SEQ ID NO: 35 and an example of a Vgll4-HF4A construct is SEQ ID NO: 36.

A cell may be transfected with a construct as disclosed above by various methods, such as chemical transfection, electroporation, impalefaction, gene gun transfection, or viral vector mediated gene transfer, or any other method known to skilled persons in the relevant field. In an example, a Vgll4 gene with associated Ucp1 cis-regulatory element is packaged in a viral vector for cellular transfection. Viral vector in this case refers to a viral-like particle that contains or includes a payload gene construct or cassette capable of attaching to a cell and delivering the payload into the cell. In some examples, a viral vector may be of a type wherein a payload, once introduced into a transfected cell, integrates into the cell's genomic DNA, though such genomic integration is not an essential feature of a viral vector as disclosed herein. Viral vector may also refer to a gene sequence including a gene construct or cassette structured for inclusion in a viral-like particle. Examples of viral vectors include retroviruses, lentiviruses, adenoviruses, and adeno-associated viruses (AAV). Several serotypes of AAV vectors are useful for cellular transfection, including any of serotypes 1, 2, 3, 4, 5, 6, 7, 8, 9, 10, and 11, or subtypes thereof. Sequences for such AAV serotypes are known and may be found in publicly accessible databases, as are methods of packaging a construct of interest in viral vector particles for cellular transfection and promotion of construct expression in transfected cells.

An AAV vector includes sequences bounding a payload construct referred to as inverted terminal repeats (ITRs). ITR sequences are involved in transcription of AAV genome, encapsulation of payload in a vector particle, genome multiplication for particle generation, and integration into host genome. A cassette, construct, transgene, payload, etc., placed between ITRs of an AAV vector may promote production of an AAV vector and/or expression of transfected gene within cells. In an example, a Ucp1 cis-regulatory element neighboring a nucleotide sequence encoding a Vgll4 or Vgll4-HFA peptide may be placed between ITRs and used for generation of an AAV particle, wherein said particle may be contacted with cells of an organism to transfect them with such construct. An example includes an AAV9 serotype AAV containing such construct, though other serotypes may also be used.

In some cases a reporter gene may be used or included in a construct to verify expression of a construct gene included in a vector or for testing tissue- or cell-type specific expression of a gene under control of a given cis-regulatory element. Numerous reporter genes are known and have been widely used in the relevant field. A non-limiting list of examples includes a green fluorescent protein (for example, having an amino acid sequence of SEQ ID NO: 37, encoded for by a nucleotide sequence of SEQ ID NO: 38 or any other nucleotide sequence as may encode an amino acid sequence of SEQ ID NO: 37 according to principles codon degeneracy), a yellow fluorescent protein, a red fluorescent protein, a blue fluorescent protein, a luciferase protein, a beta-galactosidase protein, a glutathione S-transferase protein, a chloramphenicol acetyltransferase protein, and any combination of two or more of the foregoing. Other reporters may also be included. In other examples, no reporter is included. By detecting expression of a reporter protein, the ability of a given cis-regulatory element, or viral vector, to promote transfection and/or expression in various cell ad tissue types can be evaluated. A reporter protein sequence may occur immediately before the N-terminal or immediately after the C-terminal amino acid of a Vgll4 or Vgll4-HF4A peptide as disclosed herein, or may be separated by and one or more amino acids from the N- or C-terminal amino acid of a Vgll4 or Vgll4-HF4A peptide. A construct may include any nucleotide sequence for encoding any reporter protein. A non-limiting example of a Vgll4 construct including a sequence encoding a GFP-encoding reported protein is SEQ ID NO: 39. In another non-limiting example, SEQ ID NO: 39 may be modified to replace SEQ ID NO: 41 therein and SEQ ID NO: 42 therein with SEQ ID NO: 43 and SEQ ID NO: 44, respectively, to encode a Vgll4-HF4A and a GFP reporter protein.

A viral vector or viral-like particle, such as an AAV vector, can be injected into an organism, such as subcutaneously, intramuscularly, intravenously, intraperitoneally, or by other methods for introduction of the vector into the organism for contact with cells thereof. A vector may contact various different cell and tissue types and transfect them. However, inclusion of a cell- or tissue-specific cis-regulatory element (enhancer, promotor, or both) may restrict expression of the transfected gene to a given cell or tissue type or types, wherein the construct is not transcribed or is otherwise dormant or at most barely or minimally expressed in other cell types. As explained above, a cis-regulatory element may include elements that are known or believed to drive expression in adipocytes, or fat cells, specifically, including in specific subtypes of fat cells, such as predominantly in BAT cells. However, it is not necessary that expression be limited absolutely to a given cell type, including only in BAT cells, even under control of a Ucp1 cis-regulatory element. For example, although Ucp1 expression is believed to be restricted to mature BAT cells, it is possible that other cell types may from time to time express a construct whose expression is influenced by a neighboring cis-regulatory element such as a Ucp1 enhancer, promoter, or both. Surprisingly, in some circumstances, as disclosed herein, a Ucp1 cis-regulatory element may include expression in liver cells in addition to BAT cells.

In an example, contacting the cells of an organism with a nucleotide sequence including a Ucp1 cis-regulatory element and a coding sequence for a Vgll4 protein or variant may increase BAT volume, lower WAT volume, increase a ratio of BAT volume to WAT volume, or any combination of the foregoing, even if Vgll4 expression under control of the cis-regulatory element is not strictly limited to BAT cells containing the transgene. In another example, a construct may In another example, transfecting cells of an organism with a nucleotide sequence including a Ucp1 cis-regulatory element and a coding sequence for a Vgll4 protein or variant may reduce a volume of adipose tissue of the organism. In another example, transfecting cells of an organism with a nucleotide sequence including a Ucp1 cis-regulatory element and a coding sequence for a Vgll4 protein or variant may reduce a mass ratio BAT to body weight of the organism.

In another example, disclosed herein is a method for prevention or treatment of obesity, by transfecting cells of an organism with any of the foregoing constructs disclosed herein including a cis-regulatory element and nucleotide sequence encoding a Vgll4 peptide or a Vgll4-HF4A peptide.

In another example, transfecting cells of an organism with a nucleotide sequence including a Ucp1 cis-regulatory element and a coding sequence for a Vgll4 protein or variant may reduce a liver volume, liver weight, intrahepatic fat content, or any combination of two or more of the foregoing, of the organism. An intrahepatic fat content of at least 5% of liver weight is referred to as hepatic steatosis. Obesity, or risk of developing obesity, such as genetic or life-style factors (e.g., high-calorie or high-fat diet, low exercise or caloric burn rate, sedentary lifestyle, etc.), are risk factors for developing elevated hepatic steatosis. Obesity may be defined as having a body mass index (BMI) of 30 or higher. An example of a risk factor for developing obesity may be having a BMI of from 25 to 29, which is considered being overweight. Prolonged hepatic steatosis is is a risk factor for disorders including liver metabolic dysfunction, inflammation, and advanced forms of nonalcoholic fatty liver disease. Disclosed herein is a method for prevention or treatment of hepatic steatosis, by transfecting cells of an organism with any of the foregoing constructs disclosed herein including a cis-regulatory element and nucleotide sequence encoding a Vgll4 peptide or a Vgll4-HF4A peptide.

In another example, transfecting cells of an organism with a nucleotide sequence including a Ucp1 cis-regulatory element and a coding sequence for a Vgll4 protein or variant may reduce or minimize blood glucose levels or a rise in glucose levels or duration of such rise in an organism. Obesity is a risk factor for diabetes, which includes pathological dysregulation of glucose levels, specifically pathological elevations in serum glucose levels or pathologically elevated duration of elevated serum glucose levels such as following calorie intake such as a meal. In an example, a rise in serum glucose may be measured following administration of a glucose challenge (i.e., consuming a glucose solution). Normally, a rise in serum glucose follows such a challenge, which rise then returns to baseline or near baseline. In individuals with diabetes, however, glucose may rise pathologically higher and/or for a pathologically longer duration than in individuals without diabetes. For individuals with diabetes or at risk for developing diabetes (e.g., family history, genetic or other biomarker-evinced predisposition, obesity, etc.), a treatment for preventing pathological rise in serum glucose levels, or a pathological extension of a rise in serum glucose levels, following a meal or a glucose challenge is advantageous. An example in accordance with the present disclosure includes reducing or minimizing blood glucose levels or a rise in glucose levels in an organism by contacting an organism with the construct, such as by transfecting cells of an organism with the construct. An example in accordance with the present disclosure includes preventing development of a pathologically high rise in blood glucose levels or a pathologically high duration of a rise in blood glucose levels in an organism with diabetes or at risk for developing diabetes by contacting an organism with the construct, such as by transfecting cells of the organism. The organism may be an obese person, or a person at risk of developing obesity, or a person diagnosed with diabetes, or a person at risk of developing diabetes. Accordingly, an example disclosed herein includes a method for prevention or treatment of diabetes, by transfecting cells of an organism with any of the foregoing constructs disclosed herein including a cis-regulatory element and nucleotide sequence encoding a Vgll4 peptide or a Vgll4-HF4A peptide.

In an example, also disclosed is increasing expression of mitochondrial genes, such as mitochondrial genes involved in mitochondrial respiration, in an organism by contacting an organism with the construct, such as by transfecting cells of an organism with the construct. In an example, also disclosed is decreasing expression of genes that promote lipogenesis, in an organism by contacting an organism with the construct, such as by transfecting cells of an organism with the construct. Increasing mitochondrial genes that promote mitochondrial respiration, or decreasing expression of genes involved in lipogenesis, such as in BAT or liver cells of an organism transfected with a construct as disclosed herein (e.g., including a Ucp1 cis regulatory element and a nucleotide sequence encoding a Vgll4- or Vgll4-HFA-encoding nucleotide, as disclosed herein), may include advantageously promote BAT levels, decrease lipogenesis in adipose cells, decrease hepatic steatosis, or any combination of the foregoing.

As disclosed herein, in an example, contacting cells of an organism with a nucleotide sequence including a Ucp1 cis-regulatory element neighboring a Vgll4 coding sequence surprisingly increases BAT volume, i.e. the volume occupied by BAT cells. In another example, contacting cells of an organism with a nucleotide sequence including a Ucp1 cis-regulatory element neighboring a Vgll4 coding sequence surprisingly decreases WAT volume. In another example, contacting cells of an organism with a nucleotide sequence including a Ucp1 cis-regulatory element neighboring a Vgll4 coding sequence surprisingly increases a ration of BAT volume to WAT volume. An increase in BAT by driving Vgll4 expression under control of a Ucp1 cis-regulatory element, known to increase expression of a neighboring gene in BAT cells, is particularly unexpected given that increased Vgll4 expression is known to promote apoptosis or otherwise have anti-tumor cell effects, unlike other members of the Vgll family. By comparison, Vgll3 levels are increased in WAT cells in obese mice, suggesting that Vgll3 may promote WAT cells, whereas over-expression of Vgll3 inhibits adipogenesis overall. U.S. Pat. No. 8,852,939.

As further disclosed herein, in an example, contacting cells of an organism with a nucleotide sequence including a Ucp1 cis-regulatory element neighboring a Vgll4 coding sequence or a Vgll4-HF4A sequence in some cases may promote expression of Vgll4 or Vgll4-HF4A respectively, in liver.

In another example, contacting cells of an organism with a nucleotide sequence including a Ucp1 cis-regulatory element neighboring a Vgll4-HF4A coding sequence may surprisingly decreases adipose tissue volume. In an example, a volume of BAT is decreased. Without limiting the present disclosure to any particular mechanism of action, decreased volume of BAT following transfection with such a construct may be related to stimulation of expression of mitochondrial genes involved in mitochondrial respiration, inhibition of expression of genes involved in lipogenesis, an inhibition of lipogenesis, or any combination of two or more of the foregoing, in BAT, caused by the transfection. In another example, hepatic steatosis is decreased. Without limiting the present disclosure to any particular mechanism of action, decreased hepatic steatosis following transfection with such a construct may be related to stimulation of expression of mitochondrial genes involved in mitochondrial respiration, inhibition of expression of genes involved in lipogenesis, an inhibition of lipogenesis, or any combination of two or more of the foregoing, in liver, caused by the transfection.

EXAMPLES

The following examples are intended to illustrate particular embodiments of the present disclosure, but are by no means intended to limit the scope thereof Example 1: A Ucp1 Cis-Regulatory Element Drives Expression in BAT when Transfection Occurs During Early Development FIG. 1 shows examples of polynucleotides in accordance with certain aspects of the present disclosure. The example includes a cis-regulatory element (BCE) including a mouse Ucp1 enhancer and mouse Ucp1 promoter upstream of a coding sequence of a reporter protein (either a green fluorescent protein (GFP) of firefly luciferase (Luci)). In these examples, a chimeric intron of human b-globin and immunoglobulin heavy chain genes is included between the BCE and the reporter sequence. Inclusion of an intron may increase expression of the payload gene sequence, here the reporter constructs. Also included at the 5' and 3' ends, flanking the BCE and reporter, are inverted terminal repeat (ITR) sequences. Adeno-associated viral vectors were synthesized incorporating constructs as illustrated for determining an ability of BCE to drive expression of a downstream coding sequence. In an example, adeno-associated viral vectors of serotype 9 (AAV9) were constructed carrying constructs as illustrated in FIG. 1. Constructs include a BCE having a sequence of SEQ ID NO: 3 and an intron of SEQ ID NO: 34.

Figure 2:
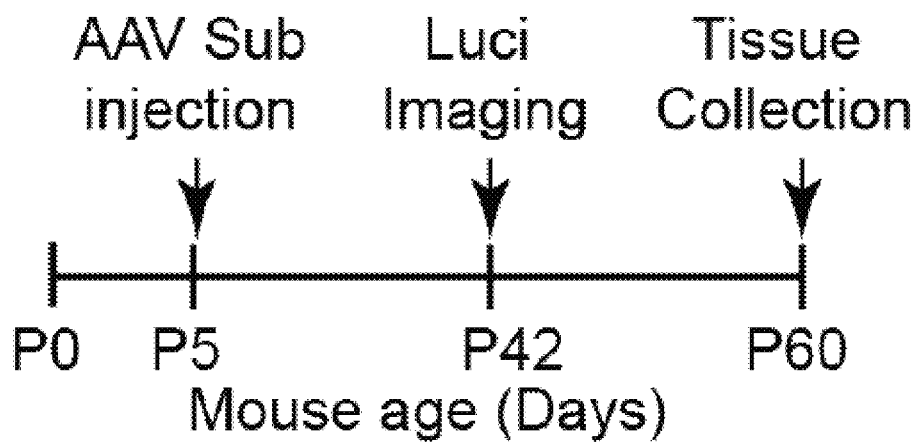
FIG. 2 shows timing of vector administration and expression measurement in accordance with aspects of the present disclosure.
Figure 3:
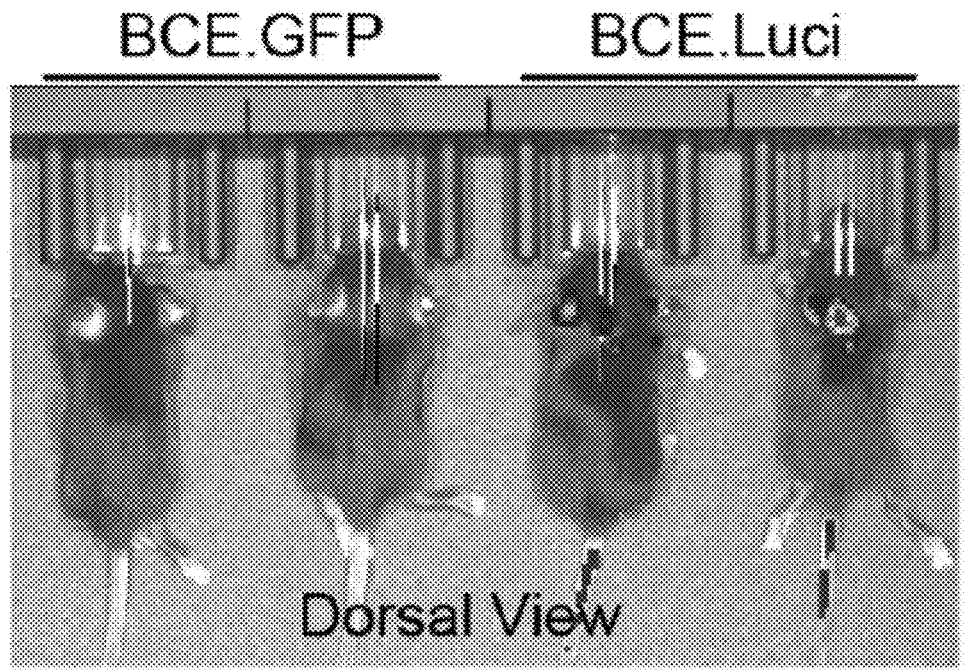
FIG. 3 shows representative bioluminescence images of a dorsal view of mice administered a viral vector in accordance with aspects of the present disclosure.
Figure 4:
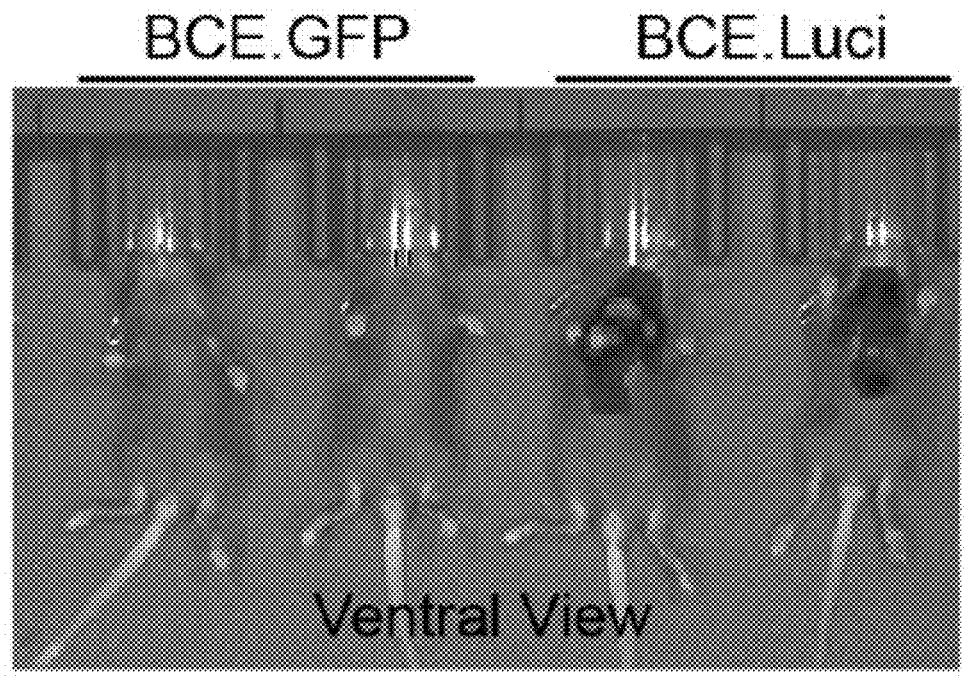
FIG. 4 shows representative bioluminescence images of a ventral view of mice administered a viral vector in accordance with aspects of the present disclosure.
Figure 5:
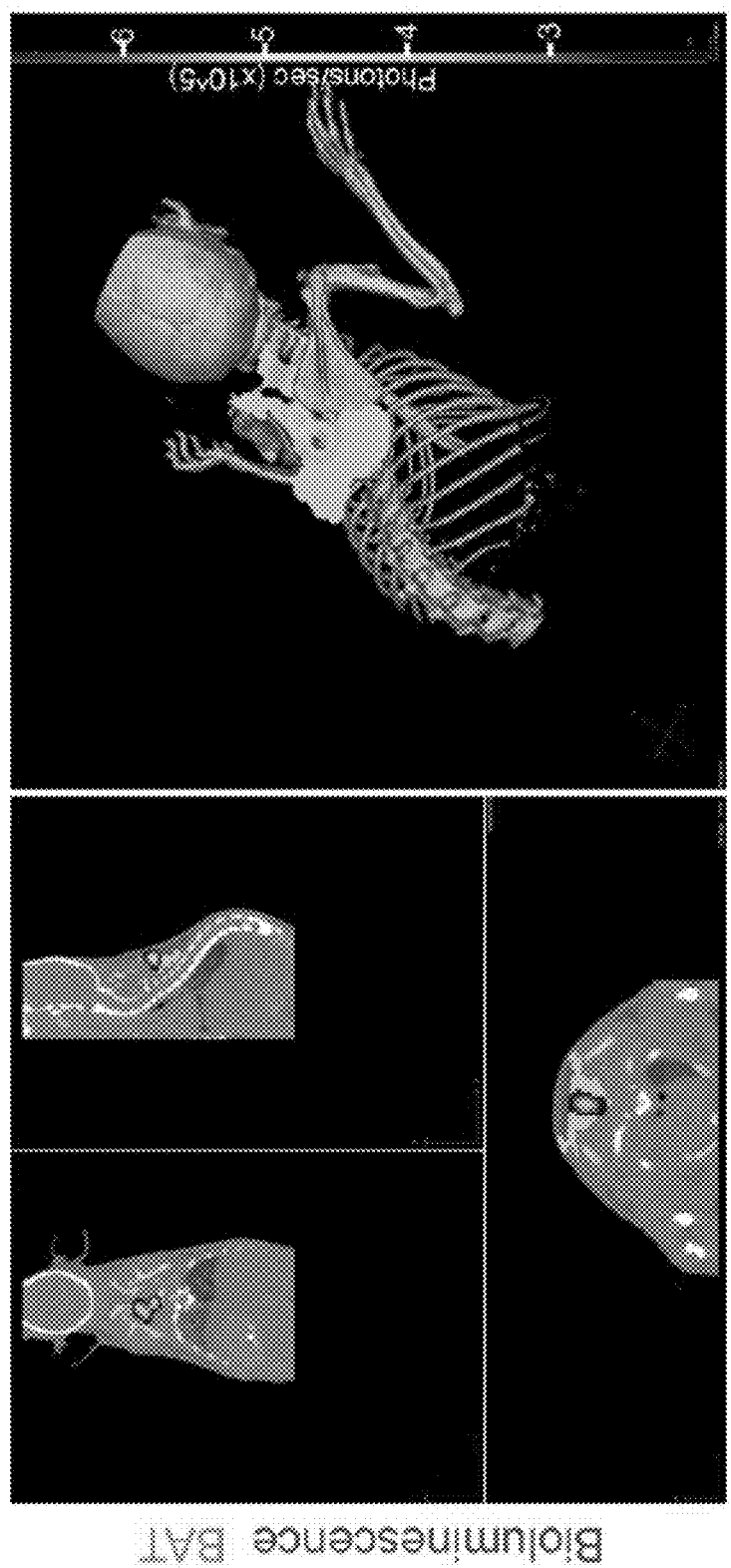
FIG. 5 shows bioluminescence signal origin following viral vector administration in accordance with aspects of the present disclosure.

FIG. 2 illustrates time course of treatment of mice with a viral vectors as illustrated in FIG. 1 for determining expression patterns of reporter proteins driven by BCE. At 5 days of age (P5), neonatal mice received dorsal sc AAV injection (of an AAV9 carrying one of the constructs shown in FIG. 1), at a dose of $1\times10^{10}$ genome copies per gram of body weight, in phosphate-buffered saline. At 42 days after birth (P42), bioluminescence was assessed to determine expression of marker proteins. Expression was determined by an in vivo imaging system (IVIS™, Perkin Elmer) as shown in FIGS. 3 (dorsal view) and 4 (ventral view), as well as by micro CT scanning to show topographical expression patterns, as shown in FIG. 5. AAV9.BCE.luci transduced subjects were first imaged for bioluminescence, and then scanned by micro CT, with AAV9.BCE.GFP serving as a control. In FIG. 5, bioluminescence signal origins were matched with tissues mapped by micro CT (pink=brown adipose tissue, blue or red=bioluminescence signal positive tissues). Expression was specifically elevated in BAT, demonstrating the BAT-specific expression driven by the BCE cis-regulatory element following transfection during the neonatal period.

Figure 6:
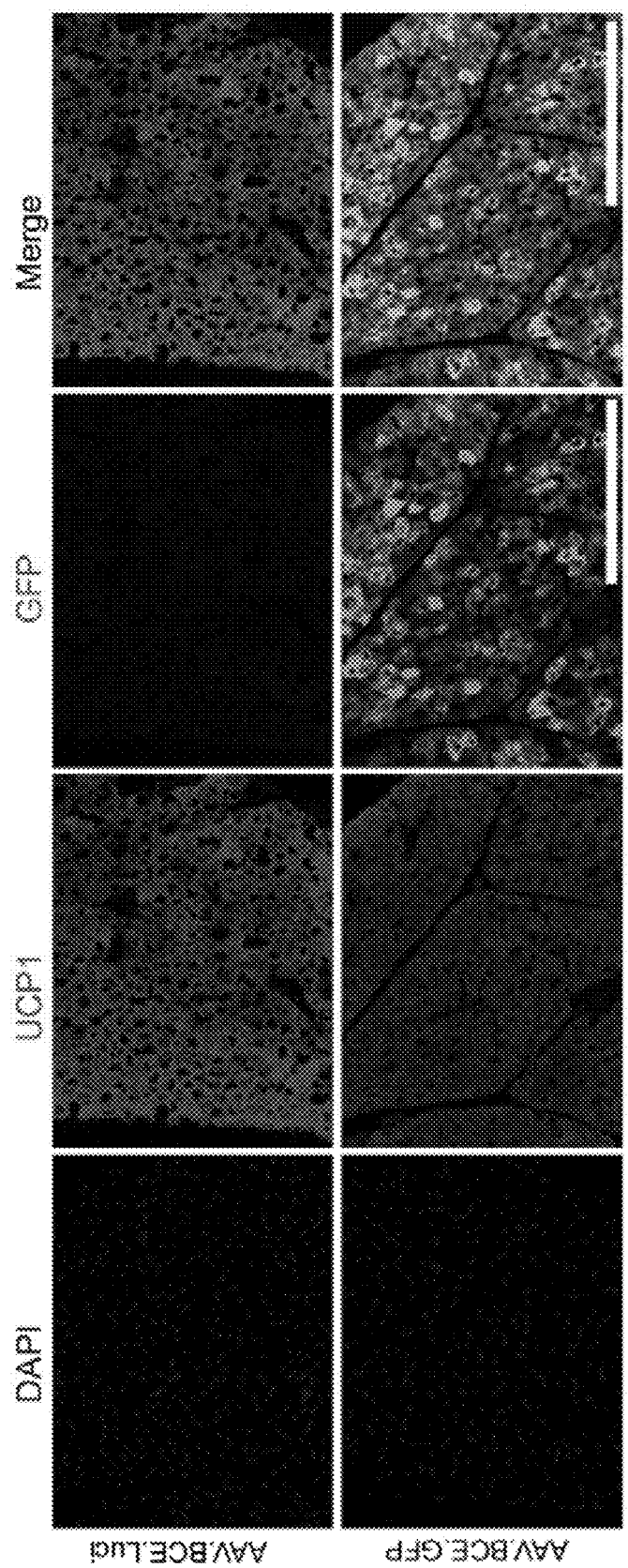
FIG. 6 shows immunofluorescence staining images of interscapular BAT following viral vector administration in accordance with aspects of the present disclosure.
Figure 7:
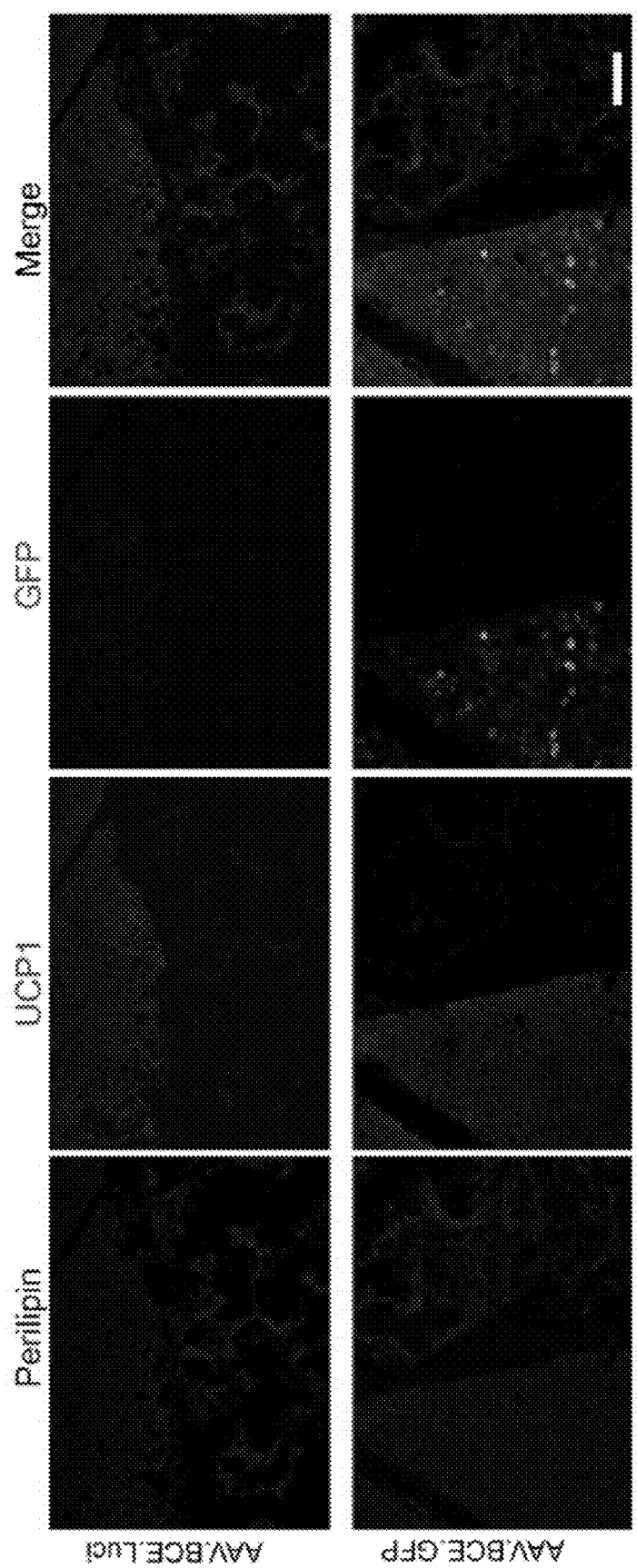
FIG. 7 shows immunofluorescence staining images of interscapular BAT and WAT following viral vector administration in accordance with aspects of the present disclosure.

As shown in FIGS. 6 and 7, interscapular adipose tissues (i.e., in the region where BAT is located) were collected at postnatal day 60 and used for immunofluorescence staining. FIG. 6 shows immunofluorescence staining images of interscapular BAT (using UCP1 imaging to identify BAT cells), and FIG. 7 shows immunofluorescence staining images of both BAT and white adipose tissue (using perilipin staining to mark adipose tissue, both BAT and WAT.). Nuclear stain DAPI is also shown in FIG. 6 and GFP expression was used to stain cells with BCE-driven reporter expression in animals treated with AAV.BCE.GFP (with AAV.BCE.Luci treatment serving as control). Bar=200 μm. BCE drove expression of reporter protein in adipocytes, and in BAT in particular.

Figure 8:
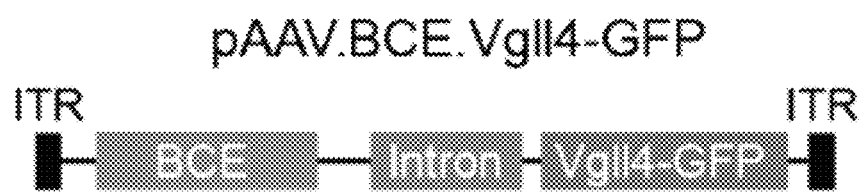
FIG. 8 shows a schematic view of a construct in accordance with aspects of the present disclosure.

FIG. 8 shows a schematic view of a pAAV.BCE.Vgll4-GFP construct administered via an AAV9 carrier. The construct resembles that shown in FIG. 1 except that Vgll4-GFP is the coding sequence whose expression is driven by BCE rather than merely GFP or luciferase. The sequence of the BCA-intron-Vgll4-GFP transcript is SEQ ID NO:39, and is a polynucleotide including a cis-regulatory element and a nucleotide sequence encoding a vestigial like 4 protein, wherein the cis-regulatory element includes an uncoupling protein 1 enhancer and an uncoupling protein 1 promoter. An intron is present between the cis-regulatory element and nucleotide sequence encoding a vestigial like 4 protein. The construct was packaged in an adeno-associated viral vector (AAV9) for transfection of cells of an organism with the construct.

Figure 9:
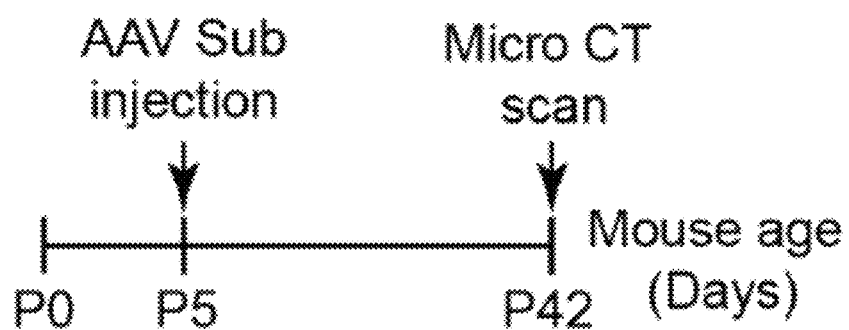
FIG. 9 shows timing of vector administration and BAT and WAT measurement in accordance with aspects of the present disclosure.
Figure 10:
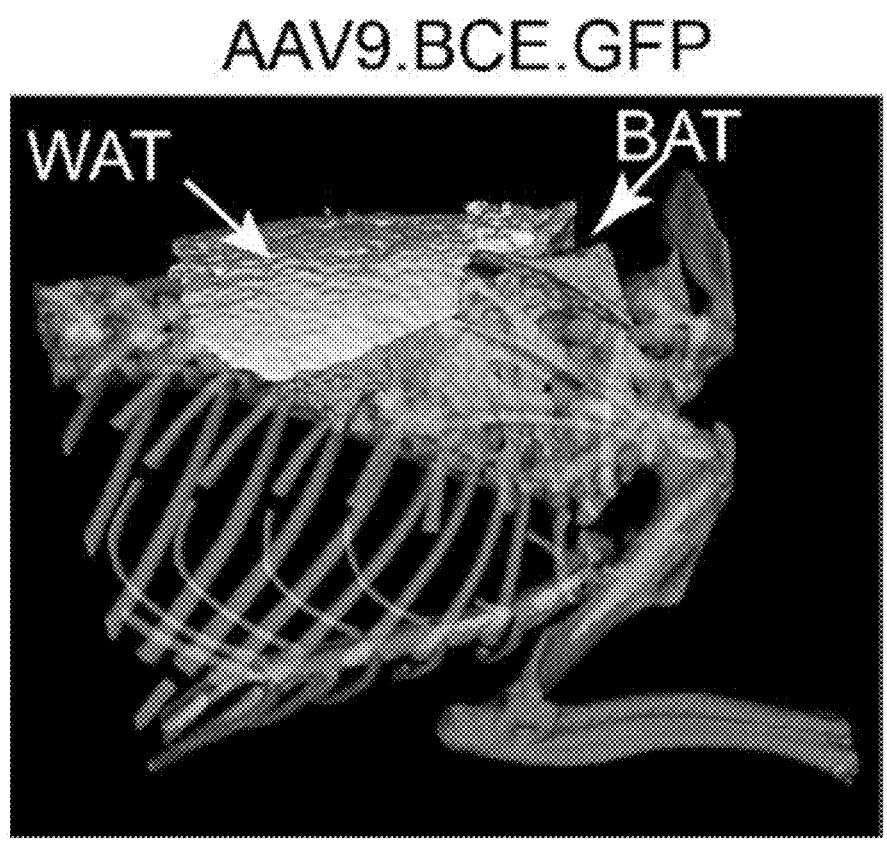
FIG. 10 shows relative BAT and WAT expression following treatment with control viral vector in accordance with aspects of the present disclosure.
Figure 11:
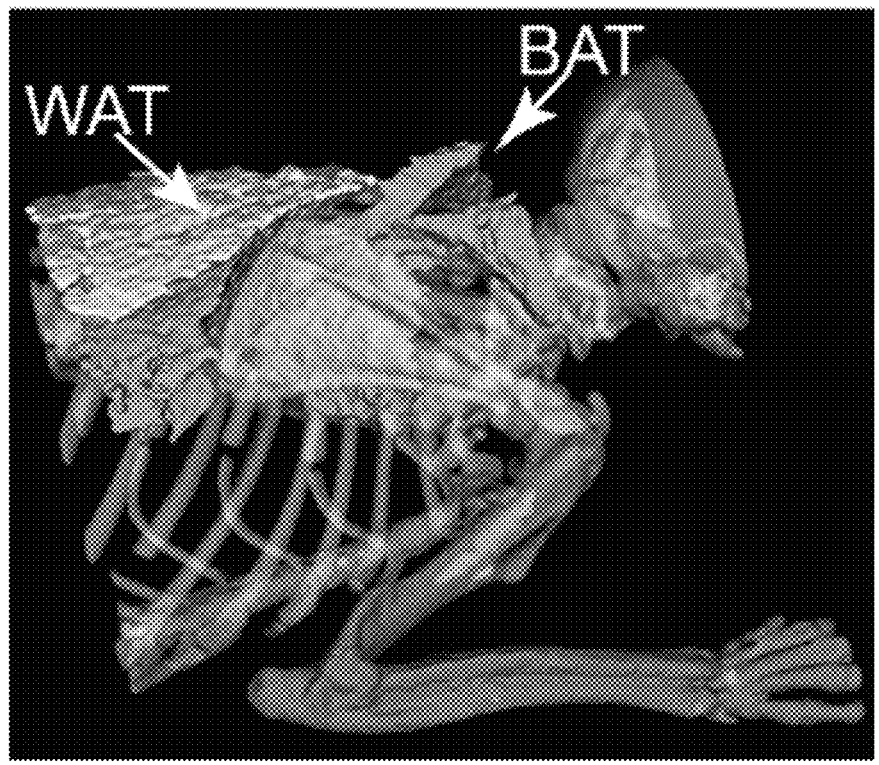
FIG. 11 shows relative BAT and WAT expression following treatment with a viral vector including a UCP-1 cis-regulatory element and Vgll4 coding sequence in accordance with aspects of the present disclosure.

FIG. 9 illustrates time course of treatment of mice with a viral vectors as illustrated in FIG. 8 for determining effects on adipose tissue volume. On postnatal day 5 mice were injected dorsally sc with AAV (AAV9.BCE.Vgll4-GFP, or AAV9.BCE.GFP, carrying the construct shown in FIG. 1, as a control), at a dose of $1\times10^{10}$ genome copies per gram of body weight, in phosphate-buffered saline. On postnatal day 42, a micro CT scan was taken to measure intrascapular adipose tissue volume, using standard commercially available micro CT scan software (analyze 12™). Intrascapular adipose tissue was differentiable from neighboring tissue, and BAT was differentiable from WAT, due to differences in Hounsfield units associated with differing tissue types according to standard micro CT scan techniques. An example scan is shown in FIGS. 10 (control) and 11 (for a subject injected with AAV9.BCE.Vgll4-GFP). BAT and WAT are as indicated. Increased volume of BAT and decreased volume of WAT can be seen following BCE-driven expression of Vgll4.

Figure 12:
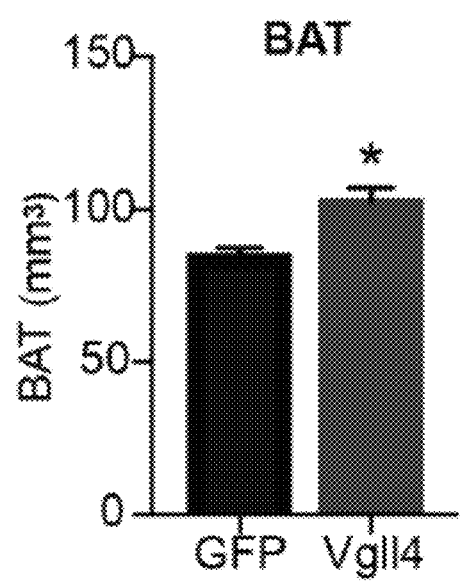
FIG. 12 shows an effect of treatment with a viral vector including a UCP-1 cis-regulatory element and Vgll4 coding sequence on BAT volume in accordance with aspects of the present disclosure.
Figure 13:
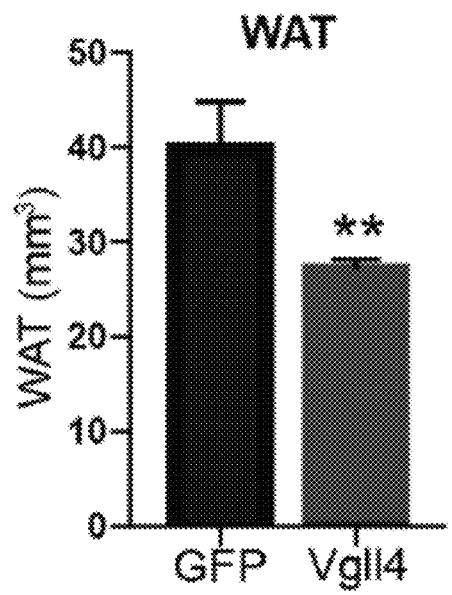
FIG. 13 shows an effect of treatment with a viral vector including a UCP-1 cis-regulatory element and Vgll4 coding sequence on WAT volume in accordance with aspects of the present disclosure.
Figure 14:
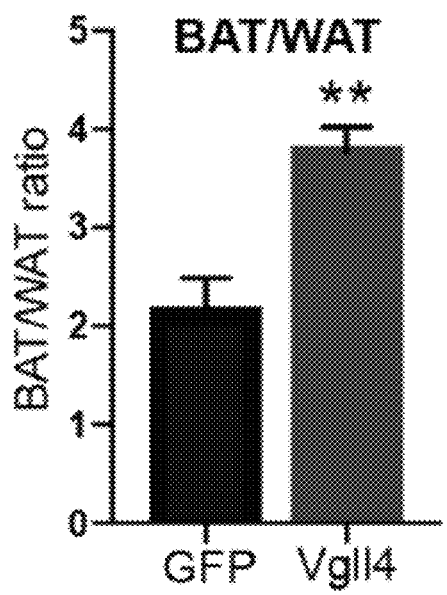
FIG. 14 shows an effect of treatment with a viral vector including a UCP-1 cis-regulatory element and Vgll4 coding sequence on the ratio of WAT volume to BAT volume in accordance with aspects of the present disclosure.
Figure 15:
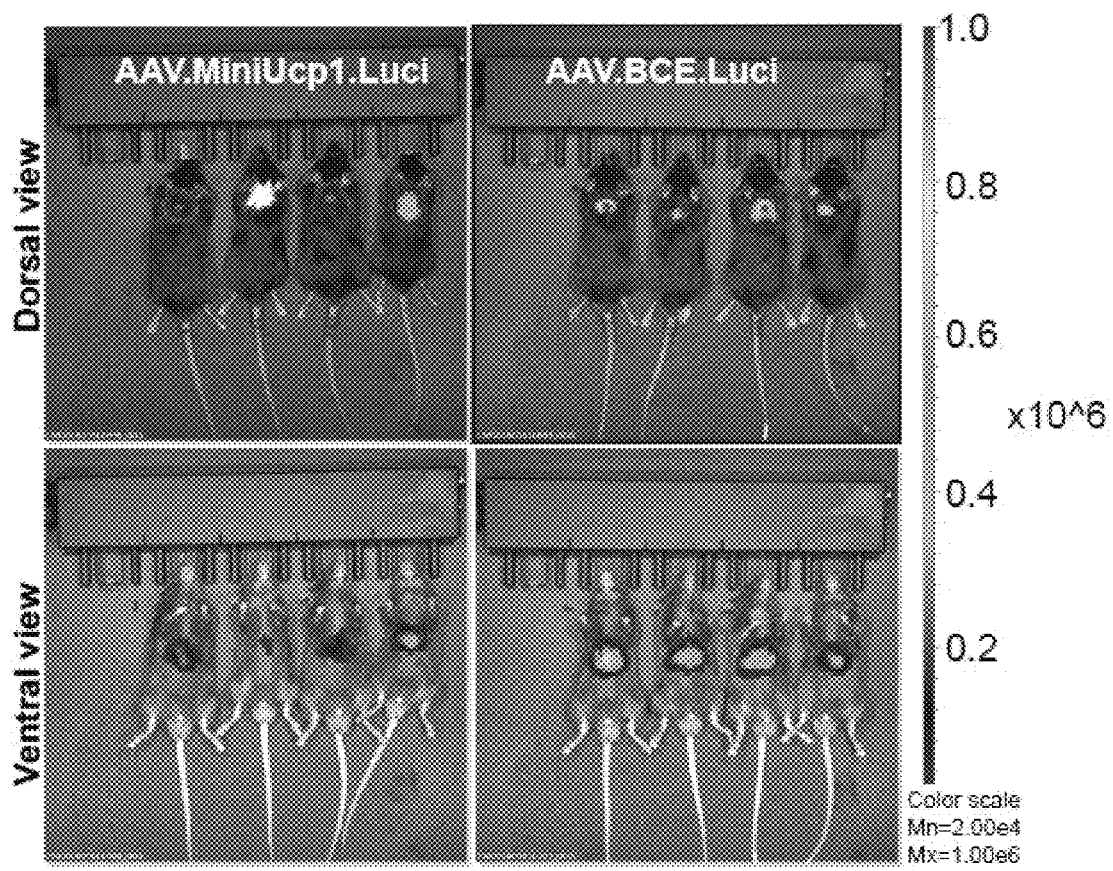
FIG. 15 shows bioluminescent expression of a reporter protein, luciferase, in 6-week old mice administered viral vectors including cis-regulatory elements in accordance with the present disclosure.
Figure 16:
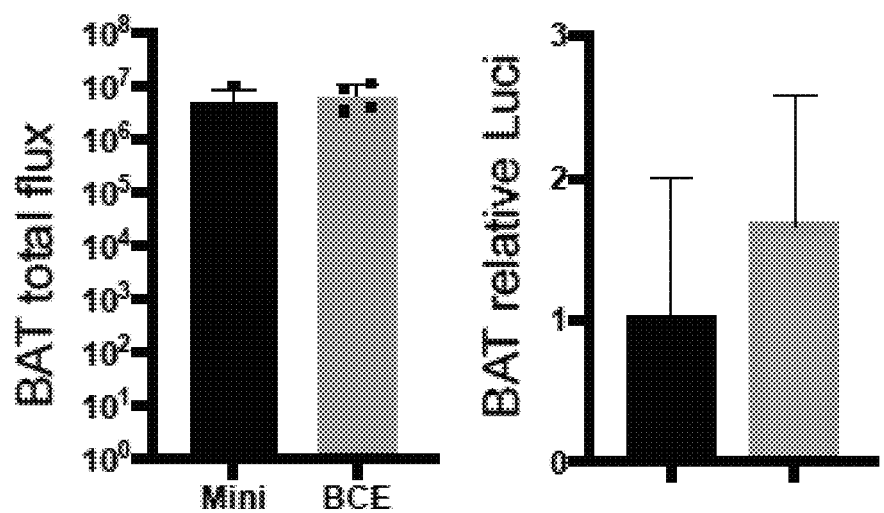
FIG. 16 shows quantification of luciferase activity in brown adipose tissue (BAT).
Figure 17:
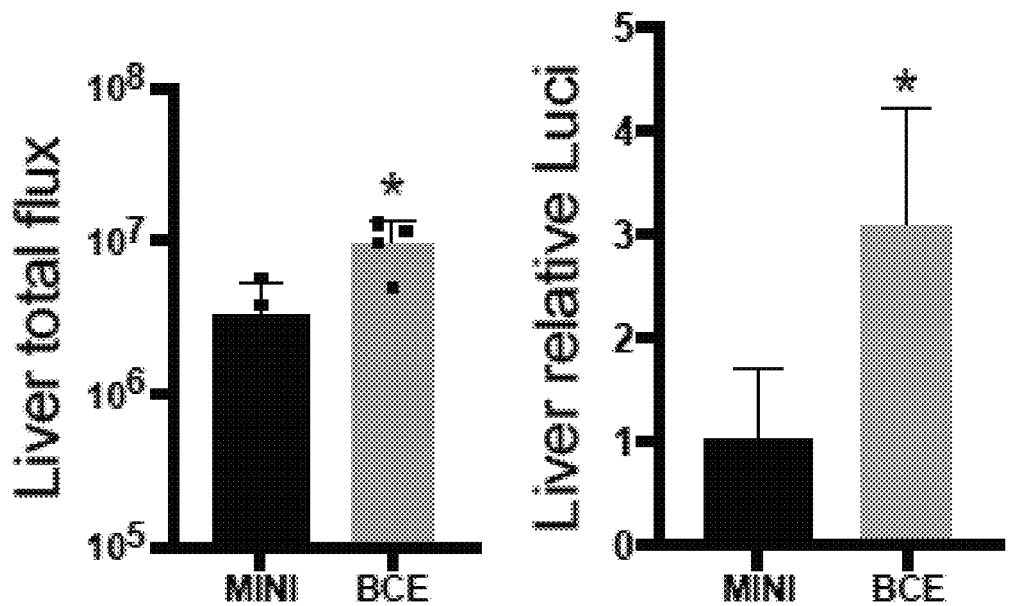
FIG. 17 shows quantification of luciferase activity in liver.

BAT volume was measured as graphically represented in FIG. 12. In subjects with BCE-driven Vgll4 expression, BAT volume was an average of 102.2±2.8 mm³, compared to 84.2±1.9 mm³ in controls (*=p<0.05). WAT volume was measured as graphically represented in FIG. 13. In subjects with BCE-driven Vgll4 expression, WAT volume was an average of 27.1±0.6 mm³, compared to 40.0±2.8 mm³ in controls (=p<0.01). Ratio of BAT/WAT volume was measured as graphically represented in FIG. 14. In subjects with BCE-driven Vgll4 expression, BAT/WAT volume ration was an average of 3.8±0.6 mm³, compared to 40.0±2.8 mm³ in controls (=p<0.01). Thus, transfection of cells of an organism with a construct including a cis-regulatory element driving expression of Vgll4, wherein the cis-regulatory element includes an uncoupling protein 1 enhancer and an uncoupling protein 1 promoter, increased BAT volume, decreased WAT volume, and increased a ration of BAT volume to WAT volume.

Figure 18:
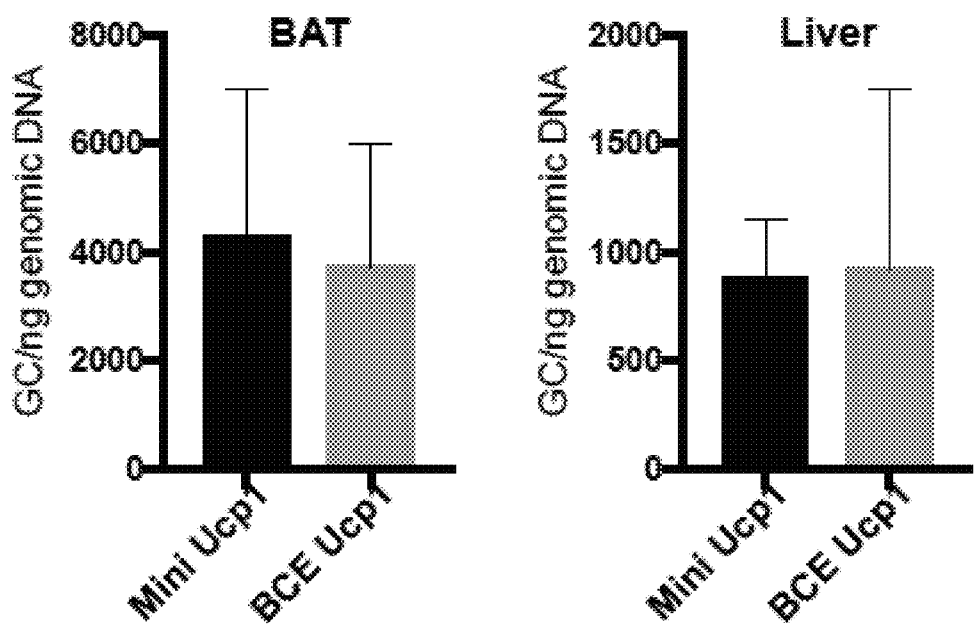
FIG. 18 shows quantification of viral vector genome copies in BAT and liver as assessed by real-time PCR.

Example 2: A Ucp1 Cis-Regulatory Element Drives Expression in BAT and Liver when Transfection Occurs During Adulthood An AAV vector (AAV9) containing a construct with a BCE cis regulatory element (SEQ ID NO: 3) driving expression of luciferase (AAV.BCE.Luci) was administered to to 6 weeks old mice. In other mice, the cis regulatory element (MiniUcp1) included a Ucp1 enhancer (SEQ ID NO: 4) but not a Ucp1 promoter (AAV.MiniUcp1.Luci). Subjects were tested for luciferase signals one week later. Results are illustrated in FIGS. 15-18. Both BAT (FIG. 16) and liver (FIG. 17) had luciferase signals, with BCE cis regulatory element driving higher liver expression that MiniUcp1. AAV.BCE.Luci drives expression in liver when transfection occurs later in development such as in adulthood. FIG. 18 shows that BAT and liver included viral vector genome copies, as assessed by real-time PCR.

AAV has very low chance of integrating into the host cell genome, existing primarily as episomes in host cells. If the host cells proliferate rapidly, daughter cells may easily lose AAV copy number. In cell cycle quiescent cells, in contrast, AAV coexist until cells die. During development, such as in neonates, hepatocytes are rapidly proliferating, whereas BAT are mostly cell cycle quiescent cells. Without being limited to any particular theory or mechanism of action, during the growth of AAV.BCE.Luci transduced pups, hepatocytes but not the brown adipocytes may have shed AAVs, which could explain why luciferase signals can only be detected in the BAT but not in the liver following transfection early in development (as in Example 1). In the AAV.BCE.Luci transduced adult mice of the present Example (Example 2), BAT and hepatocytes were not actively proliferating, and luciferase signals were detected in both tissues.

Example 3. The Hippo-YAP Pathway

The Hippo-YAP signaling pathway is well known for controlling organ growth. In mammals, the Hippo kinase cascade includes MST1/2, LATS1/2, and the scaffold protein Salvador (Say). Activation of these kinases results in phosphorylation and inactivation of YAP and WWTR1 (more commonly known as TAZ), orthologous transcriptional coactivators that are terminal effectors of this pathway.

Figures 19, 20:
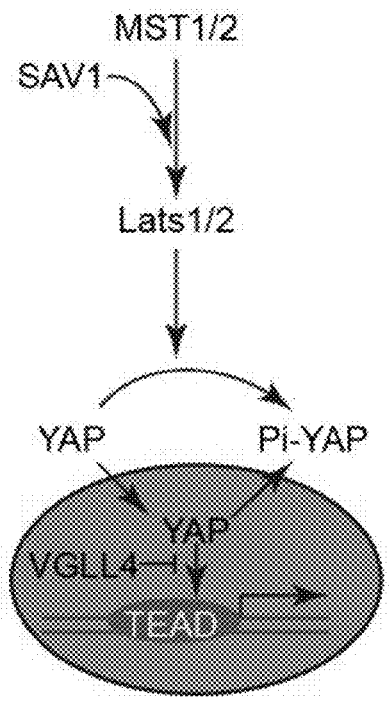
FIG. 19 is an illustration of the Hippo/YAP signaling cascade and Vgll4's inhibitory role in YAP/TEAD interactions.
FIG. 20 shows the mutations made to two TONDU (TDU_1 and TDU_2) domains of Vgll4 isoforms. Vgll4 isoforms A through F include two TDU domains, TDU_1 and TDU_2, with the indicated sequences (SEQ ID NO: 41 and SEQ ID NO: 42). The Vgll4-HF4A mutants of Vgll4 isoforms disclosed herein include two alanine substitutions to four amino acids, two in TDU_1 (a histidine to alanine and a phenylalanine to alanine) and two in TDU_2 (a histidine to alanine and a phenylalanine to alanine). Vgll4-HF4A have the dual-substituted TDU domains SEQ ID NO: 43 and SEQ NO ID: 44 (instead of SEQ ID NO: 41 and SEQ ID NO: 42, respectively).

YAP/TAZ interact with TEAD family transcription factors to regulate downstream target genes expression. Vestigial like 4 (VGLL4) is another co-transcriptional factor that serves as a suppressor of a YAP-TEAD complex. Mechanistically, VGLL4 directly binds to TEAD through its two TONDU (TDU) domains, and the binding of VGLL4 or YAP to TEAD is mutually exclusive (FIG. 19).

Figure 21:
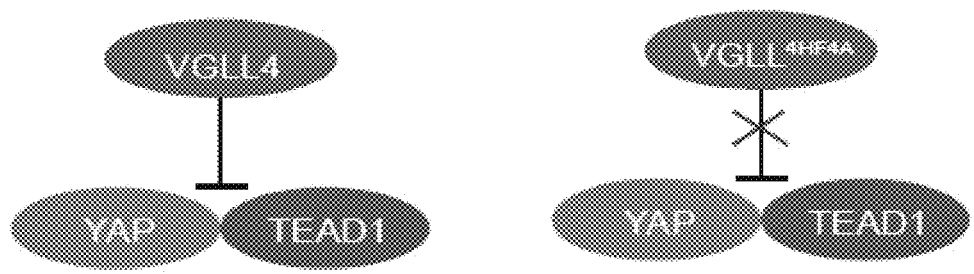
FIG. 21 is an illustration showing that whereas Vgll4 disrupts a YAP/TEAD1 complex, Vgll4-HF4A mutants do not.

Each VGLL4 TDU domain has two essential animal acid residuals (HF) mediating VGLL4-TEAD interaction (SEQ ID NO: 41 and SEQ ID NO: 42, respectively). Replacing the HFs in the TDU domains with four alanine residues (FIG. 20) minimizes the interaction between VGLL4 and TEAD. Unlike VGLL4, VGLL4-HF4A does not suppress a YAP-TEAD complex (FIG. 21). YAP/TAZ may promote BAT thermogenesis, raising the possibility of manipulating this pathway to reduce obesity.

Example 3. TEAD1 Directly Regulates the Expression of Fgf21

Figure 22:
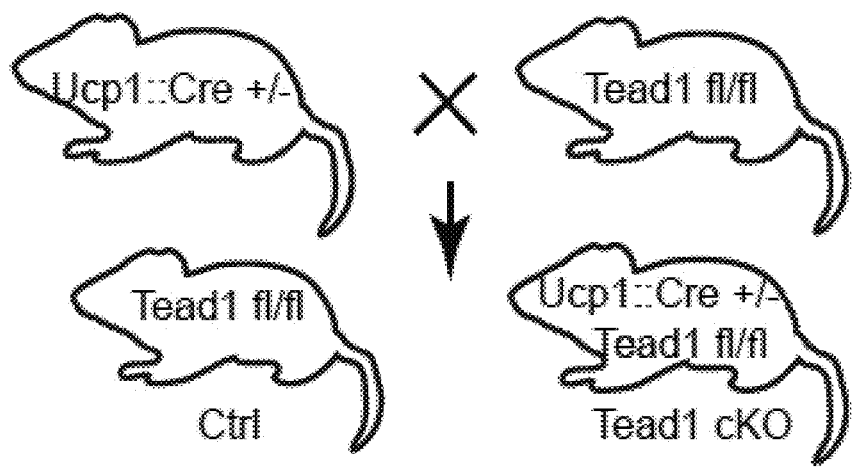
FIG. 22 Shows a schematic illustration of generation of brown adipocyte specific Tead1 knockout mice.
Figure 23:
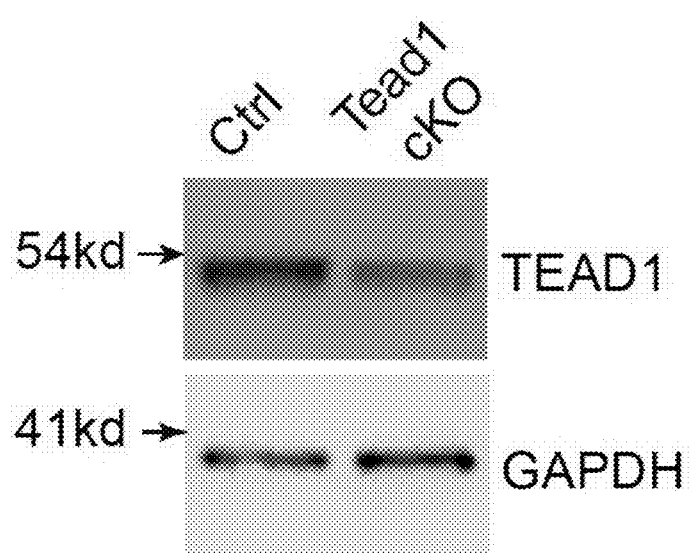
FIG. 23 is a western blot showing confirmation of depleted expression of TEAD1 in brown adipose tissue of the conditional TEAD1 knockout mice, with GADPH as a control.
Figure 24:
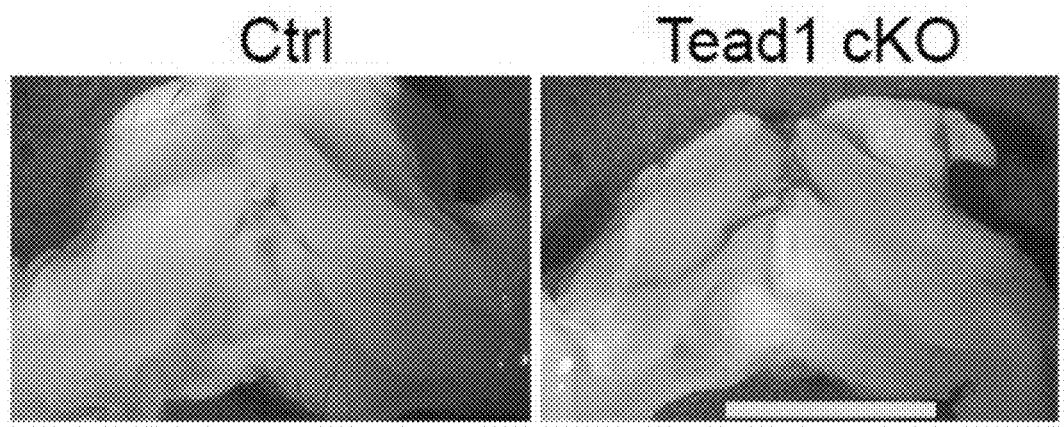
FIG. 24 shows whole mount view of interscapular brown adipose tissue (iBAT) collected from 1-month old male mice. Bar=5 mm.
Figure 25:
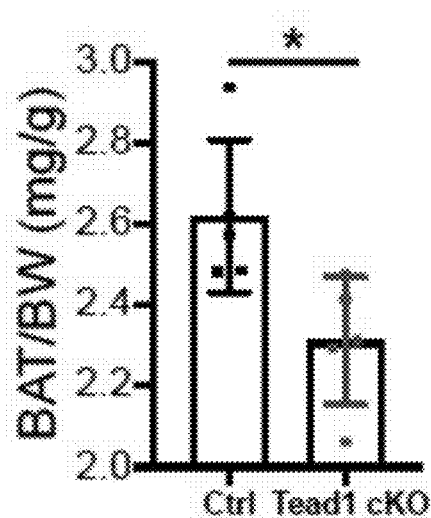
FIG. 25 shows the ration between iBAT and body weight ratio (*P<0.05).
Figure 26:
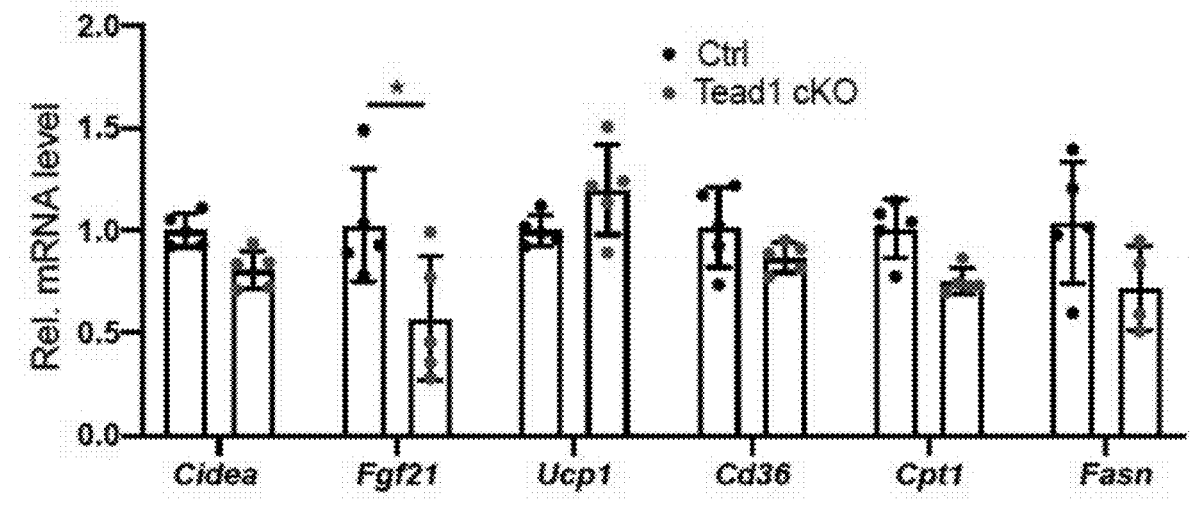
FIG. 26 shows qRT-PCR measurement of various mRNA transcript levels in BAT, normalized to 36B4.
Figure 27:
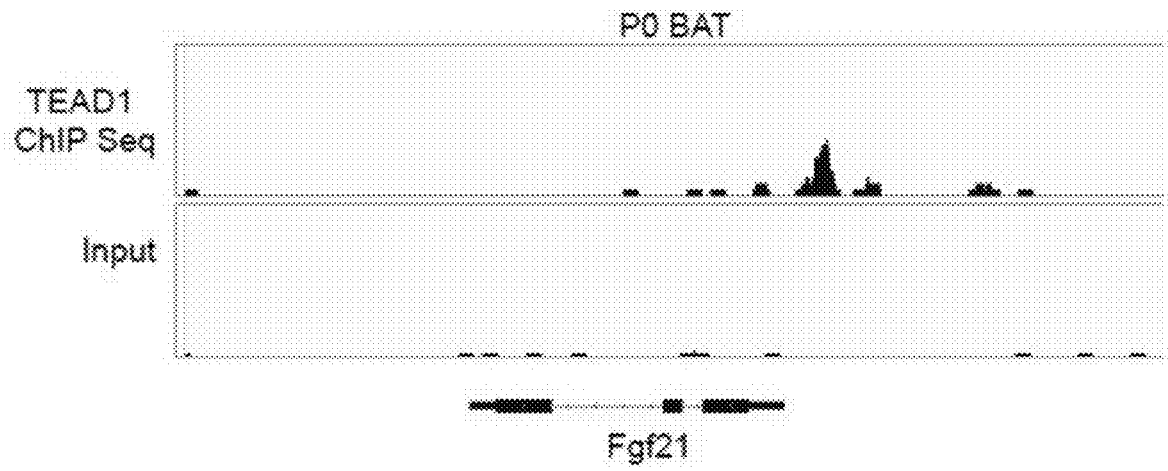
FIG. 27 is a genomic view of TEAD1 binding site in the Fgf21 promoter region.

Double heterozygous YAP and TAZ knockout mice have previously been shown to have much smaller BAT than their littermate controls at four weeks after birth. In the Hippo-YAP pathway, YAP/TAZ interacts with TEAD proteins to regulate downstream targets expression. Thus, TEAD1 may regulated the postnatal growth of BAT. As disclosed herein, Ucp1::Cre transgenic mice were crossed with Tead1 fox allele to specifically delete Tead1 in the BAT (FIG. 22). TEAD1 depletion in BAT of Tead1 cKO mice was confirmed by western blot (FIG. 23). Compared with controls, the Tead1 cKO mice had smaller interscapular BAT deposits (FIGS. 24 and 25). Knocking out TEAD1 in the brown adipocytes significantly decreased the expression of Fgf21 in BAT (FIG. 26). Chromatin immunoprecipitation sequencing data demonstrated that TEAD1 directly binds to the promoter region of Fgf21 (FIG. 27). Fibroblast growth factor 21 (FGF21) is an important myokine that regulates glucose-lipid metabolism.

Example 4. Activation of VGLL4 Reduces Adiposity

Figure 28:
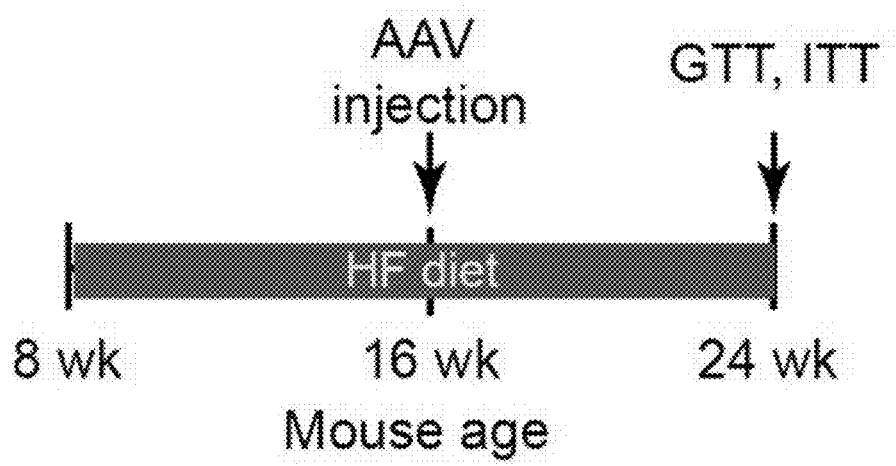
FIG. 28 is an illustration of experimental design for injecting adult mice fed a high-fat diet with a viral vector in accordance with the present disclosure. GTT is glucose tolerance test and ITT is insulin tolerance test.
Figure 29:
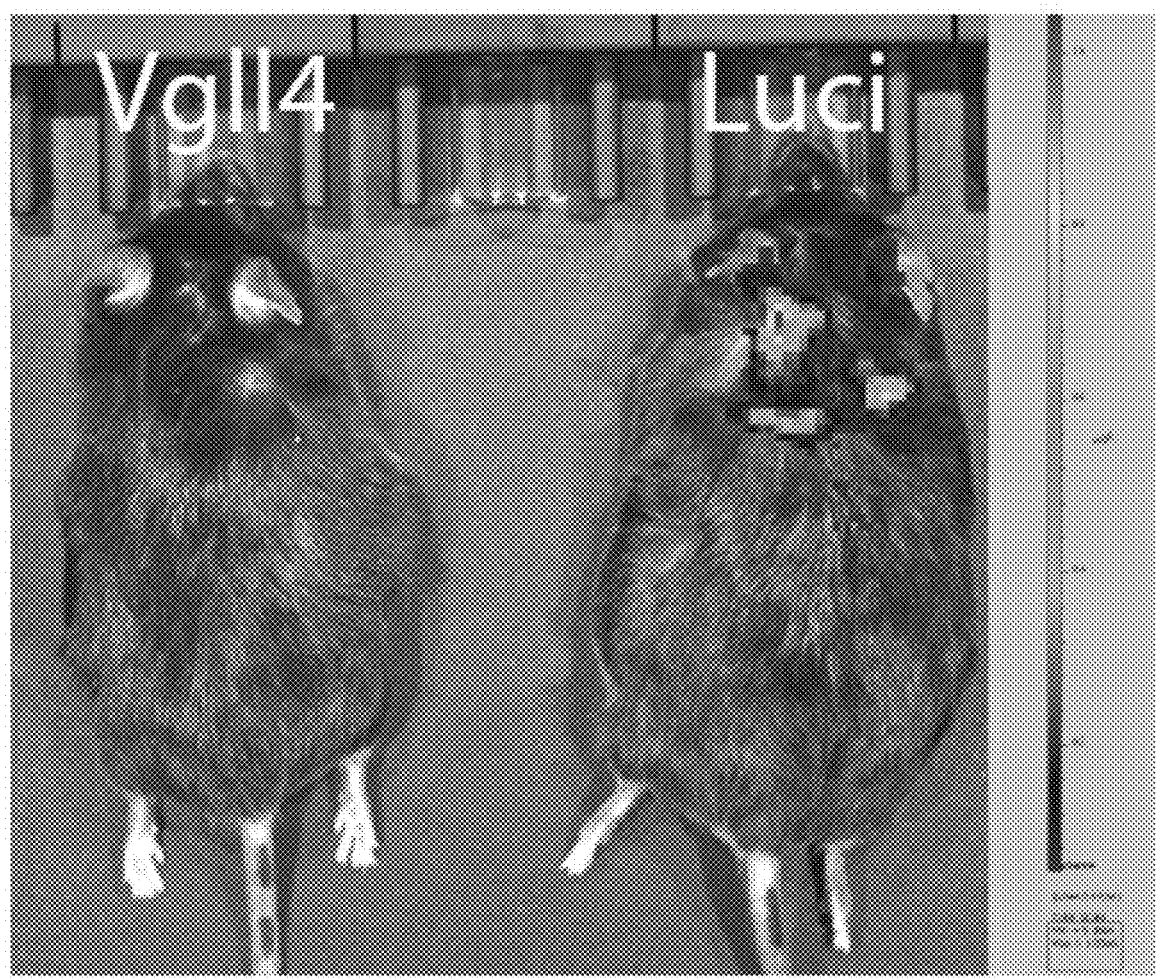
FIG. 29 shows bioluminescence imaging mice 8 weeks after infusion with viral vectors in accordance with the present disclosure.
Figure 30:
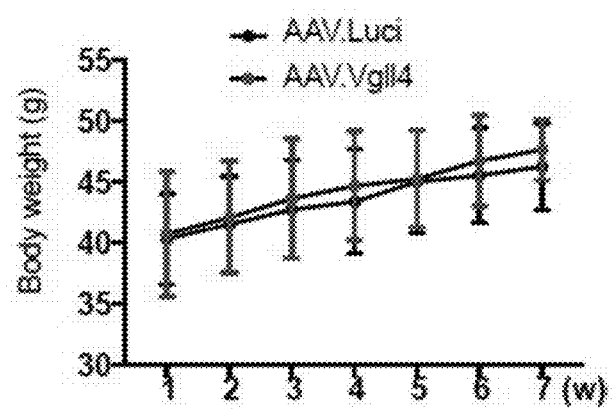
FIG. 30 and FIG. 31 show total body weight measurements and accumulated body weight gain measurements of transfected mice, respectively.
Figure 31:
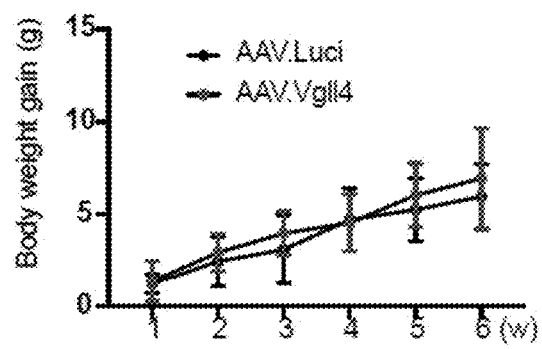
Figure 32A:
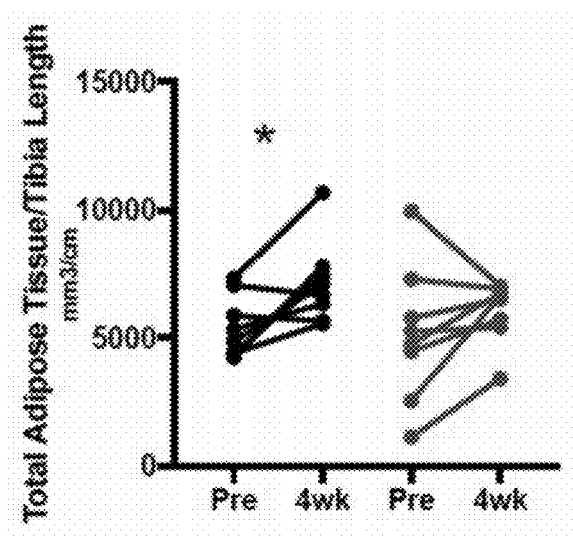
FIGS. 32A, 32B, AND 32C show effects for transfection with a viral vector carrying a BCE-Vggl4 polynucleotide transcript on a ratio of total adipose tissue to tibia length, a ratio of total lean mass to tibia length, and a ratio of fat mass to lean mass. In 32A and 32B, AAV.Luciferase control is on the right and AAV.Vgll4 is on the right.
Figure 32B:
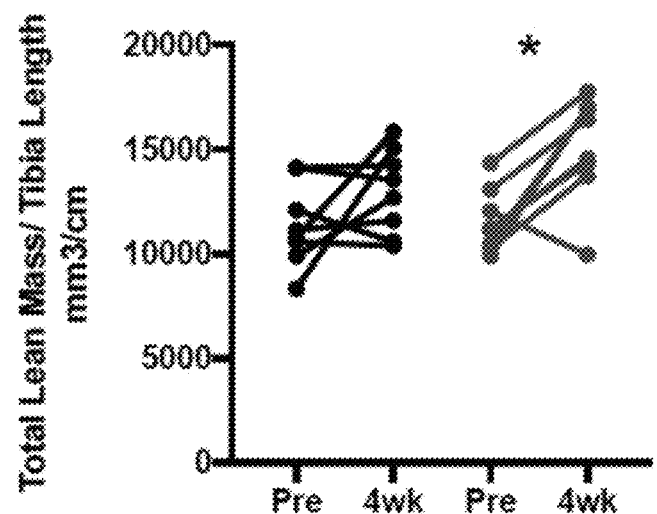
Figure 32C:
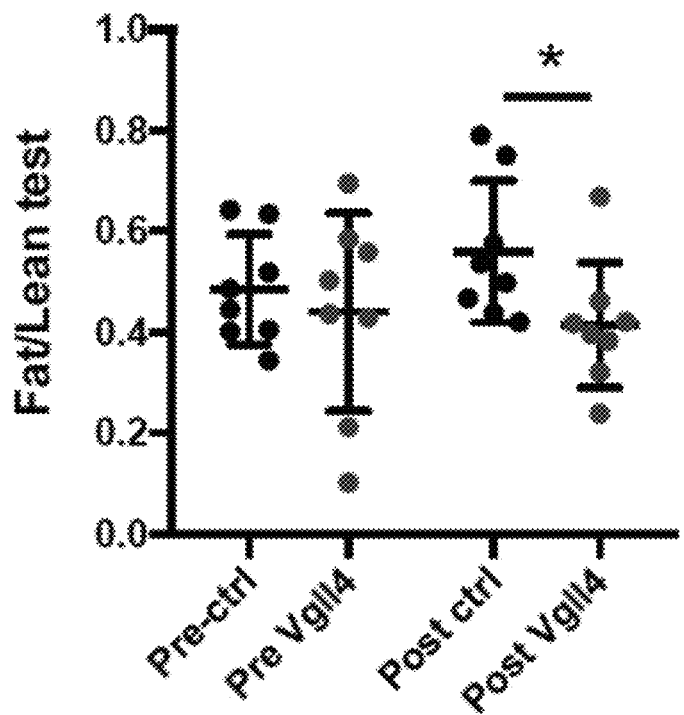

BAT plays important roles in non-shivering thermogenesis and energy homeostasis. As disclosed herein, AAV-mediated overexpression of VGLL4 increased BAT volume. To demonstrate whether activation of VGLL4 in an obesity model (mice fed on a high fat diet) would reduce body weight, AAV.BCE.VGLL4 (including SEQ ID NO: 39) into high fat diet induced obesity mice, and their body weight monitored for 7 weeks (FIG. 28). Controls received AAV with luciferase controlled by the cis regulatory element (SEQ ID NO: 3). 8 weeks after AAV delivery, luciferase signals were easily detected in the AAV.BCE.luci transduced mice (FIG. 29). Body weight and body weight gain values were not distinguishable between control and VGLL4 treated mice (FIGS. 30 and 31). However, using micro CT, the volume of adipose and non-adipose tissue (lean mass) were measured. 4 weeks after AAV transduction, although the body weight gain was similar between control and VGLL4 mice, the control but not the VGLL4 mice showed a significantly increase in adipose tissue mass. Meanwhile, VGLL4 but not the control mice had a significant increase of lean mass. Consequently, 4 weeks after AAV infusion, the VGLL4 mice had a lower fat/lean test ratio than the control mice (FIGS. 32A-C). Western blot showed that exogenous VGLL4 was expressed in BAT of AAV.BCE.VGLL4 transduced mice (not shown).

Example 5. AAV.BCE.VGLL4 Mitigates Body Weight Gain

Figure 33A:
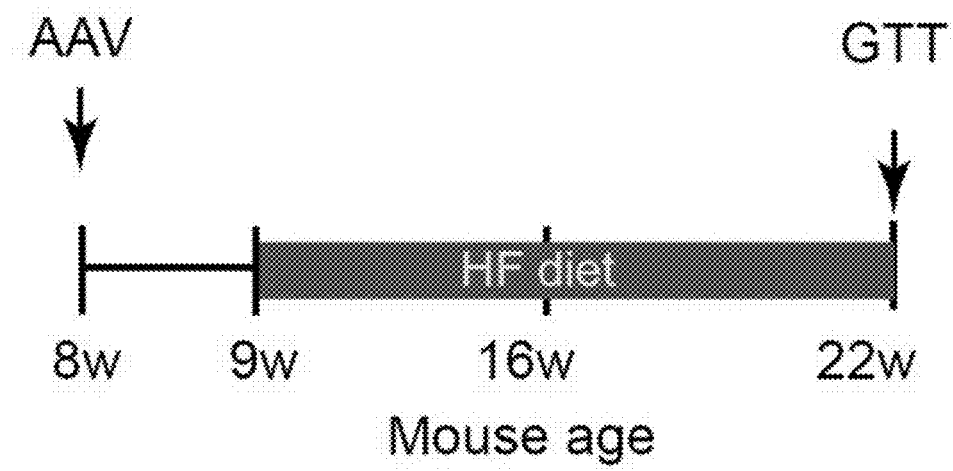
FIG. 33A shows an illustration of an experimental design demonstrating that pre-treatment of mice with AAV.BCE.VGLL4 mitigates body weight gain. AAV.BCE.Vgll4 was subcutaneously injected into the interscapular region of 8-weeks-old C57/BL6 mice. After 13 weeks high fat diet treatment, mice were tested for glucose tolerance (GTT). AAV.BCE.GFP was used as control.
Figure 33D:
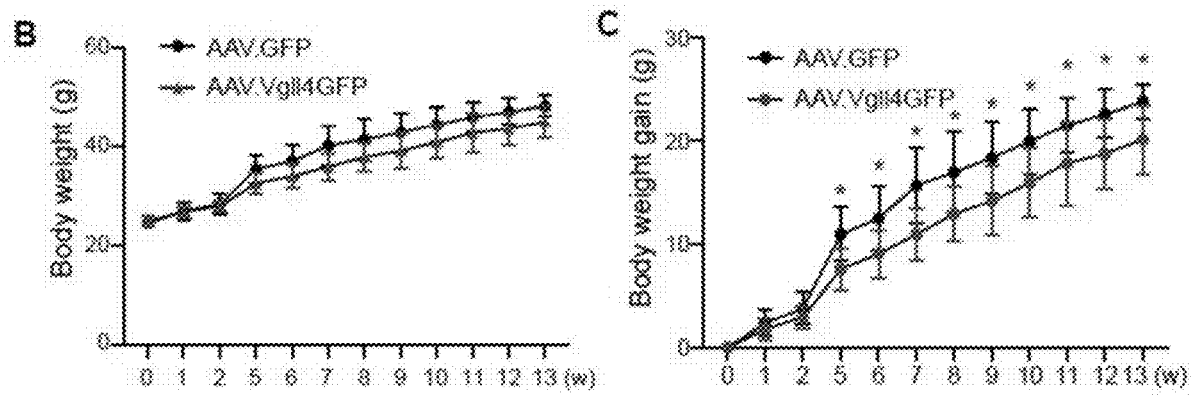
FIG. 33D shows fgf21 mRNA levels in BAT following transfection with a construct driving Vgll4 with a Ucp1 cis regulatory element in accordance with aspects of the present disclosure.
Figure 33D:
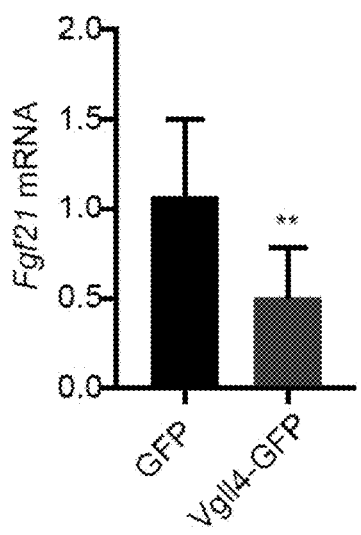

To demonstrate whether activation of VGLL4 in normal mice would prevent or mitigate the progression of obesity, AAV.BCE.VGLL4 (including SEQ ID NO: 39) was administered to 8-week-old mice. Beginning 1 week after injection, mice were fed a high-fat diet (FIG. 33A). At the end of 13 weeks high fat diet treatment, the body weight of VGLL4 mice was lower than the control mice, though the difference did not reach statistical significance (FIG. 33B). Starting from week 5, however, VGLL4 mice had a significantly lower accumulated body weight gain than controls (FIG. 33C). As disclosed herein (Example 2), AAV.BCE.VGLL4 targets both BAT and liver when administered later in development such as in adulthood. Fgf21 is a target of TEAD1 (FIGS. 26 and 27), and is mainly produced by liver and adipose tissue. Expression of VGLL4 and Fgf21 was therefore measure in liver. VGLL4 was overexpressed in liver, and that Fgf21 was significantly decreased in liver of VGLL4 mice (FIG. 33D).

Example 6. AAV.BCE.VGLL4HF4A Increases BAT Mitochondrial Genes Expression

As disclosed herein, VGLL4 expression driven by a Ucp1 cis regulatory element mitigated body weight gain, it also suppressed the expression of Fgf21, which is important for glucose metabolism. VGLL4 may therefore have multiple roles, interacting with TEAD1 to decrease Fgf21 expression, while also interacting with other unknown factors to improve energy expenditure. Without being limited to any particular theory or mechanism of action, this possibility may indicate why VGLL4 may mitigate body weight gain without improving glucose metabolism. An AAV.BCE.VGLL4HF4A vector was created, which expresses a mutated VGLL4 that does not interact with TEAD (HF4A mutations), including SEQ ID NO: 36, and also including a GFP reporter protein (SEQ ID NO: 40). 8-week-old normal mice received subcutaneous injection of AAV.BCE.VGLL4HF4A, resulting in transfection of BAT (FIGS. 34A and B). qRT-PCR results showed that overexpression of VGLL4HF4A did not affect the expression of Fgf21 but reduced the expression of Cidea and Fasn (FIG. 34C), which are two genes involved in lipogenesis, in BAT. Additionally, VGLL4HF4A increased the expression of Cox2 (Cytochrome C Oxidase Subunit II, encoded by MT-CO2) and Cox6a2 (Cytochrome C Oxidase Subunit 6A2) in BAT (FIG. 34D). These data indicate that VGLL4HF4A may increase mitochondrial respiration activity without affecting Fgf21 expression, and also reduce lipogenesis.

Figure 35A:
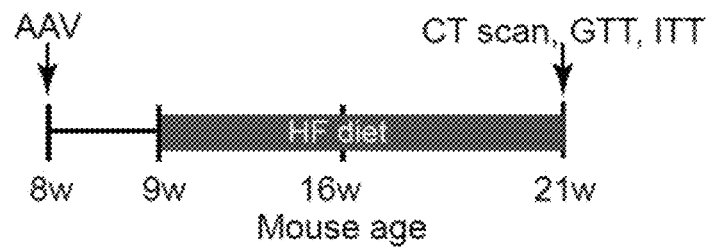
FIG. 35A shows an illustration of an experimental design demonstrating that pre-treatment with an AAV.BCE.VGLL4-HF4A mitigates body weight gain. AAV.BCE.Vgll4HF4A was subcutaneously injected into the interscapular region of 8-weeks-old C57/BL6 mice. After 12 weeks high fat diet treatment, mice were tested for glucose (GTT) and insulin tolerance (ITT). AAV.BCE.GFP was used as control.
Figure 35B:
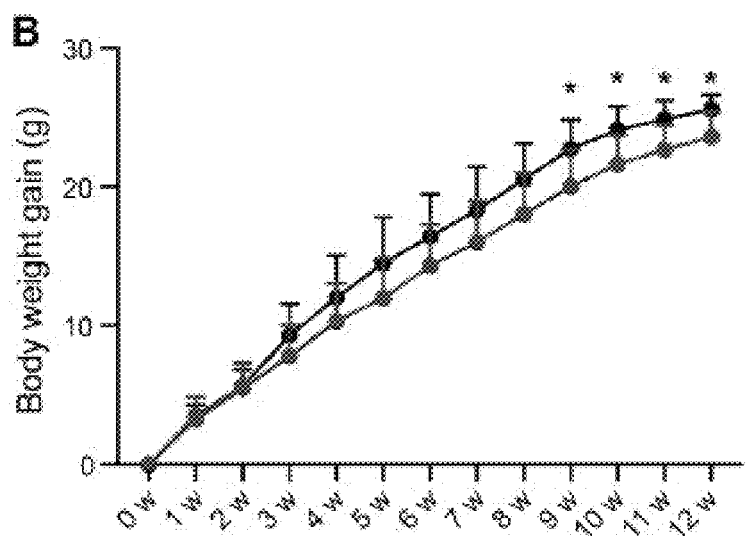
Figure 35C:
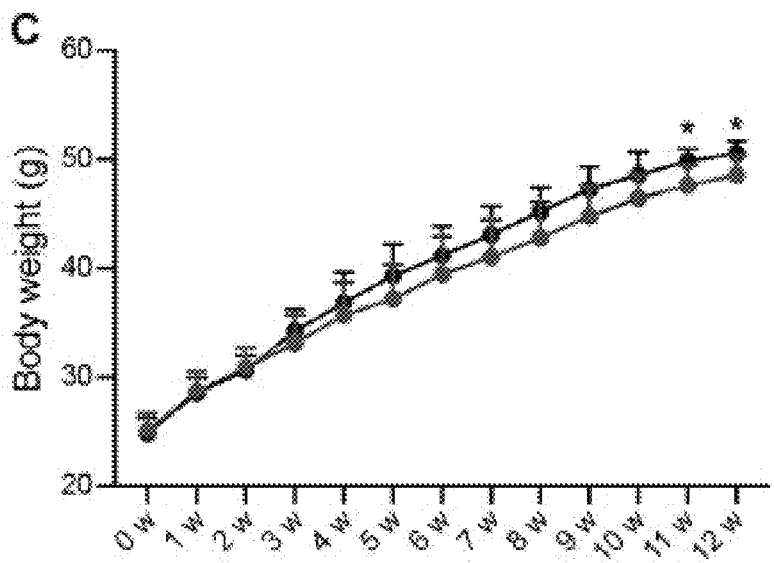
Figure 35D:
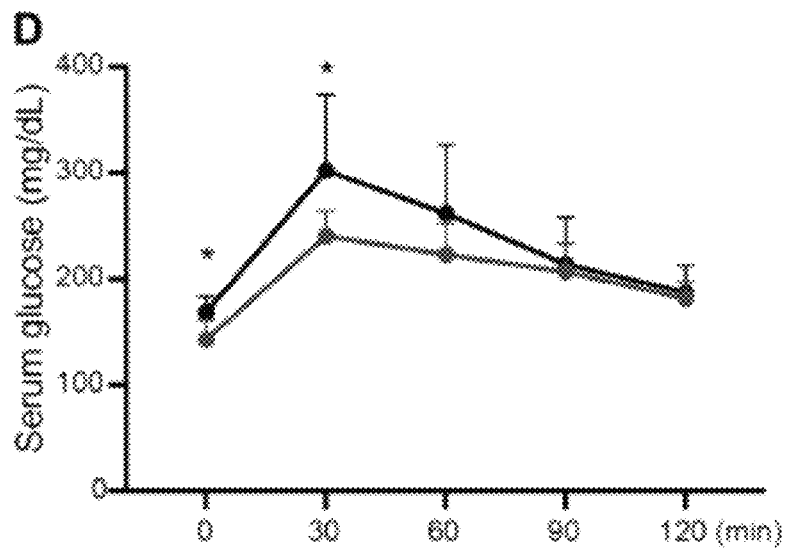
FIG. 35D shows serum glucose levels following glucose challenge in a glucose tolerance test. Upper traces are control and lower traces are AAV.BCE.Vgll-4HF4A.

Example 7. AAV.BCE.VGLL4HF4A Mitigates Body Weight Gain and Reduces Serum Glucose Level AAV.BCE.VGLL4HF4A (including SEQ ID NO: 36) was injected sc to the inter-scapular region of 8 week old C57/BL6 mice, at a dosage of $2\times10^9$ GC/gram body weight. AAV.BCE.GFP was used as control. One week after virus injection, 12 weeks of feeding with high fat diet (HFD) began (FIG. 35A). During HFD treatment, body weight gain rate of AAV.BCE.VGLL4HF4A mice (VGLL4HF4A) was slower than that of the AAV.BCE.GFP mice, and the difference reached to significance at 9 weeks after HFD treatment (FIG. 35B). 11 weeks after high fat diet treatment, the body weight of AAV.BCE.VGLL4HF4A mice started to become significantly lower than that of the AAV.BCE.GFP mice (FIG. 35C). A glucose tolerance test (GTT) showed that the starving serum glucose level and glucose peak level following glucose challenge was significantly lower in the AAV.BCE.VGLL4HF4A mice (FIG. 35D).

Example 8. AAV.BCE.VGLL4HF4A Reduces BAT Weight

Figures 36, 36A, 36C:
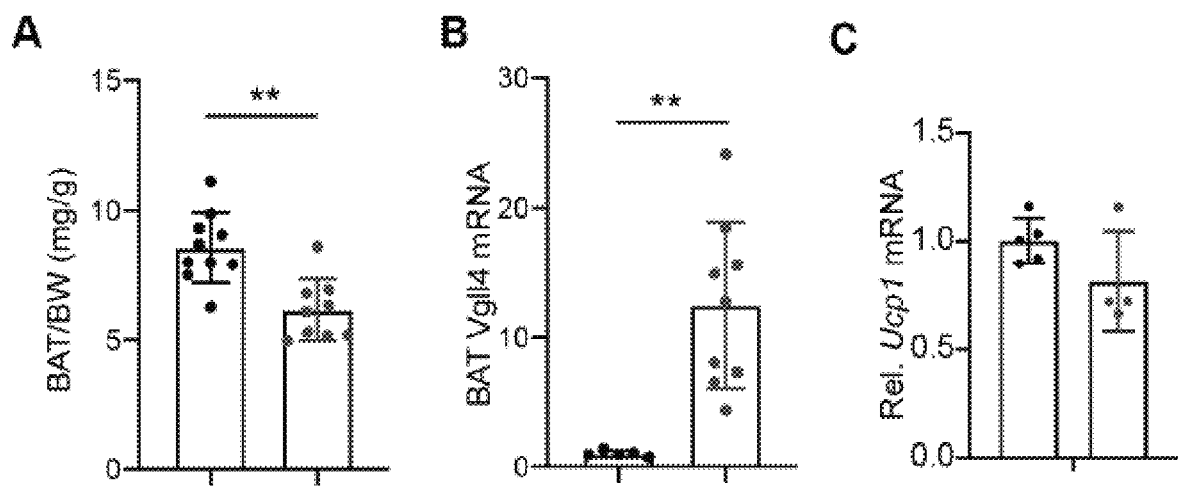

Compared to that of the GFP control mice, the mass of BAT was significantly lower in the VGLL4HF4A mice (FIG. 36A). qRT-PCR confirmed that VGLL4 was overexpressed in the BAT of VGLL4HF4A mice (FIG. 36B). The expression of Ucp1 was not affected by VGLL4HF4A (FIG. 36C). Expression levels of three more genes that regulate mitochondria respiration activity were also measured in BAT: Cox2, Cox6a, Ndufsa8. Cox2 was significantly upregulated in the VGLL4HF4A BAT (FIG. 36D). VGLL4HF4A also suppressed expression of Acc1, a gene involved in fatty acid synthesis (FIG. 36E). VGLL4HF4A may therefore preserve BAT function by both increasing the mitochondria respiration activity and attenuating fatty acid synthesis.

Example 9. AAV.BCE.VGLL4HF4A Reduces Liver Weight and Fatty Acid Synthesis

Figure 37D:
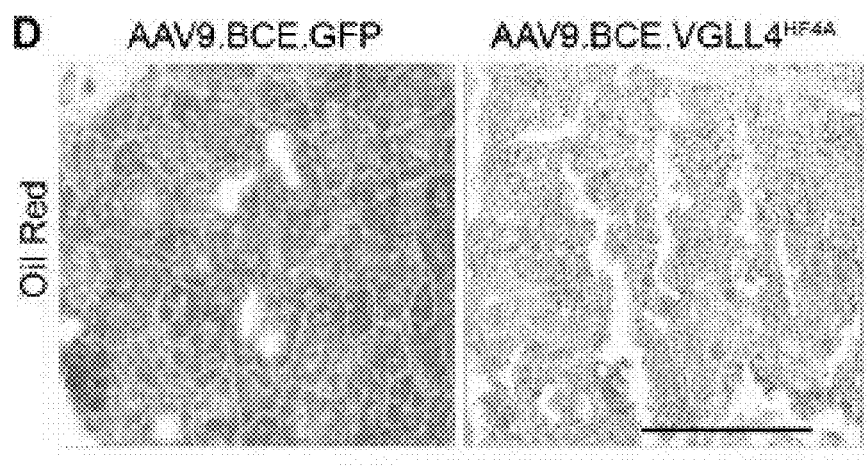
Figure 37E:
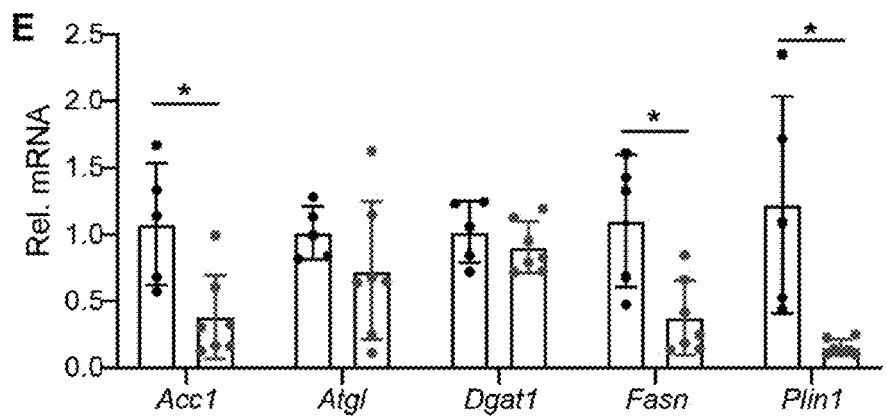
FIG. 37E shows mRNA levels of expression of fatty acid synthesis genes in liver by quantitative real-time PCR. A, B, E, Student t test, *, P<0.05; **, P<0.01. Control (AAV.BCE.GFP) is on the right and AAV.BCE.Vgll-4HFA is on the right.

A BCE cis regulatory element including a Ucp1 enhancer and Ucp1 promoter as disclosed herein drives gene expression in liver when adult subjects are transfected, as disclosed herein. Interestingly, liver weight of VGLL4HF4A mice was significantly lower than that of the GFP control mice (FIG. 37A). qRT-PCR confirmed that VGLL4 was robustly overexpressed in liver of VGLL4HF4A mice (FIG. 37B). Histology determined by haematoxylin and eosin (H&E) staining showed moderate lipid droplets accumulation and microsteatosis (FIG. 37C). Oil red staining confirmed that VGLL4HF4A liver had much less lipid droplets accumulation than the GFP control liver (FIG. 37D). The expression of fatty acid synthesis genes Acc1 and Fasn in liver were significantly reduced by VGLL4HF4A (FIG. 37E). VGLL4HF4A may prevent HFD induced liver pathologies such as liver metabolic dysfunction, inflammation, or non-alcoholic fatty liver disease It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein and may be used to achieve the benefits and advantages described herein.

Although examples have been depicted and described in detail herein, it will be apparent to those skilled in the relevant art that various modifications, additions, substitutions, and the like can be made without departing from the spirit of the present disclosure and these are therefore considered to be within the scope of the present disclosure as defined in the claims that follow.

What is claimed is:

1. A polynucleotide, comprising
a cis-regulatory element and a nucleotide sequence encoding a vestigial like 4 protein, wherein
the cis-regulatory element comprises an uncoupling protein 1 enhancer and an uncoupling protein 1 promoter, and
the vestigial like 4 protein comprises a first TDU domain having a first amino acid sequence and a second TDU domain having a second amino acid sequence, wherein
the first amino acid sequence comprises the amino acid sequence as set forth in SEQ ID NO: 41 with two amino acid substitutions, wherein the seventh amino acid of the amino acid sequence as set forth in SEQ ID NO: 41 is not H and the eighth amino acid of the amino acid sequence as set forth in SEQ ID NO: 41 is not F, and
the second amino acid sequence comprises the amino acid sequence as set forth in SEQ ID NO: 42, wherein the seventh amino acid of the amino acid sequence as set forth in SEQ ID NO: 42 is not H and the eighth amino acid of the amino acid sequence as set forth in SEQ ID NO: 42 is not F.

2. The polynucleotide of claim 1, wherein the uncoupling protein 1 enhancer has at least 90% identity with a sequence selected from the group consisting of the sequence as set forth in SEQ ID NO: 1 SEQ ID NO 4, and SEQ ID NO: 7.

3. The polynucleotide of claim 1, wherein the uncoupling protein 1 promotor has at least 90% identity with a sequence selected from the group consisting of the sequence as set forth in SEQ ID NO: 2, SEQ ID NO 5, and SEQ ID NO: 8.

4. The polynucleotide of claim 1, wherein the cis-regulatory element has at least 90% homology with a sequence selected from the group consisting of the sequence as set forth in SEQ ID NO: 3, SEQ ID NO: 6, and SEQ ID NO: 9.

5. The polynucleotide of claim 1, wherein the vestigial like 4 protein has at least 90% homology with a sequence selected from the group consisting of the sequence as set forth in SEQ ID NO: 21, SEQ ID NO: 23, SEQ ID NO: 25, SEQ ID NO: 27, SEQ ID NO: 29, SEQ ID NO: 31, and SEQ ID NO: 33.

6. The polynucleotide of claim 1, wherein the sequence encoding a vestigial like 4 protein has at least 90% identity with a sequence selected from the group consisting of the sequence as set forth in SEQ ID NO: 22, SEQ ID NO: 24, SEQ ID NO: 26, SEQ ID NO: 28, SEQ ID NO: 30, and SEQ ID NO: 32.

7. The polynucleotide of claim 1, wherein the vestigial like 4 protein has from 0 to 3 substitutions to a sequence selected from the group consisting of the sequence as set forth in SEQ ID NO: 23, SEQ ID NO: 25, SEQ ID NO: 27, SEQ ID NO: 29, SEQ ID NO: 31, and SEQ ID NO: 33, wherein the substitutions are not in the first TDU domain or the second TDU domain.

8. The polynucleotide of claim 1, further comprising an intron between the cis-regulatory element and the nucleotide sequence encoding a vestigial like 4 protein.

9. The polynucleotide of claim 8, wherein the intron has at least 90% homology with the sequence as set forth in SEQ ID NO: 34.

10. A viral vector, comprising
a polynucleotide, wherein the polynucleotide comprises a cis-regulatory element and a nucleotide sequence encoding a vestigial like 4 protein, wherein
the cis-regulatory element comprises an uncoupling protein 1 enhancer and an uncoupling protein 1 promoter, and
the vestigial like 4 protein comprises a first TDU domain having a first amino acid sequence and a second TDU domain having a second amino acid sequence, wherein
the first amino acid sequence comprises the amino acid sequence as set forth in SEQ ID NO: 41 with two amino acid substitutions, wherein the seventh amino acid of the amino acid sequence as set forth in SEQ ID NO: 41 is not H and the eight amino acid of the amino acid sequence as set forth in SEQ ID NO: 41 is not F, and the second amino acid sequence comprises the amino acid sequence as set forth in SEQ ID NO: 42 with two amino acid substitutions, wherein the seventh amino acid of the amino acid sequence as set forth in SEQ ID NO: 42 is not H and the eighth amino acid of the amino acid sequence as set forth in SEQ ID NO: 42 is not F.

11. The viral vector of claim 10, wherein the uncoupling protein 1 enhancer has at least 90% identity with a sequence selected from the group consisting of the sequence as set forth in SEQ ID NO: 1, SEQ ID NO 4, and SEQ ID NO: 7.

12. The viral vector of claim 10, wherein the uncoupling protein 1 promotor has at least 90% identity with a sequence selected from the group consisting of the sequence as set forth in SEQ ID NO: 2, SEQ ID NO 5, and SEQ ID NO: 8.

13. The viral vector of claim 10, wherein the cis-regulatory element has at least 90% homology with a sequence selected from the group consisting of the sequence as set forth in SEQ ID NO: 3, SEQ ID NO: 6, and SEQ ID NO: 9.

14. The viral vector of claim 10, wherein the vestigial like 4 protein has at least 90% homology with a sequence selected from the group consisting of the sequence as set forth in SEQ ID NO: 23, SEQ ID NO: 25, SEQ ID NO: 27, SEQ ID NO: 29, SEQ ID NO: 31, and SEQ ID NO: 33.

15. The viral vector of claim 4, wherein the sequence encoding a vestigial like 4 protein has at least 90% identity with a sequence selected from the group consisting of the sequence as set forth in SEQ ID NO: 22, SEQ ID NO: 24, SEQ ID NO: 26, SEQ ID NO: 28, SEQ ID NO: 30, and SEQ ID NO: 32.

16. The viral vector of claim 10, wherein the vestigial like 4 protein has from 0 to 3 substitutions to a sequence selected from the group consisting of the sequence as set forth in SEQ ID NO: 23, SEQ ID NO: 25, SEQ ID NO: 27, SEQ ID NO: 29, SEQ ID NO: 31, and SEQ ID NO: 33, wherein the substitutions are not in the first TDU domain or the second TDU domain.

17. The viral vector of claim 10, further comprising an intron between the cis-regulatory element and the nucleotide sequence encoding a vestigial like 4 protein.

18. The viral vector of claim 10, comprising an adeno-associated viral vector.

19. The polynucleotide of claim 1, wherein the vestigial like 4 protein has a sequence selected from the group consisting of the sequence as set forth in SEQ ID NO: 21, SEQ ID NO: 23, SEQ ID NO: 25, SEQ ID NO: 27, SEQ ID NO: 29, SEQ ID NO: 31, and SEQ ID NO: 33.

20. The viral vector of claim 10, wherein the vestigial like 4 protein has a sequence selected from the group consisting of the sequence as set forth in SEQ ID NO: 23, SEQ ID NO: 25, SEQ ID NO: 27, SEQ ID NO: 29, SEQ ID NO: 31, and SEQ ID NO: 33.

* * * * *

UNITED STATES PATENT AND TRADEMARK OFFICE
CERTIFICATE OF CORRECTION

| | |
|---|---|
| PATENT NO. | : 11,319,354 B2 |
| APPLICATION NO. | : 16/925632 |
| DATED | : May 3, 2022 |
| INVENTOR(S) | : Zhiqiang Lin |

It is certified that error appears in the above-identified patent and that said Letters Patent is hereby corrected as shown below:

In the Claims

Column 85, Line 24: Claim 15, Delete "claim 4" and insert -- claim 10 --

Signed and Sealed this
Fourteenth Day of June, 2022

Katherine Kelly Vidal
*Director of the United States Patent and Trademark Office*